(12) United States Patent
Reynolds et al.

(10) Patent No.: US 12,383,246 B2
(45) Date of Patent: Aug. 12, 2025

(54) VESSEL CLOSURE DEVICE WITH IMPROVED SAFETY AND TRACT HEMOSTASIS

(71) Applicant: Abbott Cardiovascular Systems, Inc., Santa Clara, CA (US)

(72) Inventors: Timothy C. Reynolds, Sunnyvale, CA (US); Aaron M. Fortson, Fremont, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 25 days.

(21) Appl. No.: 17/492,418

(22) Filed: Oct. 1, 2021

(65) Prior Publication Data

US 2022/0110617 A1    Apr. 14, 2022

Related U.S. Application Data

(60) Provisional application No. 63/114,202, filed on Nov. 16, 2020, provisional application No. 63/090,556, filed on Oct. 12, 2020.

(51) Int. Cl.
*A61B 17/00*    (2006.01)
*A61L 24/04*    (2006.01)
(Continued)

(52) U.S. Cl.
CPC ........ *A61B 17/0057* (2013.01); *A61L 24/046* (2013.01); *A61L 31/06* (2013.01);
(Continued)

(58) Field of Classification Search
CPC ...... A61B 17/0057; A61B 2017/00592; A61B 2017/00597; A61B 2017/00615;
(Continued)

(56) References Cited

U.S. PATENT DOCUMENTS 1,147,743 A   7/1915 Melvin
1,413,255 A   4/1922 Cason
(Continued)

FOREIGN PATENT DOCUMENTS

AU    2004202152 A1    1/2005
AU    2004202234 A1    2/2005
(Continued)

OTHER PUBLICATIONS

US 9,642,619 B2, 05/2017, Prior et al. (withdrawn)
(Continued)

*Primary Examiner* — Jing Rui Ou
(74) *Attorney, Agent, or Firm* — Workman Nydegger

(57) ABSTRACT

A vessel closure device for delivering immediate hemostasis at a puncture site in a wall of a blood vessel includes an intravascular anchor having one or more suture attachment points, an extravascular cap having a lumen, a sealant, and a suture connected to at least one of the one or more suture attachment points of the intravascular anchor and threaded through the lumen of the extravascular cap, wherein each of the intravascular anchor, extravascular cap, sealant, and suture are formed of bioabsorbable materials.

13 Claims, 56 Drawing Sheets

(51) Int. Cl.
*A61L 31/06* (2006.01)
*A61L 31/14* (2006.01)
*A61L 24/00* (2006.01)

(52) U.S. Cl.
CPC ... *A61L 31/148* (2013.01); *A61B 2017/00592* (2013.01); *A61B 2017/00597* (2013.01); *A61B 2017/00615* (2013.01); *A61B 2017/0065* (2013.01); *A61B 2017/00663* (2013.01); *A61L 24/0042* (2013.01)

(58) Field of Classification Search
CPC .. A61B 2017/0065; A61B 2017/00663; A61L 24/046; A61L 31/06; A61L 31/148; A61L 24/0042
See application file for complete search history.

(56) References Cited

U.S. PATENT DOCUMENTS

| | | |
|---|---|---|
| 2,950,722 A | 8/1960 | Mellon |
| 3,028,648 A | 4/1962 | Renaud |
| 3,928,128 A | 12/1975 | Kollmar et al. |
| 4,195,013 A | 3/1980 | De Zarauz |
| 4,477,634 A | 10/1984 | Linder et al. |
| 4,526,938 A | 7/1985 | Churchill et al. |
| 4,712,566 A | 12/1987 | Hoek |
| 4,745,160 A | 5/1988 | Churchill et al. |
| 4,890,612 A * | 1/1990 | Kensey ............. A61B 17/0057 606/213 |
| 4,936,310 A | 6/1990 | Engstroem et al. |
| 4,941,473 A | 7/1990 | Tenerz et al. |
| 4,942,035 A | 7/1990 | Churchill et al. |
| 4,944,308 A | 7/1990 | Aangstroem Kerfeldt |
| 5,018,529 A | 5/1991 | Tenerz et al. |
| 5,085,223 A | 2/1992 | Lars et al. |
| 5,092,857 A | 3/1992 | Fleischhacker |
| 5,125,058 A | 6/1992 | Tenerz et al. |
| 5,129,889 A | 7/1992 | Hahn et al. |
| 5,143,661 A | 9/1992 | Lawter et al. |
| 5,217,495 A | 6/1993 | Kaplan et al. |
| 5,225,521 A | 7/1993 | Spinu |
| 5,226,423 A | 7/1993 | Tenerz et al. |
| 5,229,528 A | 7/1993 | Brake et al. |
| 5,236,431 A | 8/1993 | Gogolewski et al. |
| 5,264,614 A | 11/1993 | Brake |
| 5,264,617 A | 11/1993 | Brake |
| 5,264,626 A | 11/1993 | Brake et al. |
| 5,268,507 A | 12/1993 | Brake |
| 5,278,256 A | 1/1994 | Bellis |
| 5,280,427 A | 1/1994 | Magnusson et al. |
| 5,282,827 A | 2/1994 | Kensey et al. |
| 5,307,811 A | 5/1994 | Sigwart et al. |
| 5,342,627 A | 8/1994 | Chopra et al. |
| 5,350,399 A | 9/1994 | Erlebacher et al. |
| 5,364,408 A | 11/1994 | Gordon |
| 5,371,176 A | 12/1994 | Bezwada et al. |
| 5,378,801 A | 1/1995 | Reichert et al. |
| 5,411,520 A * | 5/1995 | Nash ................. F16G 11/101 606/151 |
| 5,462,983 A | 10/1995 | Bloembergen et al. |
| 5,470,829 A | 11/1995 | Prisell et al. |
| 5,529,736 A | 6/1996 | Shalaby et al. |
| 5,531,759 A * | 7/1996 | Kensey ............. A61B 17/0401 604/15 |
| 5,534,150 A | 7/1996 | Bastioli et al. |
| 5,540,715 A | 7/1996 | Katsaros et al. |
| 5,540,929 A | 7/1996 | Narayan et al. |
| 5,542,427 A | 8/1996 | Angstrom Kerfeldt |
| 5,630,833 A | 5/1997 | Katsaros et al. |
| 5,641,502 A | 6/1997 | Skalla et al. |
| 5,649,959 A | 7/1997 | Hannam et al. |
| 5,662,681 A | 9/1997 | Nash et al. |
| 5,674,231 A | 10/1997 | Green et al. |
| 5,676,689 A | 10/1997 | Kensey et al. |
| 5,694,946 A | 12/1997 | Tenerz et al. |
| 5,697,943 A | 12/1997 | Sauer et al. |
| 5,700,901 A | 12/1997 | Hurst et al. |
| 5,702,716 A | 12/1997 | Dunn et al. |
| 5,707,393 A | 1/1998 | Kensey et al. |
| 5,739,176 A | 4/1998 | Dunn et al. |
| 5,741,283 A | 4/1998 | Fahy |
| 5,753,234 A | 5/1998 | Lee et al. |
| 5,810,746 A | 9/1998 | Goldstein et al. |
| 5,810,826 A | 9/1998 | Angstrom et al. |
| 5,868,684 A | 2/1999 | Aakerfeldt et al. |
| 5,908,149 A | 6/1999 | Welch et al. |
| 5,916,585 A | 6/1999 | Cook et al. |
| 5,938,624 A | 8/1999 | Akerfeldt et al. |
| 5,972,023 A | 10/1999 | Tanner et al. |
| 5,984,853 A | 11/1999 | Smith |
| 5,997,568 A | 12/1999 | Liu |
| 6,045,570 A | 4/2000 | Epstein et al. |
| 6,056,768 A | 5/2000 | Cates et al. |
| 6,074,395 A | 6/2000 | Trott et al. |
| 6,089,103 A | 7/2000 | Smith |
| 6,090,052 A | 7/2000 | Akerfeldt et al. |
| 6,093,201 A | 7/2000 | Cooper et al. |
| 6,106,486 A | 8/2000 | Tenerz et al. |
| 6,112,598 A | 9/2000 | Tenerz et al. |
| 6,162,962 A | 12/2000 | Hinsch et al. |
| 6,179,863 B1 | 1/2001 | Kensey et al. |
| 6,182,513 B1 | 2/2001 | Stemme et al. |
| 6,184,313 B1 | 2/2001 | Roovers et al. |
| 6,193,951 B1 | 2/2001 | Ottoboni et al. |
| 6,194,050 B1 | 2/2001 | Koerber et al. |
| 6,203,802 B1 | 3/2001 | Handjani et al. |
| 6,241,732 B1 | 6/2001 | Overaker et al. |
| 6,241,740 B1 | 6/2001 | Davis et al. |
| 6,248,083 B1 | 6/2001 | Smith et al. |
| 6,264,673 B1 | 7/2001 | Egneloev et al. |
| 6,312,380 B1 | 11/2001 | Hoek et al. |
| 6,332,884 B1 | 12/2001 | Cooper |
| 6,335,383 B1 | 1/2002 | Scopelianos et al. |
| 6,352,667 B1 | 3/2002 | English |
| 6,368,341 B1 | 4/2002 | Abrahamson |
| 6,391,036 B1 | 5/2002 | Berg et al. |
| 6,409,677 B1 | 6/2002 | Tulkki |
| 6,425,911 B1 | 7/2002 | Akerfeldt et al. |
| 6,428,336 B1 | 8/2002 | Akerfeldt |
| 6,461,301 B2 | 10/2002 | Smith |
| 6,462,169 B1 | 10/2002 | Shalaby |
| 6,477,233 B1 | 11/2002 | Ribbing et al. |
| 6,485,503 B2 | 11/2002 | Jacobs et al. |
| 6,494,848 B1 | 12/2002 | Sommercorn et al. |
| 6,503,266 B1 | 1/2003 | Sjoegren et al. |
| 6,508,828 B1 | 1/2003 | Akerfeldt et al. |
| 6,511,748 B1 | 1/2003 | Barrows |
| 6,517,859 B1 | 2/2003 | Tice et al. |
| 6,561,966 B1 | 5/2003 | Smith et al. |
| 6,565,514 B2 | 5/2003 | Svanerudh et al. |
| 6,565,875 B2 | 5/2003 | Tice et al. |
| 6,582,971 B1 | 6/2003 | Singh et al. |
| 6,590,061 B1 | 7/2003 | Rypacek et al. |
| 6,596,012 B2 | 7/2003 | Akerfeldt et al. |
| 6,605,090 B1 | 8/2003 | Trieu et al. |
| 6,605,294 B2 | 8/2003 | Sawhney |
| 6,613,089 B1 | 9/2003 | Estes et al. |
| 6,615,067 B2 | 9/2003 | Hoek et al. |
| 6,615,667 B2 | 9/2003 | Smith |
| 6,623,418 B2 | 9/2003 | Smith |
| 6,623,509 B2 | 9/2003 | Ginn |
| 6,626,919 B1 | 9/2003 | Swanstrom |
| 6,645,226 B1 | 11/2003 | Jacobs |
| 6,663,653 B2 | 12/2003 | Akerfeldt |
| 6,685,707 B2 | 2/2004 | Roman et al. |
| 6,685,956 B2 | 2/2004 | Chu et al. |
| 6,689,374 B2 | 2/2004 | Chu et al. |
| 6,692,446 B2 | 2/2004 | Hoek |
| 6,696,073 B2 | 2/2004 | Boyce et al. |
| 6,706,854 B2 | 3/2004 | Buchholz et al. |
| 6,712,837 B2 | 3/2004 | Aakerfeldt et al. |
| 6,754,608 B2 | 6/2004 | Svanerudh et al. |
| 6,758,863 B2 | 7/2004 | Estes et al. |

(56) References Cited

U.S. PATENT DOCUMENTS

| | | |
|---|---|---|
| 6,770,717 B2 | 8/2004 | Kim et al. |
| 6,786,915 B2 | 9/2004 | Akerfeldt et al. |
| 6,790,455 B2 | 9/2004 | Chu et al. |
| 6,794,484 B2 | 9/2004 | Newman et al. |
| 6,794,485 B2 | 9/2004 | Shalaby et al. |
| 6,827,727 B2 | 12/2004 | Staalemark et al. |
| 6,830,747 B2 | 12/2004 | Lang et al. |
| 6,846,313 B1 | 1/2005 | Rogers et al. |
| 6,858,238 B2 | 2/2005 | Lee et al. |
| 6,881,434 B2 | 4/2005 | Pokropinski et al. |
| 6,887,974 B2 | 5/2005 | Pathak |
| 6,893,431 B2 | 5/2005 | Naimark et al. |
| 6,893,452 B2 | 5/2005 | Jacobs |
| 6,896,692 B2 | 5/2005 | Ginn et al. |
| 6,916,788 B2 | 7/2005 | Seo et al. |
| 6,926,674 B2 | 8/2005 | Tenerz et al. |
| 6,926,903 B2 | 8/2005 | Pirhonen et al. |
| 6,929,655 B2 | 8/2005 | Egneloev et al. |
| 6,932,824 B1 | 8/2005 | Roop et al. |
| 6,938,474 B2 | 9/2005 | Melvaas |
| 6,939,363 B2 | 9/2005 | Aakerfeldt |
| 6,942,674 B2 | 9/2005 | Belef et al. |
| 6,949,251 B2 | 9/2005 | Dalal et al. |
| 6,958,158 B2 | 10/2005 | Tenhuisen et al. |
| 6,960,352 B2 | 11/2005 | Noujaim et al. |
| 6,969,391 B1 | 11/2005 | Gazzani |
| 6,993,974 B2 | 2/2006 | Tenerz et al. |
| 7,011,636 B2 | 3/2006 | Tenerz |
| 7,011,678 B2 | 3/2006 | Tenerz et al. |
| 7,021,152 B2 | 4/2006 | Tenerz |
| 7,025,776 B1 | 4/2006 | Houser et al. |
| 7,026,437 B2 | 4/2006 | Shalaby et al. |
| 7,030,097 B1 | 4/2006 | Saltzman et al. |
| 7,044,916 B2 | 5/2006 | Tenerz et al. |
| 7,060,299 B2 | 6/2006 | Alavattam et al. |
| 7,070,858 B2 | 7/2006 | Shalaby et al. |
| 7,073,509 B2 | 7/2006 | Tenerz et al. |
| 7,074,412 B2 | 7/2006 | Weber |
| 7,086,172 B2 | 8/2006 | Aastroem |
| 7,094,209 B2 | 8/2006 | Egneloev et al. |
| 7,122,037 B2 | 10/2006 | Happonen et al. |
| 7,129,319 B2 | 10/2006 | Shalaby |
| 7,135,032 B2 | 11/2006 | Aakerfeldt |
| 7,156,862 B2 | 1/2007 | Jacobs et al. |
| 7,160,592 B2 | 1/2007 | Rypacek et al. |
| 7,162,303 B2 | 1/2007 | Levin et al. |
| 7,172,593 B2 | 2/2007 | Trieu et al. |
| 7,172,765 B2 | 2/2007 | Chu et al. |
| 7,222,539 B2 | 5/2007 | Tulkki |
| 7,250,057 B2 | 7/2007 | Forsberg |
| 7,264,641 B2 | 9/2007 | Prasad |
| 7,285,097 B2 | 10/2007 | Tenerz et al. |
| 7,323,190 B2 | 1/2008 | Chu et al. |
| 7,326,088 B2 | 2/2008 | Tulkki |
| 7,329,270 B2 | 2/2008 | Aakerfeldt et al. |
| 7,331,236 B2 | 2/2008 | Smith et al. |
| 7,331,979 B2 | 2/2008 | Khosravi et al. |
| 7,335,220 B2 | 2/2008 | Khosravi et al. |
| 7,338,514 B2 | 3/2008 | Wahr et al. |
| 7,343,811 B2 | 3/2008 | Tenerz et al. |
| 7,350,479 B2 | 4/2008 | Evans et al. |
| 7,357,793 B2 | 4/2008 | Pacetti |
| 7,364,768 B2 | 4/2008 | Rypacek et al. |
| 7,387,994 B2 | 6/2008 | Stewart et al. |
| 7,416,559 B2 | 8/2008 | Shalaby |
| 7,445,625 B2 | 11/2008 | Aakerfeldt |
| 7,450,989 B2 | 11/2008 | Svanerudh |
| 7,472,601 B1 | 1/2009 | Tenerz et al. |
| 7,481,839 B2 | 1/2009 | Zucherman et al. |
| 7,488,761 B2 | 2/2009 | Ricci et al. |
| 7,494,950 B2 | 2/2009 | Armitage et al. |
| 7,510,566 B2 | 3/2009 | Jacobs et al. |
| 7,541,049 B1 | 6/2009 | Toermaelae et al. |
| 7,553,919 B2 | 6/2009 | Narayan et al. |
| 7,575,780 B2 | 8/2009 | Alexander et al. |
| 7,582,110 B2 | 9/2009 | Case et al. |
| 7,597,705 B2 | 10/2009 | Forsberg et al. |
| 7,618,436 B2 | 11/2009 | Forsberg |
| 7,618,438 B2 | 11/2009 | White et al. |
| 7,621,937 B2 | 11/2009 | Pipenhagen et al. |
| 7,635,341 B2 | 12/2009 | Doorschodt |
| 7,637,921 B2 | 12/2009 | Aakerfeldt et al. |
| 7,637,924 B2 | 12/2009 | Gifford et al. |
| 7,645,233 B2 | 1/2010 | Tulkki et al. |
| 7,648,493 B2 | 1/2010 | Forsberg et al. |
| 7,654,963 B2 | 2/2010 | Egneloev et al. |
| 7,674,396 B2 | 3/2010 | Sterling et al. |
| 7,682,603 B2 | 3/2010 | Hammer et al. |
| 7,713,283 B2 | 5/2010 | Forsberg |
| 7,717,929 B2 | 5/2010 | Faellman |
| 7,722,914 B2 | 5/2010 | Shalaby |
| 7,724,148 B2 | 5/2010 | Samuelsson et al. |
| 7,731,726 B2 | 6/2010 | Belhe et al. |
| 7,744,916 B2 | 6/2010 | Pauletti et al. |
| 7,749,247 B2 | 7/2010 | Tegg |
| 7,749,248 B2 | 7/2010 | White et al. |
| 7,776,100 B2 | 8/2010 | Brekke et al. |
| 7,786,220 B2 | 8/2010 | Lee et al. |
| 7,789,887 B2 | 9/2010 | Roop et al. |
| 7,789,893 B2 | 9/2010 | Drasler et al. |
| 7,790,192 B2 | 9/2010 | Sawhney et al. |
| 7,806,856 B2 | 10/2010 | Bagaoisan et al. |
| 7,824,417 B2 | 11/2010 | Magnusson et al. |
| 7,828,845 B2 | 11/2010 | Estes et al. |
| 7,837,705 B2 | 11/2010 | White et al. |
| 7,842,261 B2 | 11/2010 | Van et al. |
| 7,850,614 B2 | 12/2010 | Haldeman |
| 7,850,654 B2 | 12/2010 | Belhe et al. |
| 7,850,710 B2 | 12/2010 | Huss |
| 7,863,352 B2 | 1/2011 | Ricci et al. |
| 7,875,052 B2 | 1/2011 | Kawaura et al. |
| 7,879,355 B2 | 2/2011 | Sterling et al. |
| 7,897,167 B2 | 3/2011 | Armstrong et al. |
| 7,926,567 B2 | 4/2011 | Harris et al. |
| 7,931,670 B2 | 4/2011 | Fiehler et al. |
| 7,931,671 B2 | 4/2011 | Tenerz |
| 7,938,846 B2 | 5/2011 | Kerfeldt et al. |
| 7,946,997 B2 | 5/2011 | Huebinette |
| 7,951,177 B2 | 5/2011 | Trieu et al. |
| 7,955,616 B2 | 6/2011 | Kronenthal |
| 7,967,761 B2 | 6/2011 | Smith |
| 7,972,359 B2 | 7/2011 | Kreidler |
| 7,976,564 B2 | 7/2011 | Blaeser et al. |
| 7,988,706 B2 | 8/2011 | Forsberg |
| 7,988,892 B2 | 8/2011 | Eisenhut et al. |
| 7,993,367 B2 | 8/2011 | Bagaoisan et al. |
| 7,997,054 B2 | 8/2011 | Bertsch et al. |
| 7,998,089 B2 | 8/2011 | Smith |
| 8,002,742 B2 | 8/2011 | Pai et al. |
| 8,007,514 B2 | 8/2011 | Forsberg |
| 8,012,167 B2 | 9/2011 | Zhu et al. |
| 8,016,841 B2 | 9/2011 | Magnusson et al. |
| 8,021,678 B2 | 9/2011 | Hossainy et al. |
| 8,021,869 B2 | 9/2011 | Chu et al. |
| 8,029,532 B2 | 10/2011 | Sirota |
| 8,029,533 B2 | 10/2011 | Bagaoisan et al. |
| 8,038,628 B2 | 10/2011 | Von et al. |
| 8,038,687 B2 | 10/2011 | Pipenhagen et al. |
| 8,048,086 B2 | 11/2011 | Lee-Sepsick et al. |
| 8,050,067 B2 | 11/2011 | Fulcher et al. |
| 8,057,817 B2 | 11/2011 | Shalaby |
| 8,075,531 B2 | 12/2011 | Davey |
| 8,075,589 B2 | 12/2011 | Pipenhagen et al. |
| 8,076,388 B2 | 12/2011 | Shalaby et al. |
| 8,080,034 B2 | 12/2011 | Bates et al. |
| 8,080,035 B2 | 12/2011 | Lim et al. |
| 8,083,755 B2 | 12/2011 | Mathisen et al. |
| 8,083,768 B2 | 12/2011 | Ginn et al. |
| 8,088,143 B2 | 1/2012 | Aakerfeldt |
| 8,088,145 B2 | 1/2012 | Zhu et al. |
| 8,105,352 B2 | 1/2012 | Egneloev |
| 8,109,274 B2 | 2/2012 | Horne et al. |
| 8,109,889 B2 | 2/2012 | Von et al. |
| 8,109,945 B2 | 2/2012 | Boehlke |

(56) References Cited

U.S. PATENT DOCUMENTS

| | | |
|---|---|---|
| 8,114,102 B2 | 2/2012 | Galdonik et al. |
| 8,114,123 B2 | 2/2012 | Brenzel et al. |
| 8,118,831 B2 | 2/2012 | Egneloev et al. |
| 8,128,652 B2 | 3/2012 | Paprocki |
| 8,133,225 B2 | 3/2012 | Pieske |
| 8,147,860 B2 | 4/2012 | Rosenberg et al. |
| 8,156,897 B2 | 4/2012 | Evans et al. |
| 8,187,195 B2 | 5/2012 | Tulkki |
| 8,211,351 B2 | 7/2012 | Gogolewski |
| 8,216,359 B2 | 7/2012 | Lee et al. |
| 8,221,781 B2 | 7/2012 | Rosenberg et al. |
| 8,226,715 B2 | 7/2012 | Hwang et al. |
| 8,231,686 B2 | 7/2012 | Mangiardi |
| 8,257,394 B2 | 9/2012 | Saadat et al. |
| 8,267,942 B2 | 9/2012 | Szabo et al. |
| 8,267,959 B2 | 9/2012 | Faellman |
| 8,273,094 B2 | 9/2012 | Belhe et al. |
| 8,277,481 B2 | 10/2012 | Kawaura et al. |
| 8,277,482 B2 | 10/2012 | Hruska et al. |
| 8,277,831 B2 | 10/2012 | Young et al. |
| 8,298,259 B2 | 10/2012 | Terwey |
| 8,299,205 B2 | 10/2012 | Shalaby et al. |
| 8,302,376 B2 | 11/2012 | Bertsch et al. |
| 8,308,758 B2 | 11/2012 | Aakerfeldt |
| 8,308,759 B2 | 11/2012 | Olsen et al. |
| 8,308,762 B2 | 11/2012 | Mahlin et al. |
| 8,317,679 B2 | 11/2012 | Surti |
| 8,317,824 B2 | 11/2012 | Jenson et al. |
| 8,323,351 B2 | 12/2012 | Kubena et al. |
| 8,347,891 B2 | 1/2013 | Demarais et al. |
| 8,348,917 B2 | 1/2013 | Beckman et al. |
| 8,348,971 B2 | 1/2013 | Khanna et al. |
| 8,371,142 B2 | 2/2013 | Nypeloe et al. |
| 8,382,752 B2 | 2/2013 | Ootsubo |
| 8,382,776 B2 | 2/2013 | Ducharme |
| 8,382,793 B2 | 2/2013 | Egneloev et al. |
| 8,382,797 B2 | 2/2013 | Khosravi et al. |
| 8,394,488 B2 | 3/2013 | Dave et al. |
| 8,398,675 B2 | 3/2013 | Egneloev |
| 8,398,705 B2 | 3/2013 | Mangiardi |
| 8,399,409 B2 | 3/2013 | Lynch et al. |
| 8,403,868 B2 | 3/2013 | Von et al. |
| 8,404,268 B2 | 3/2013 | Lee et al. |
| 8,409,249 B2 | 4/2013 | Hnojewyj et al. |
| 8,420,114 B2 | 4/2013 | Zanella et al. |
| 8,430,906 B2 | 4/2013 | Forsberg et al. |
| 8,444,673 B2 | 5/2013 | Thielen et al. |
| RE44,297 E | 6/2013 | Aakerfeldt et al. |
| 8,454,988 B2 | 6/2013 | Rosenberg et al. |
| 8,469,944 B2 | 6/2013 | Mahlin |
| 8,469,994 B2 | 6/2013 | Lafontaine |
| 8,470,360 B2 | 6/2013 | McKay |
| 8,475,829 B2 | 7/2013 | Sebree et al. |
| 8,475,830 B2 | 7/2013 | Sebree et al. |
| 8,479,585 B2 | 7/2013 | Shaw-Klein |
| 8,480,651 B2 | 7/2013 | Abuzaina et al. |
| 8,480,707 B2 | 7/2013 | Pavcnik et al. |
| 8,500,776 B2 | 8/2013 | Ebner |
| 8,506,592 B2 | 8/2013 | Killion et al. |
| 8,507,614 B2 | 8/2013 | Shalaby et al. |
| 8,512,372 B2 | 8/2013 | Egneloev et al. |
| 8,512,393 B2 | 8/2013 | Ginn et al. |
| 8,524,267 B2 | 9/2013 | Zanella et al. |
| 8,529,598 B2 | 9/2013 | Jenson et al. |
| 8,529,930 B2 | 9/2013 | Pacetti |
| 8,529,931 B2 | 9/2013 | Pacetti |
| 8,529,932 B2 | 9/2013 | Pacetti |
| 8,535,301 B2 | 9/2013 | Cox et al. |
| 8,540,750 B2 | 9/2013 | Tegels |
| 8,540,760 B2 | 9/2013 | Paul et al. |
| 8,579,825 B2 | 11/2013 | Tenerz et al. |
| 8,579,882 B1 | 11/2013 | Abuzaina et al. |
| 8,580,061 B2 | 11/2013 | Cik |
| 8,585,774 B2 | 11/2013 | Henderson |
| 8,586,087 B2 | 11/2013 | Lee et al. |
| 8,591,542 B2 | 11/2013 | White et al. |
| 8,591,875 B2 | 11/2013 | Belcheva et al. |
| 8,617,184 B2 | 12/2013 | Oepen |
| 8,623,396 B2 | 1/2014 | Gray et al. |
| 8,629,172 B2 | 1/2014 | McKay et al. |
| 8,636,767 B2 | 1/2014 | McClain |
| 8,636,792 B2 | 1/2014 | Zheng et al. |
| 8,641,633 B2 | 2/2014 | Smith |
| 8,647,364 B2 | 2/2014 | Fiehler et al. |
| 8,647,365 B2 | 2/2014 | Tegels |
| 8,647,368 B2 | 2/2014 | Ducharme |
| 8,652,166 B2 | 2/2014 | Aakerfeldt |
| 8,657,852 B2 | 2/2014 | Roorda et al. |
| 8,690,912 B2 | 4/2014 | Khanna et al. |
| 8,715,200 B2 | 5/2014 | Pijls |
| 8,721,679 B2 | 5/2014 | Drasler et al. |
| 8,721,680 B2 | 5/2014 | Hundertmark et al. |
| 8,722,079 B2 | 5/2014 | King |
| 8,726,438 B2 | 5/2014 | Cik |
| 8,734,366 B2 | 5/2014 | Egnelv et al. |
| 8,734,483 B2 | 5/2014 | Tekulve et al. |
| 8,735,504 B2 | 5/2014 | Clay |
| 8,740,982 B2 | 6/2014 | Lee |
| 8,753,115 B2 | 6/2014 | Schlottig et al. |
| 8,758,429 B2 | 6/2014 | Taylor et al. |
| 8,764,768 B2 | 7/2014 | Karpiel |
| 8,764,791 B2 | 7/2014 | Armstrong |
| 8,778,012 B2 | 7/2014 | Matheny |
| 8,778,379 B2 | 7/2014 | Doshi et al. |
| 8,782,101 B1 | 7/2014 | Moore |
| 8,790,488 B2 | 7/2014 | Hadba et al. |
| 8,790,684 B2 | 7/2014 | Dave et al. |
| 8,795,709 B2 | 8/2014 | Sawhney et al. |
| 8,795,762 B2 | 8/2014 | Fulton et al. |
| 8,802,124 B2 | 8/2014 | Tenerz et al. |
| 8,814,859 B2 | 8/2014 | Drasler et al. |
| 8,814,930 B2 | 8/2014 | Zheng et al. |
| 8,821,529 B2 | 9/2014 | Kariniemi et al. |
| 8,821,532 B2 | 9/2014 | Schaeffer |
| 8,828,419 B2 | 9/2014 | Dav et al. |
| 8,829,072 B2 | 9/2014 | Friess et al. |
| 8,834,562 B2 | 9/2014 | Chin-Chen et al. |
| 8,834,935 B2 | 9/2014 | Armbruster et al. |
| 8,835,492 B2 | 9/2014 | Lee et al. |
| 8,840,678 B2 | 9/2014 | Sudhir et al. |
| 8,846,068 B2 | 9/2014 | Wohabrebbi et al. |
| 8,852,229 B2 | 10/2014 | Ginn |
| 8,852,624 B2 | 10/2014 | Han et al. |
| 8,858,591 B2 | 10/2014 | Preinitz et al. |
| 8,864,843 B2 | 10/2014 | Lu et al. |
| 8,870,945 B2 | 10/2014 | Dave et al. |
| 8,877,226 B2 | 11/2014 | Zanella et al. |
| 8,906,042 B2 | 12/2014 | Hodgkinson et al. |
| 8,906,394 B2 | 12/2014 | Hossainy et al. |
| 8,911,766 B2 | 12/2014 | Hossainy et al. |
| 8,914,090 B2 | 12/2014 | Jain et al. |
| 8,920,463 B2 | 12/2014 | Mcguckin et al. |
| 8,926,545 B2 | 1/2015 | Brenneman et al. |
| 8,927,004 B1 | 1/2015 | Dehnad et al. |
| 8,932,615 B2 | 1/2015 | Pacetti |
| 8,936,635 B2 | 1/2015 | Kaesemeyer |
| 8,936,805 B2 | 1/2015 | Biris |
| 8,940,011 B2 | 1/2015 | Teoh et al. |
| 8,940,015 B2 | 1/2015 | Kariniemi |
| 8,945,173 B2 | 2/2015 | Atthoff et al. |
| 8,956,372 B2 | 2/2015 | Fenton et al. |
| 8,956,641 B2 | 2/2015 | Zanella et al. |
| 8,968,341 B2 | 3/2015 | Smith |
| 8,968,767 B2 | 3/2015 | McKay |
| 8,974,476 B2 | 3/2015 | Tegels |
| 8,974,776 B2 | 3/2015 | Stopek et al. |
| 8,980,317 B2 | 3/2015 | King |
| 8,992,567 B1 | 3/2015 | Houser |
| 9,004,920 B2 | 4/2015 | Schlottig et al. |
| 9,011,831 B2 | 4/2015 | Ding |
| 9,017,378 B2 | 4/2015 | Stocchero et al. |
| 9,017,653 B2 | 4/2015 | Balkus et al. |
| 9,023,074 B2 | 5/2015 | Theobald et al. |
| 9,023,379 B2 | 5/2015 | Pathak et al. |

(56) References Cited

U.S. PATENT DOCUMENTS

| | | |
|---|---|---|
| 9,031,792 B2 | 5/2015 | Wagner et al. |
| 9,034,011 B2 | 5/2015 | Kirsch et al. |
| 9,034,355 B2 | 5/2015 | Reynolds et al. |
| 9,039,738 B2 | 5/2015 | Pipenhagen et al. |
| 9,044,267 B2 | 6/2015 | Litvack et al. |
| 9,050,251 B2 | 6/2015 | Boyden et al. |
| 9,060,751 B2 | 6/2015 | Martin et al. |
| 9,060,842 B2 | 6/2015 | Karp et al. |
| 9,066,853 B2 | 6/2015 | Clay |
| 9,066,992 B2 | 6/2015 | Stankus et al. |
| 9,072,727 B2 | 7/2015 | McKay |
| 9,072,814 B2 | 7/2015 | Pathak et al. |
| 9,078,630 B2 | 7/2015 | Wahr et al. |
| 9,078,631 B2 | 7/2015 | Tegels |
| 9,089,262 B2 | 7/2015 | Hashiba |
| 9,089,391 B2 | 7/2015 | Kassab et al. |
| 9,089,412 B2 | 7/2015 | Kleiner |
| 9,089,594 B2 | 7/2015 | Dyer et al. |
| 9,095,342 B2 | 8/2015 | Becking et al. |
| 9,101,340 B2 | 8/2015 | Preinitz |
| 9,101,515 B2 | 8/2015 | Odermatt et al. |
| 9,101,695 B2 | 8/2015 | Langer et al. |
| 9,103,470 B2 | 8/2015 | Cik |
| 9,115,156 B2 | 8/2015 | Belcheva et al. |
| 9,125,902 B2 | 9/2015 | Haddock et al. |
| 9,125,917 B2 | 9/2015 | McKay et al. |
| 9,131,932 B2 | 9/2015 | Tegels |
| 9,132,119 B2 | 9/2015 | Hobot et al. |
| 9,132,194 B2 | 9/2015 | McKay |
| 9,132,204 B2 | 9/2015 | McKay et al. |
| 9,133,035 B2 | 9/2015 | Yun et al. |
| 9,144,487 B2 | 9/2015 | Wang et al. |
| 9,149,264 B2 | 10/2015 | Tegels |
| 9,149,290 B2 | 10/2015 | Goode et al. |
| 9,155,532 B2 | 10/2015 | Surti |
| 9,161,756 B2 | 10/2015 | Sargeant et al. |
| 9,173,645 B2 | 11/2015 | Overes et al. |
| 9,192,362 B2 | 11/2015 | Paul et al. |
| 9,192,364 B2 | 11/2015 | Terwey |
| 9,192,386 B2 | 11/2015 | Tegels et al. |
| 9,192,500 B1 | 11/2015 | Longo et al. |
| 9,211,285 B2 | 12/2015 | McKay et al. |
| 9,220,489 B2 | 12/2015 | Tegels |
| 9,220,815 B2 | 12/2015 | Pacetti |
| 9,220,816 B2 | 12/2015 | Pacetti |
| 9,226,738 B2 | 1/2016 | Defonzo et al. |
| 9,233,192 B2 | 1/2016 | Schwartz et al. |
| 9,241,694 B2 | 1/2016 | Tegels et al. |
| 9,241,708 B2 | 1/2016 | McCrea et al. |
| 9,254,124 B2 | 2/2016 | Drasler et al. |
| 9,265,733 B2 | 2/2016 | McKay |
| 9,265,857 B2 | 2/2016 | Garigapati et al. |
| 9,271,721 B2 | 3/2016 | Jimenez et al. |
| 9,271,834 B2 | 3/2016 | Kim et al. |
| 9,272,044 B2 | 3/2016 | Norton et al. |
| 9,277,904 B2 | 3/2016 | Paul et al. |
| 9,282,962 B2 | 3/2016 | Schmid et al. |
| 9,282,994 B2 | 3/2016 | Pipenhagen et al. |
| 9,289,197 B2 | 3/2016 | Forsberg |
| 9,289,409 B2 | 3/2016 | Zanella et al. |
| 9,289,534 B2 | 3/2016 | Lehtonen et al. |
| 9,295,650 B2 | 3/2016 | Neumann et al. |
| 9,301,740 B2 | 4/2016 | Thielen et al. |
| 9,301,741 B2 | 4/2016 | Schaeffer |
| 9,301,754 B2 | 4/2016 | Duncan |
| 9,301,946 B2 | 4/2016 | Wilsey et al. |
| 9,307,966 B2 | 4/2016 | Tegels |
| 9,307,967 B2 | 4/2016 | Tegels et al. |
| 9,314,545 B2 | 4/2016 | Tofighi et al. |
| 9,320,632 B1 | 4/2016 | Longo et al. |
| 9,320,833 B2 | 4/2016 | Pacetti |
| 9,332,991 B2 | 5/2016 | Pereira et al. |
| 9,345,460 B2 | 5/2016 | Houser et al. |
| 9,345,814 B2 | 5/2016 | Ding |
| 9,351,959 B2 | 5/2016 | McKay |
| 9,358,223 B2 | 6/2016 | King |
| 9,364,206 B2 | 6/2016 | Bagaoisan et al. |
| 9,364,207 B2 | 6/2016 | Terwey |
| 9,364,587 B2 | 6/2016 | Biris |
| 9,370,345 B2 | 6/2016 | Tegels et al. |
| 9,375,214 B2 | 6/2016 | Khanna et al. |
| 9,375,420 B2 | 6/2016 | King |
| 9,381,262 B2 | 7/2016 | Stephens et al. |
| 9,381,277 B2 | 7/2016 | Lehtonen et al. |
| 9,381,326 B2 | 7/2016 | Cully et al. |
| 9,386,968 B2 | 7/2016 | Uchida et al. |
| 9,387,197 B2 | 7/2016 | King |
| 9,398,902 B2 | 7/2016 | Paul et al. |
| 9,402,606 B2 | 8/2016 | Glazier et al. |
| 9,402,757 B2 | 8/2016 | Kassab et al. |
| 9,408,595 B2 | 8/2016 | Pipenhagen et al. |
| 9,408,607 B2 | 8/2016 | Cartledge et al. |
| 9,414,821 B2 | 8/2016 | Atanasoska et al. |
| 9,414,824 B2 | 8/2016 | Fortson et al. |
| 9,414,842 B2 | 8/2016 | Glimsdale et al. |
| 9,414,930 B2 | 8/2016 | Lee |
| 9,427,216 B2 | 8/2016 | Szabo et al. |
| 9,427,217 B2 | 8/2016 | Drasler et al. |
| 9,427,497 B2 | 8/2016 | Biris |
| 9,427,554 B2 | 8/2016 | Davey |
| 9,451,938 B2 | 9/2016 | Overes et al. |
| 9,452,242 B2 | 9/2016 | Dehnad et al. |
| 9,456,914 B2 | 10/2016 | Longo et al. |
| 9,457,133 B2 | 10/2016 | Ruane et al. |
| 9,463,004 B2 | 10/2016 | Campbell et al. |
| 9,464,368 B2 | 10/2016 | Zussman et al. |
| 9,468,429 B2 | 10/2016 | White |
| 9,468,706 B2 | 10/2016 | Glauser et al. |
| 9,469,919 B2 | 10/2016 | Kuhn et al. |
| 9,480,468 B2 | 11/2016 | Tegels |
| 9,486,191 B2 | 11/2016 | Gianotti et al. |
| 9,486,192 B2 | 11/2016 | Pipenhagen |
| 9,486,193 B2 | 11/2016 | Vidlund et al. |
| 9,486,302 B2 | 11/2016 | Boey et al. |
| 9,487,915 B2 | 11/2016 | Medoff |
| 9,492,156 B2 | 11/2016 | Tegels |
| 9,498,559 B2 | 11/2016 | Matheny |
| 9,504,457 B2 | 11/2016 | Szabo et al. |
| 9,511,018 B2 | 12/2016 | Clay et al. |
| 9,511,077 B2 | 12/2016 | Biggs et al. |
| 9,526,600 B2 | 12/2016 | Drapeau et al. |
| 9,526,812 B2 | 12/2016 | Doshi et al. |
| 9,528,044 B2 | 12/2016 | Van et al. |
| 9,533,072 B2 | 1/2017 | Matheny |
| 9,549,734 B2 | 1/2017 | Reydel |
| 9,549,740 B2 | 1/2017 | Rees |
| 9,549,920 B2 | 1/2017 | Wohabrebbi et al. |
| 9,550,977 B2 | 1/2017 | Isogai et al. |
| 9,554,783 B2 | 1/2017 | Pavcnik et al. |
| 9,554,784 B2 | 1/2017 | Vidlund |
| 9,561,611 B2 | 2/2017 | Kleiner |
| 9,566,371 B2 | 2/2017 | Zheng et al. |
| 9,585,643 B2 | 3/2017 | Terwey et al. |
| 9,585,645 B2 | 3/2017 | Akerfeldt |
| 9,585,782 B2 | 3/2017 | Longo et al. |
| 9,585,872 B2 | 3/2017 | Zanella et al. |
| 9,592,039 B2 | 3/2017 | Glazier et al. |
| 9,592,243 B2 | 3/2017 | Wilsey |
| 9,602,786 B2 | 3/2017 | Longo et al. |
| 9,603,588 B2 | 3/2017 | Kramer et al. |
| 9,603,601 B2 | 3/2017 | Tegels |
| 9,610,070 B2 | 4/2017 | Martin |
| 9,610,076 B2 | 4/2017 | Melsheimer et al. |
| 9,610,150 B2 | 4/2017 | Flanagan et al. |
| 9,616,104 B2 | 4/2017 | Binette |
| 9,617,465 B2 | 4/2017 | Gullickson et al. |
| 9,629,619 B2 | 4/2017 | Tenerz |
| 9,642,615 B2 | 5/2017 | Halac et al. |
| 9,655,602 B2 | 5/2017 | Ginn et al. |
| 9,662,099 B2 | 5/2017 | Grant et al. |
| 9,675,556 B2 | 6/2017 | Akala et al. |
| 9,681,866 B2 | 6/2017 | Halac et al. |
| 9,687,864 B2 | 6/2017 | Fulton et al. |
| 9,694,096 B2 | 7/2017 | McKay et al. |

(56) References Cited

U.S. PATENT DOCUMENTS

| | | |
|---|---|---|
| 9,694,104 B2 | 7/2017 | Matheny et al. |
| 9,700,567 B2 | 7/2017 | Zanella et al. |
| 9,707,000 B2 | 7/2017 | Hoke et al. |
| 9,713,462 B2 | 7/2017 | Bagaoisan et al. |
| 9,713,702 B2 | 7/2017 | Zare et al. |
| 9,717,456 B2 | 8/2017 | Lim |
| 9,717,487 B2 | 8/2017 | White et al. |
| 9,717,610 B2 | 8/2017 | Huang et al. |
| 9,717,779 B2 | 8/2017 | King |
| 9,724,079 B2 | 8/2017 | Shanley |
| 9,724,082 B2 | 8/2017 | Stanley et al. |
| 9,730,699 B2 | 8/2017 | Hglund |
| 9,737,286 B2 | 8/2017 | Grant et al. |
| 9,743,220 B2 | 8/2017 | Shahar et al. |
| 9,744,259 B2 | 8/2017 | Wang et al. |
| 9,750,489 B2 | 9/2017 | Pipenhagen et al. |
| 9,757,049 B2 | 9/2017 | Park et al. |
| 9,757,105 B2 | 9/2017 | Hundertmark et al. |
| 9,757,106 B2 | 9/2017 | Baxter et al. |
| 9,758,558 B2 | 9/2017 | Henry et al. |
| 9,763,652 B2 | 9/2017 | Terwey |
| 9,763,788 B2 | 9/2017 | Biris |
| 9,770,233 B2 | 9/2017 | Nelson |
| 9,782,155 B2 | 10/2017 | Mcguckin et al. |
| 9,782,168 B2 | 10/2017 | Shanley et al. |
| 9,782,402 B2 | 10/2017 | Norton et al. |
| 9,814,571 B2 | 11/2017 | Johnson et al. |
| 9,820,727 B2 | 11/2017 | Zhou et al. |
| 9,820,728 B2 | 11/2017 | Mylonakis et al. |
| 9,820,735 B2 | 11/2017 | Tegels |
| 9,820,839 B2 | 11/2017 | Jacinto et al. |
| 9,827,117 B2 | 11/2017 | Taylor et al. |
| 9,833,548 B2 | 12/2017 | McKay et al. |
| 9,839,415 B2 | 12/2017 | Tegels |
| 9,848,859 B2 | 12/2017 | White |
| 9,850,013 B2 | 12/2017 | Grant et al. |
| 9,855,034 B2 | 1/2018 | Broom et al. |
| 9,861,465 B2 | 1/2018 | Tan et al. |
| 9,872,680 B2 | 1/2018 | Fenton et al. |
| 9,873,790 B1 | 1/2018 | Andjelic et al. |
| 9,877,711 B2 | 1/2018 | Schaeffer |
| 9,883,936 B2 | 2/2018 | Sutton et al. |
| 9,888,848 B2 | 2/2018 | Samuelsson et al. |
| 9,895,144 B2 | 2/2018 | Tegels |
| 9,913,634 B2 | 3/2018 | Hansen |
| 9,918,924 B2 | 3/2018 | Dyer |
| 9,925,033 B2 | 3/2018 | Cartledge et al. |
| 9,937,337 B2 | 4/2018 | Powers et al. |
| 9,943,298 B2 | 4/2018 | Stanley et al. |
| 9,943,302 B2 | 4/2018 | Bennett |
| 9,943,410 B2 | 4/2018 | Hollister et al. |
| 9,943,426 B2 | 4/2018 | Sirhan et al. |
| 9,950,093 B2 | 4/2018 | Zussman et al. |
| 9,955,958 B2 | 5/2018 | Tegels |
| 9,956,313 B2 | 5/2018 | Tofighi et al. |
| 9,968,572 B2 | 5/2018 | Wilsey et al. |
| 9,968,711 B2 | 5/2018 | Biris |
| 9,968,712 B1 | 5/2018 | Han et al. |
| 9,980,719 B2 | 5/2018 | Tegels |
| 9,987,289 B2 | 6/2018 | Scher et al. |
| 9,999,409 B2 | 6/2018 | Ditter |
| 10,010,311 B2 | 7/2018 | Parsonage et al. |
| 10,016,188 B2 | 7/2018 | Jacobs et al. |
| 10,016,200 B2 | 7/2018 | Tegels |
| 10,023,474 B2 | 7/2018 | Ben et al. |
| 10,035,299 B2 | 7/2018 | Cik |
| 10,064,726 B1 | 9/2018 | Wei |
| 10,076,331 B2 | 9/2018 | Huang et al. |
| 10,076,431 B2 | 9/2018 | Sirhan et al. |
| 10,098,620 B2 | 10/2018 | Crabb et al. |
| 10,105,293 B2 | 10/2018 | Liu et al. |
| 10,106,402 B2 | 10/2018 | Han et al. |
| 10,111,648 B2 | 10/2018 | Tegels et al. |
| 10,130,365 B2 | 11/2018 | Hotter |
| 10,130,509 B2 | 11/2018 | Korigodskiy et al. |
| 10,143,700 B2 | 12/2018 | Koyakutty et al. |
| 10,149,677 B2 | 12/2018 | Belson et al. |
| 10,149,926 B2 | 12/2018 | Schewe et al. |
| 10,155,063 B2 | 12/2018 | Herr et al. |
| 10,182,800 B2 | 1/2019 | Uchida et al. |
| 10,183,786 B2 | 1/2019 | Aagaard et al. |
| 10,201,336 B2 | 2/2019 | Kariniemi et al. |
| 10,206,668 B2 | 2/2019 | McGoldrick et al. |
| 10,227,841 B2 | 3/2019 | Fripp et al. |
| 10,238,388 B2 | 3/2019 | Shelton et al. |
| 10,238,496 B2 | 3/2019 | Biris |
| 10,254,274 B2 | 4/2019 | Miklas et al. |
| 10,266,408 B2 | 4/2019 | Reynolds et al. |
| 10,271,976 B2 | 4/2019 | Sirhan et al. |
| 10,272,606 B2 | 4/2019 | McClain |
| 10,286,102 B2 | 5/2019 | Garigapati et al. |
| 10,314,567 B2 | 6/2019 | Uchida et al. |
| 10,327,747 B2 | 6/2019 | Yassinzadeh et al. |
| 10,335,419 B2 | 7/2019 | Scher et al. |
| 10,357,248 B2 | 7/2019 | Dalessandro et al. |
| 10,363,020 B2 | 7/2019 | Hill et al. |
| 10,376,254 B2 | 8/2019 | Eichenschink et al. |
| 10,390,707 B2 | 8/2019 | Kim et al. |
| 10,390,809 B2 | 8/2019 | Akerfeldt |
| 10,390,984 B2 | 8/2019 | Kassab et al. |
| 10,406,102 B2 | 9/2019 | Libin et al. |
| 10,426,449 B2 | 10/2019 | Fortson |
| 10,428,264 B2 | 10/2019 | Chopade et al. |
| 10,433,826 B2 | 10/2019 | Grant et al. |
| 10,441,426 B2 | 10/2019 | Wei |
| 10,441,757 B2 | 10/2019 | Kaufman et al. |
| 10,442,175 B2 | 10/2019 | Schlachter |
| 10,449,269 B2 | 10/2019 | Fahmy et al. |
| 10,456,123 B2 | 10/2019 | Hundertmark et al. |
| 10,456,124 B2 | 10/2019 | Mylonakis et al. |
| 10,499,893 B2 | 12/2019 | Hundertmark et al. |
| 10,517,984 B2 | 12/2019 | Diluccio et al. |
| 10,519,434 B2 | 12/2019 | Morhet et al. |
| 10,524,915 B2 | 1/2020 | Freeman et al. |
| 10,537,313 B2 | 1/2020 | Gianotti et al. |
| 10,542,996 B2 | 1/2020 | Willard et al. |
| 10,555,727 B2 | 2/2020 | Walters et al. |
| 10,590,388 B2 | 3/2020 | Ohta et al. |
| 10,595,838 B2 | 3/2020 | Bagaoisan et al. |
| 10,596,201 B2 | 3/2020 | Huang et al. |
| 10,603,473 B2 | 3/2020 | Kaufman et al. |
| 10,611,908 B2 | 4/2020 | Sheardown et al. |
| 10,624,619 B2 | 4/2020 | Amplatz et al. |
| 10,639,020 B2 | 5/2020 | Larzon et al. |
| 10,682,128 B2 | 6/2020 | Walters et al. |
| 10,702,275 B2 | 7/2020 | Adams et al. |
| 10,709,433 B2 | 7/2020 | Flanagan et al. |
| 10,716,549 B2 | 7/2020 | Keillor |
| 10,722,224 B2 | 7/2020 | Stopek et al. |
| 10,722,225 B2 | 7/2020 | Jacobs et al. |
| 10,722,445 B2 | 7/2020 | Dyer |
| 10,729,416 B2 | 8/2020 | Stanley et al. |
| 10,729,702 B2 | 8/2020 | Scher et al. |
| 10,736,985 B2 | 8/2020 | Odermatt et al. |
| 10,751,035 B2 | 8/2020 | White |
| 10,751,124 B2 | 8/2020 | Eisenfrats et al. |
| 10,758,216 B2 | 9/2020 | Stanley |
| 10,758,643 B2 | 9/2020 | Brosig et al. |
| 10,765,414 B2 | 9/2020 | White |
| 10,765,753 B2 | 9/2020 | Lee et al. |
| 10,786,374 B2 | 9/2020 | Sirhan et al. |
| 10,799,336 B2 | 10/2020 | Hutmacher et al. |
| 10,806,438 B2 | 10/2020 | Bagaoisan et al. |
| 10,813,763 B2 | 10/2020 | Schlachter |
| 10,835,223 B2 | 11/2020 | Pipenhagen |
| 10,849,607 B2 | 12/2020 | Stanley et al. |
| 10,849,619 B2 | 12/2020 | Viola et al. |
| 10,864,158 B2 | 12/2020 | Desai et al. |
| 10,869,708 B2 | 12/2020 | Preiss-Bloom et al. |
| 10,869,954 B2 | 12/2020 | Preiss-Bloom et al. |
| 10,874,384 B2 | 12/2020 | Uchida et al. |
| 10,874,402 B2 | 12/2020 | Cao et al. |
| 10,893,926 B2 | 1/2021 | Vantassel et al. |
| 10,898,353 B2 | 1/2021 | Taylor et al. |

(56) References Cited

U.S. PATENT DOCUMENTS

| | | | |
|---|---|---|---|
| 10,898,498 B2 | 1/2021 | Scher et al. |
| 10,918,505 B2 | 2/2021 | Sirhan et al. |
| 10,925,588 B2 | 2/2021 | Glimsdale |
| 10,926,004 B2 | 2/2021 | Preiss-Bloom et al. |
| RE48,485 E | 3/2021 | Piskun et al. |
| 10,939,937 B2 | 3/2021 | Terefe et al. |
| 10,945,716 B2 | 3/2021 | Chen et al. |
| 10,959,720 B2 | 3/2021 | Juan et al. |
| 10,966,698 B2 | 4/2021 | Grant et al. |
| 10,987,445 B2 | 4/2021 | McKay et al. |
| 10,993,719 B2 | 5/2021 | Jagelski et al. |
| 11,000,633 B2 | 5/2021 | Gonalves et al. |
| 11,045,178 B2 | 6/2021 | Onushko et al. |
| 11,051,801 B2 | 7/2021 | Roorda et al. |
| 11,053,361 B2 | 7/2021 | Legnetti et al. |
| 11,058,406 B2 | 7/2021 | Mylonakis et al. |
| 11,065,099 B2 | 7/2021 | Lu et al. |
| 11,096,733 B2 | 8/2021 | Frei et al. |
| 11,103,224 B2 | 8/2021 | Uchida et al. |
| 11,103,588 B2 | 8/2021 | Cao et al. |
| 11,110,208 B2 | 9/2021 | Koenig |
| 11,141,142 B2 | 10/2021 | McGoldrick et al. |
| 11,154,284 B2 | 10/2021 | Venkatraman et al. |
| 11,154,395 B2 | 10/2021 | Matheny |
| 11,154,510 B2 | 10/2021 | Albayrak |
| 11,167,055 B2 | 11/2021 | McKay et al. |
| 11,179,243 B2 | 11/2021 | Roeder et al. |
| 11,191,788 B2 | 12/2021 | Huang et al. |
| 11,219,436 B2 | 1/2022 | Mayberg |
| 11,220,096 B2 | 1/2022 | Schlachter |
| 11,225,551 B2 | 1/2022 | Zhang et al. |
| 11,259,841 B2 | 3/2022 | Pilletere et al. |
| 11,272,911 B2 | 3/2022 | Hundertmark et al. |
| 11,278,269 B2 | 3/2022 | Grant et al. |
| 11,278,641 B2 | 3/2022 | Herr et al. |
| 11,285,244 B2 | 3/2022 | Hoerstrup et al. |
| 11,299,822 B2 | 4/2022 | Zussman et al. |
| 11,311,650 B2 | 4/2022 | Dashti et al. |
| 11,317,957 B2 | 5/2022 | Preiss-Bloom et al. |
| 11,357,837 B2 | 6/2022 | King |
| 11,382,714 B2 | 7/2022 | O'Brien-Coon et al. |
| 11,406,377 B2 | 8/2022 | Schmid et al. |
| 11,413,242 B2 | 8/2022 | Peters |
| 11,439,378 B2 | 9/2022 | Gianotti et al. |
| 11,504,105 B2 | 11/2022 | Defonzo et al. |
| 11,529,130 B2 | 12/2022 | Vidlund |
| 11,534,150 B2 | 12/2022 | Uchida et al. |
| 11,576,663 B2 | 2/2023 | Walters et al. |
| 11,589,855 B2 | 2/2023 | Walters et al. |
| 11,707,265 B2 | 7/2023 | Bagaoisan et al. |
| 11,707,266 B2 | 7/2023 | Bagaoisan et al. |
| 11,717,278 B2 | 8/2023 | Yassinzadeh et al. |
| 11,737,740 B2 | 8/2023 | Joe et al. |
| 11,832,804 B2 | 12/2023 | Hundertmark et al. |
| 12,029,404 B2 | 7/2024 | Garrison |
| 12,035,905 B2 | 7/2024 | Wiebe et al. |
| 12,048,429 B2 | 7/2024 | Shattuck et al. |
| 12,156,643 B2 | 12/2024 | Grant et al. |
| 2002/0019648 A1* | 2/2002 | Akerfeldt ............ A61B 17/0057 606/213 |
| 2002/0054664 A1 | 5/2002 | Tiren |
| 2002/0054665 A1 | 5/2002 | Tiren |
| 2002/0161168 A1 | 10/2002 | Shalaby et al. |
| 2002/0183787 A1 | 12/2002 | Wahr et al. |
| 2002/0193808 A1 | 12/2002 | Belef et al. |
| 2002/0198562 A1 | 12/2002 | Akerfeldt et al. |
| 2003/0051735 A1* | 3/2003 | Pavcnik ............ A61B 17/12118 128/831 |
| 2003/0060846 A1 | 3/2003 | Egnelov et al. |
| 2003/0093108 A1 | 5/2003 | Avellanet et al. |
| 2004/0039413 A1 | 2/2004 | Akerfeldt et al. |
| 2004/0093025 A1* | 5/2004 | Egnelov ............ A61B 17/0487 606/214 |
| 2004/0168519 A1 | 9/2004 | Kalvensten et al. |
| 2004/0225232 A1 | 11/2004 | Malmborg et al. |
| 2005/0085852 A1 | 4/2005 | Ditter |
| 2005/0085855 A1 | 4/2005 | Forsberg |
| 2005/0107827 A1 | 5/2005 | Paprocki |
| 2005/0169974 A1* | 8/2005 | Tenerz ............ A61L 31/04 424/445 |
| 2005/0203552 A1 | 9/2005 | Laufer et al. |
| 2005/0267521 A1 | 12/2005 | Forsberg |
| 2005/0283193 A1 | 12/2005 | Tullberg et al. |
| 2006/0009817 A1 | 1/2006 | Tulkki |
| 2006/0034930 A1* | 2/2006 | Khosravi ............ A61K 9/0024 424/484 |
| 2006/0052700 A1 | 3/2006 | Svanerudh |
| 2006/0058844 A1 | 3/2006 | White et al. |
| 2006/0142786 A1 | 6/2006 | Mathisen et al. |
| 2006/0142798 A1 | 6/2006 | Holman et al. |
| 2006/0161224 A1 | 7/2006 | Samuelsson et al. |
| 2006/0173492 A1 | 8/2006 | Akerfeldt et al. |
| 2006/0178682 A1 | 8/2006 | Boehlke |
| 2006/0205910 A1 | 9/2006 | Asplund et al. |
| 2006/0211839 A1 | 9/2006 | Asplund et al. |
| 2006/0229672 A1 | 10/2006 | Forsberg |
| 2006/0247653 A1 | 11/2006 | Akerfeldt et al. |
| 2006/0264978 A1 | 11/2006 | Belhe et al. |
| 2007/0032824 A1 | 2/2007 | Terwey |
| 2007/0093869 A1 | 4/2007 | Bloom et al. |
| 2007/0149880 A1 | 6/2007 | Willis |
| 2007/0150002 A1 | 6/2007 | Szabo et al. |
| 2007/0156084 A1 | 7/2007 | Belhe et al. |
| 2007/0185530 A1 | 8/2007 | Chin-Chen et al. |
| 2007/0225755 A1 | 9/2007 | Preinitz et al. |
| 2007/0225756 A1 | 9/2007 | Preinitz et al. |
| 2007/0225757 A1 | 9/2007 | Preinitz et al. |
| 2007/0225758 A1 | 9/2007 | Preinitz et al. |
| 2007/0255145 A1 | 11/2007 | Smith et al. |
| 2007/0276433 A1 | 11/2007 | Huss |
| 2008/0009794 A1 | 1/2008 | Bagaoisan et al. |
| 2008/0015636 A1 | 1/2008 | Olsen et al. |
| 2008/0077050 A1 | 3/2008 | Von et al. |
| 2008/0082123 A1 | 4/2008 | Forsberg et al. |
| 2008/0091235 A1 | 4/2008 | Sirota |
| 2008/0097479 A1 | 4/2008 | Boehlke et al. |
| 2008/0097480 A1 | 4/2008 | Schorr et al. |
| 2008/0097481 A1 | 4/2008 | Schorr et al. |
| 2008/0097484 A1 | 4/2008 | Lim et al. |
| 2008/0114395 A1 | 5/2008 | Mathisen et al. |
| 2008/0154190 A1 | 6/2008 | St et al. |
| 2008/0200798 A1 | 8/2008 | Eklund et al. |
| 2008/0243182 A1 | 10/2008 | Bates et al. |
| 2008/0262475 A1 | 10/2008 | Preinitz |
| 2008/0302682 A1 | 12/2008 | Engstrom et al. |
| 2008/0319458 A1 | 12/2008 | Reynolds |
| 2009/0030450 A1 | 1/2009 | Preinitz et al. |
| 2009/0036919 A1 | 2/2009 | Preinitz et al. |
| 2009/0036920 A1 | 2/2009 | Preinitz et al. |
| 2009/0054926 A1 | 2/2009 | Pipenhagen et al. |
| 2009/0069844 A1 | 3/2009 | Green et al. |
| 2009/0118643 A1 | 5/2009 | Smith et al. |
| 2009/0171281 A1 | 7/2009 | Pipenhagen et al. |
| 2009/0171282 A1 | 7/2009 | Pipenhagen et al. |
| 2009/0171387 A1 | 7/2009 | Pipenhagen et al. |
| 2009/0234377 A1* | 9/2009 | Mahlin ............ A61B 17/0057 606/153 |
| 2009/0312790 A1 | 12/2009 | Forsberg et al. |
| 2010/0004671 A1 | 1/2010 | Gerberding et al. |
| 2010/0023051 A1 | 1/2010 | White et al. |
| 2010/0042118 A1 | 2/2010 | Garrison et al. |
| 2010/0042144 A1 | 2/2010 | Bennett |
| 2010/0061518 A1 | 3/2010 | Smith |
| 2010/0069924 A1 | 3/2010 | Kochman et al. |
| 2010/0109104 A1 | 5/2010 | Tiensuu et al. |
| 2010/0145366 A1 | 6/2010 | Roop et al. |
| 2010/0168789 A1 | 7/2010 | Bagaoisan et al. |
| 2010/0179567 A1 | 7/2010 | Voss et al. |
| 2010/0179588 A1 | 7/2010 | Sater et al. |
| 2010/0179589 A1 | 7/2010 | Roorda et al. |
| 2010/0185234 A1 | 7/2010 | Fortson et al. |
| 2010/0191280 A1 | 7/2010 | Forsberg |
| 2010/0217308 A1* | 8/2010 | Hansen ............ A61B 17/0057 606/228 |

(56) References Cited

U.S. PATENT DOCUMENTS

| | | |
|---|---|---|
| 2010/0234883 A1 | 9/2010 | White et al. |
| 2010/0286727 A1 | 11/2010 | Terwey |
| 2010/0312224 A1 | 12/2010 | Atthoff et al. |
| 2011/0029012 A1 | 2/2011 | Tegels |
| 2011/0046663 A1 | 2/2011 | Zhou et al. |
| 2011/0077683 A1 | 3/2011 | Huss |
| 2011/0172702 A1 | 7/2011 | Fiehler et al. |
| 2011/0218568 A1 | 9/2011 | Voss |
| 2011/0224725 A1 | 9/2011 | De et al. |
| 2011/0270302 A1 | 11/2011 | Forsberg |
| 2011/0301619 A1 | 12/2011 | Walters |
| 2012/0000467 A1 | 1/2012 | Milne et al. |
| 2012/0004669 A1 | 1/2012 | Overes et al. |
| 2012/0022562 A1 | 1/2012 | Willard |
| 2012/0035629 A1 | 2/2012 | Sherwinter |
| 2012/0035653 A1 | 2/2012 | Shoemaker et al. |
| 2012/0101519 A1 | 4/2012 | Hill et al. |
| 2012/0116447 A1 | 5/2012 | Stanley et al. |
| 2012/0143226 A1 | 6/2012 | Belson et al. |
| 2012/0143243 A1 | 6/2012 | Hill et al. |
| 2012/0143244 A1 | 6/2012 | Hill et al. |
| 2012/0209323 A1 | 8/2012 | Uchida et al. |
| 2012/0259346 A1 | 10/2012 | Hansen et al. |
| 2013/0103077 A1 | 4/2013 | Ditter |
| 2013/0123844 A1 | 5/2013 | White |
| 2013/0190813 A1 | 7/2013 | Tegels et al. |
| 2013/0253579 A1 | 9/2013 | Hundertmark et al. |
| 2013/0310853 A1 | 11/2013 | Zaugg et al. |
| 2013/0325060 A1 | 12/2013 | Jenson et al. |
| 2014/0094846 A1 | 4/2014 | Lim |
| 2014/0142618 A1 | 5/2014 | Leopold et al. |
| 2014/0142620 A1 | 5/2014 | Marchi et al. |
| 2014/0194918 A1 | 7/2014 | Tegels |
| 2014/0194925 A1 | 7/2014 | Lim et al. |
| 2014/0228868 A1 | 8/2014 | Hassan et al. |
| 2014/0276973 A1 | 9/2014 | Tegels |
| 2014/0277111 A1 | 9/2014 | Tegels |
| 2014/0288640 A1 | 9/2014 | Ginn et al. |
| 2014/0296907 A1 | 10/2014 | Khanna et al. |
| 2014/0364899 A1 | 12/2014 | Ginn et al. |
| 2015/0051641 A1 | 2/2015 | Baxter |
| 2015/0157332 A1 | 6/2015 | Obermiller et al. |
| 2015/0282789 A1 | 10/2015 | Huber |
| 2015/0297202 A1 | 10/2015 | Khosravi et al. |
| 2015/0327843 A1 | 11/2015 | Garrison |
| 2016/0022035 A1 | 1/2016 | Hardy |
| 2016/0081680 A1 | 3/2016 | Taylor |
| 2016/0220235 A1 | 8/2016 | Almedhychy |
| 2016/0262742 A1 | 9/2016 | Tegels |
| 2017/0086804 A1 | 3/2017 | Larzon et al. |
| 2017/0119400 A1 | 5/2017 | Amplatz et al. |
| 2017/0209131 A1 | 7/2017 | Penner et al. |
| 2017/0281142 A1 | 10/2017 | Martin et al. |
| 2017/0319189 A1 | 11/2017 | Grant et al. |
| 2017/0333014 A1 | 11/2017 | Grant et al. |
| 2017/0367710 A1 | 12/2017 | Yang |
| 2018/0028166 A1 | 2/2018 | Mylonakis et al. |
| 2018/0199926 A1 | 7/2018 | Jacobs et al. |
| 2018/0235636 A1 | 8/2018 | Culbert et al. |
| 2018/0271445 A1 | 9/2018 | Braido et al. |
| 2018/0368857 A1 | 12/2018 | Willard et al. |
| 2019/0000432 A1 | 1/2019 | Stanley et al. |
| 2019/0000504 A1 | 1/2019 | Terefe et al. |
| 2019/0015087 A1 | 1/2019 | Tegels et al. |
| 2019/0029659 A1 | 1/2019 | Uchida et al. |
| 2019/0192127 A1 | 6/2019 | Hundertmark et al. |
| 2019/0231326 A1 | 8/2019 | Joe et al. |
| 2019/0231333 A1 | 8/2019 | Tegels et al. |
| 2019/0274668 A1 | 9/2019 | Glimsdale et al. |
| 2019/0336115 A1 | 11/2019 | Uchida et al. |
| 2019/0336116 A1 | 11/2019 | Walters et al. |
| 2019/0343497 A1 | 11/2019 | Walters et al. |
| 2019/0388077 A1 | 12/2019 | Phillips |
| 2020/0051313 A1 | 2/2020 | Uludag |
| 2020/0054313 A1 | 2/2020 | Hundertmark et al. |
| 2020/0054343 A1 | 2/2020 | Min et al. |
| 2020/0078157 A1 | 3/2020 | McLawhorn et al. |
| 2020/0107823 A1 | 4/2020 | Hundertmark et al. |
| 2020/0129165 A1 | 4/2020 | Bagaoisan et al. |
| 2020/0205828 A1 | 7/2020 | Kawaura et al. |
| 2020/0315827 A1 | 10/2020 | Longo et al. |
| 2020/0345306 A1 | 11/2020 | Samuelsson et al. |
| 2020/0367905 A1 | 11/2020 | Drilling et al. |
| 2020/0375582 A1 | 12/2020 | Bagaoisan et al. |
| 2020/0397474 A1 | 12/2020 | Pilletere et al. |
| 2021/0030405 A1 | 2/2021 | Mylonakis et al. |
| 2021/0059650 A1 | 3/2021 | Eidenschink et al. |
| 2021/0059684 A1 | 3/2021 | Meyer et al. |
| 2021/0100604 A1 | 4/2021 | Maruyama |
| 2021/0145421 A1 | 5/2021 | Hauck et al. |
| 2021/0386414 A1 | 12/2021 | Grant et al. |
| 2022/0031294 A1 | 2/2022 | Grant et al. |
| 2022/0096069 A1 | 3/2022 | Genereux et al. |
| 2022/0125419 A1 | 4/2022 | Mylonakis et al. |
| 2022/0183674 A1 | 6/2022 | Wiebe et al. |
| 2022/0192644 A1 | 6/2022 | Hundertmark et al. |
| 2022/0225975 A1 | 7/2022 | Uchida et al. |
| 2022/0265144 A1 | 8/2022 | Hbinette et al. |
| 2022/0370054 A1 | 11/2022 | DeFonzo et al. |
| 2022/0370057 A1 | 11/2022 | Gianotti et al. |
| 2023/0050024 A1 | 2/2023 | Van Niekerk |
| 2023/0070873 A1 | 3/2023 | Hundertmark et al. |
| 2023/0149004 A1 | 5/2023 | Vidlund |
| 2023/0172598 A1 | 6/2023 | Tawk |
| 2024/0090883 A1 | 3/2024 | Joe et al. |
| 2024/0138824 A1 | 5/2024 | Hauck et al. |
| 2024/0215968 A1 | 7/2024 | Genereux et al. |
| 2025/0032107 A1 | 1/2025 | Grant et al. |

FOREIGN PATENT DOCUMENTS

| | | |
|---|---|---|
| CA | 2776597 A1 | 1/2013 |
| EP | 0421966 A1 | 4/1991 |
| EP | 0662802 B1 | 5/1998 |
| EP | 0955902 A1 | 11/1999 |
| EP | 0973438 A1 | 1/2000 |
| EP | 1147743 A1 | 10/2001 |
| EP | 1169968 A1 | 1/2002 |
| EP | 0766947 B1 | 2/2002 |
| EP | 1217642 A1 | 6/2002 |
| EP | 0774237 B1 | 4/2003 |
| EP | 1413255 A1 | 4/2004 |
| EP | 1440661 A1 | 7/2004 |
| EP | 1501421 A1 | 2/2005 |
| EP | 1574168 A1 | 9/2005 |
| EP | 1641399 A1 | 4/2006 |
| EP | 1658811 A1 | 5/2006 |
| EP | 1671592 A1 | 6/2006 |
| EP | 1680029 A2 | 7/2006 |
| EP | 1700872 A2 | 9/2006 |
| EP | 2002800 A1 | 12/2008 |
| EP | 1976438 B1 | 6/2010 |
| EP | 2323566 A2 | 5/2011 |
| EP | 2416711 A2 | 2/2012 |
| EP | 2519161 A2 | 11/2012 |
| EP | 2538848 A2 | 1/2013 |
| EP | 2640277 A1 | 9/2013 |
| EP | 2717781 A1 | 4/2014 |
| EP | 2747667 A1 | 7/2014 |
| EP | 2747668 A1 | 7/2014 |
| EP | 2819586 A2 | 1/2015 |
| EP | 1869301 B1 | 10/2015 |
| EP | 2950722 A1 | 12/2015 |
| EP | 2364112 B1 | 3/2016 |
| EP | 3007631 A2 | 4/2016 |
| EP | 2019631 B1 | 11/2016 |
| EP | 2548518 B1 | 9/2017 |
| EP | 3001954 B1 | 1/2018 |
| EP | 2405824 B1 | 8/2018 |
| EP | 3355803 A1 | 8/2018 |
| EP | 3431023 A2 | 1/2019 |
| EP | 3278740 B1 | 12/2019 |
| EP | 3342448 B1 | 12/2019 |
| EP | 3490461 B1 | 12/2019 |

(56) References Cited

FOREIGN PATENT DOCUMENTS

| | | | |
|---|---|---|---|
| EP | 3573538 A1 | 12/2019 |
| EP | 3582695 A1 | 12/2019 |
| EP | 2782506 B1 | 2/2020 |
| EP | 3459467 B1 | 4/2020 |
| EP | 3210542 B1 | 7/2020 |
| EP | 3305207 B1 | 8/2020 |
| EP | 2845613 B1 | 1/2021 |
| EP | 3821817 A2 | 5/2021 |
| EP | 3821820 A1 | 5/2021 |
| EP | 3659523 B1 | 6/2021 |
| EP | 3193738 B1 | 8/2021 |
| EP | 3881771 A1 | 9/2021 |
| EP | 3905963 A1 | 11/2021 |
| EP | 3908177 A1 | 11/2021 |
| EP | 3461420 B1 | 1/2022 |
| EP | 3650075 B1 | 7/2022 |
| EP | 4061244 A1 | 9/2022 |
| EP | 3256051 B1 | 11/2022 |
| EP | 3871612 B1 | 3/2023 |
| EP | 4199832 A1 | 6/2023 |
| EP | 4259008 A1 | 10/2023 |
| EP | 4259009 A1 | 10/2023 |
| EP | 3217888 B1 | 5/2024 |
| EP | 3745962 B1 | 5/2024 |
| EP | 4426204 A1 | 9/2024 |
| JP | 05-212038 A | 8/1993 |
| JP | 2006-167468 A | 6/2006 |
| JP | 2014-509884 A | 4/2014 |
| SE | 9003758 L | 2/1991 |
| WO | 90/12537 A1 | 11/1990 |
| WO | 91/01772 A1 | 2/1991 |
| WO | 94/05221 A1 | 3/1994 |
| WO | 94/28800 A1 | 12/1994 |
| WO | 96/25110 A1 | 8/1996 |
| WO | 98/31287 A1 | 7/1998 |
| WO | 98/42253 A1 | 10/1998 |
| WO | 99/22646 A1 | 5/1999 |
| WO | 03/71956 A2 | 9/2003 |
| WO | 2006/115904 A2 | 11/2006 |
| WO | 2007/078812 A2 | 7/2007 |
| WO | 2007/139755 A2 | 12/2007 |
| WO | 2009/054800 A1 | 4/2009 |
| WO | 2009/054801 A1 | 4/2009 |
| WO | 2009/054802 A1 | 4/2009 |
| WO | 2009/054803 A1 | 4/2009 |
| WO | 2009/054805 A1 | 4/2009 |
| WO | 2010/019719 A2 | 2/2010 |
| WO | 2010/081102 A2 | 7/2010 |
| WO | 2010/107698 A2 | 9/2010 |
| WO | 2010/118312 A2 | 10/2010 |
| WO | 2011/037866 A1 | 3/2011 |
| WO | 2011/080588 A2 | 7/2011 |
| WO | 2011/106713 A2 | 9/2011 |
| WO | 2012/006161 A2 | 1/2012 |
| WO | 2012/158738 A1 | 11/2012 |
| WO | 2012/158740 A1 | 11/2012 |
| WO | 2012/170597 A1 | 12/2012 |
| WO | 2013/074488 A1 | 5/2013 |
| WO | 2013/074490 A1 | 5/2013 |
| WO | 2013/101366 A1 | 7/2013 |
| WO | 2013/115993 A1 | 8/2013 |
| WO | 2013/128292 A2 | 9/2013 |
| WO | 2013/142515 A1 | 9/2013 |
| WO | 2013/188575 A1 | 12/2013 |
| WO | 2014/031259 A3 | 4/2014 |
| WO | 2014/067021 A2 | 5/2014 |
| WO | 2014/120315 A1 | 8/2014 |
| WO | 2014/144741 A1 | 9/2014 |
| WO | 2014/201105 A2 | 12/2014 |
| WO | 2015/175537 A1 | 11/2015 |
| WO | 2016/014496 A2 | 1/2016 |
| WO | 2016/073870 A1 | 5/2016 |
| WO | 2017/055919 A1 | 4/2017 |
| WO | 2018/152457 A1 | 8/2018 |
| WO | 2019/003051 A2 | 1/2019 |
| WO | 2020/141122 A1 | 7/2020 |
| WO | 2020/146688 A1 | 7/2020 |
| WO | 2021/102044 A1 | 5/2021 |
| WO | 2022/081357 A1 | 4/2022 |
| WO | 2023/063780 A1 | 4/2023 |
| WO | 2023/073137 A1 | 5/2023 |
| WO | 2023/126843 A2 | 7/2023 |
| WO | 2024/092233 A2 | 5/2024 |

OTHER PUBLICATIONS

Advisory Action received for U.S. Appl. No. 12/106,928, mailed on Mar. 25, 2014, 3 pages.
Issue Notification received for U.S. Appl. No. 11/396,141, mailed on Mar. 19, 2014, 1 page.
Notice of Allowance received for U.S. Appl. No. 11/113,549, mailed on Mar. 14, 2014, 13 pages.
Notice of Allowance received for U.S. Appl. No. 11/411,925, mailed on Feb. 5, 2014, 9 pages.
Notice of Allowance received for U.S. Appl. No. 11/674,930, mailed on Apr. 3, 2014, 11 pages.
Notice of Allowance received for U.S. Appl. No. 11/852,190, mailed on Feb. 12, 2014, 9 pages.
Notice of Allowance received for U.S. Appl. No. 12/848,642, mailed on Feb. 3, 2014, 10 pages.
Notice of Allowance received for U.S. Appl. No. 12/941,809, mailed on Feb. 3, 2014, 7 pages.
Office Action received for U.S. Appl. No. 11/455,993, mailed on Jan. 29, 2014, 11 pages.
Office Action received for U.S. Appl. No. 12/106,937, mailed on Jan. 22, 2014, 7 pages.
Office Action received for U.S. Appl. No. 12/113,851, mailed on Mar. 17, 2014, 12 pages.
Office Action received for U.S. Appl. No. 12/114,031, mailed on Mar. 10, 2014, 9 pages.
Office Action received for U.S. Appl. No. 12/403,277, mailed on Jan. 27, 2014, 9 pages.

* cited by examiner

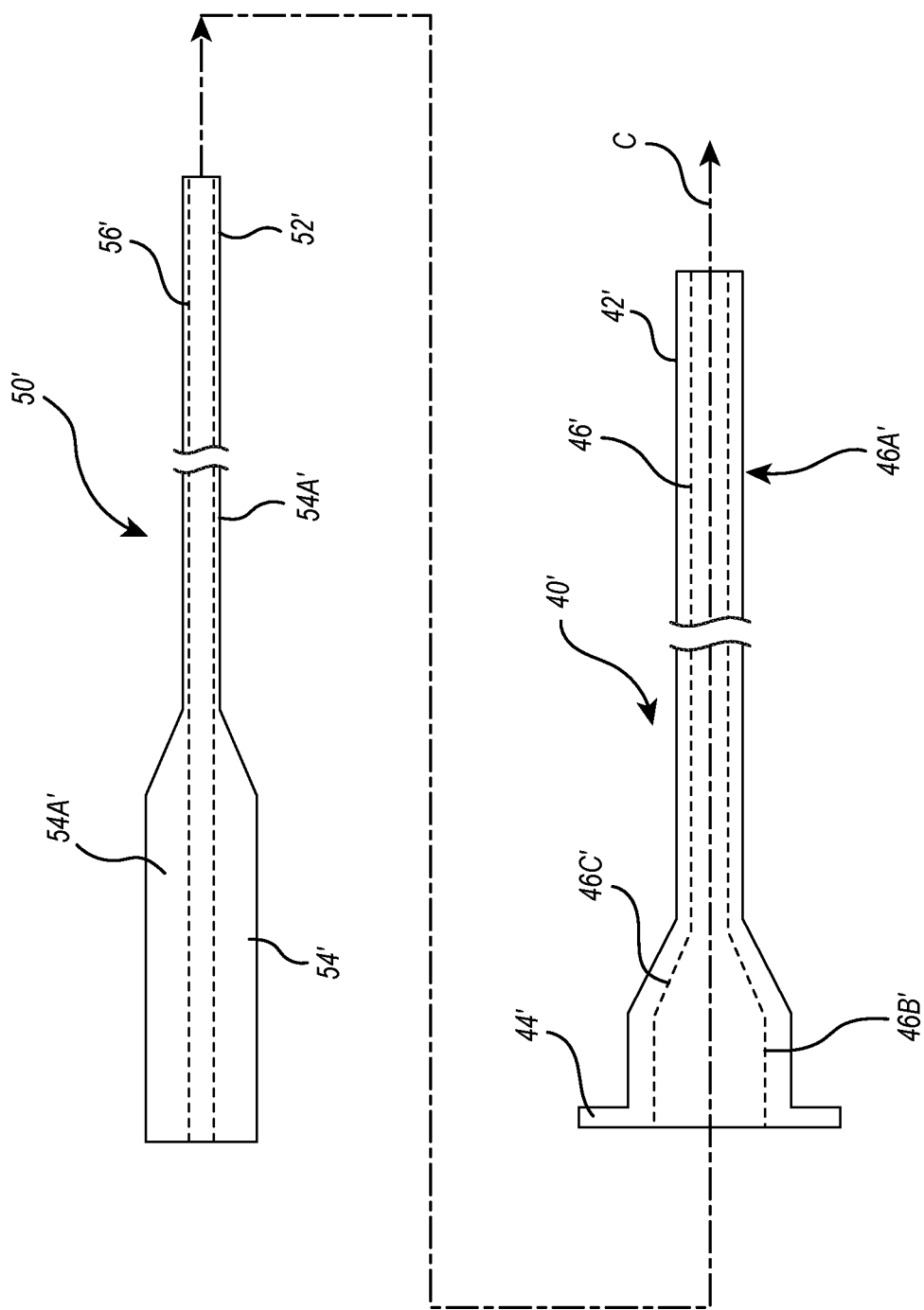

VESSEL CLOSURE DEVICE WITH IMPROVED SAFETY AND TRACT HEMOSTASIS

CROSS REFERENCE

This application claims the benefit of priority to U.S. Provisional Patent Application Ser. No. 63/090,556, filed Oct. 12, 2020, and to U.S. Provisional Patent Application Ser. No. 63/114,202, filed Nov. 16, 2020, the disclosures of which are incorporated herein in their entireties.

BACKGROUND

1. The Field of the Invention

The present disclosure relates generally to systems, devices, and methods for blocking an opening in body lumens. More particularly, the present disclosure relates to techniques for percutaneous closure of arterial and venous puncture sites, which are usually accessed through a tissue tract.

2. The Relevant Technology

A number of diagnostic and interventional vascular procedures are now performed translumenally. A catheter is introduced to the vascular system at a convenient access location and guided through the vascular system to a target location using established techniques. Such procedures require vascular access, which is usually established during the well-known Seldinger technique. Vascular access is generally provided through an introducer sheath, which is positioned to extend from outside the patient body into the vascular lumen. When vascular access is no longer required, the introducer sheath is removed and bleeding at the puncture site stopped.

One common approach for providing hemostasis (the cessation of bleeding) is to apply external force near and upstream from the puncture site, typically by manual compression. This approach suffers from a number of disadvantages. For example, the manual compression procedure is time consuming, frequently requiring one-half hour or more of compression before hemostasis is achieved. Additionally, such compression techniques rely on clot formation, which can be delayed until anticoagulants used in vascular therapy procedures (such as for heart attacks, stent deployment, non-optical PTCA results, and the like) wear off. The anticoagulants may take two to four hours to wear off, thereby increasing the time required before completion of the manual compression procedure.

The manual compression procedure is uncomfortable for the patient and frequently requires analgesics to be tolerable. Moreover, the application of excessive pressure can at times totally occlude the underlying blood vessel, resulting in ischemia and/or thrombosis. Following manual compression, the patient typically remains recumbent from four to as much as twelve hours or more under close observation to assure continued hemostasis. During this time, renewed bleeding may occur, resulting in blood loss through the tract, hematoma and/or pseudo-aneurysm formation, as well as arteriovenous fistula formation. These complications may require blood transfusion and/or surgical intervention.

The incidence of complications from the manual compression procedure increases when the size of the introducer sheath grows larger, and/or when the patient is anticoagulated. The compression technique for arterial closure can be risky, and is expensive and onerous to the patient. Although the risk of complications can be reduced by using highly trained individuals, dedicating such personnel to this task is both expensive and inefficient. Nonetheless, as the number and efficacy of translumenally performed diagnostic and interventional vascular procedures increases, the number of patients requiring effective hemostasis for a vascular puncture continues to increase.

Vascular closure devices were introduced to reduce the time to hemostasis, enable early ambulation and improve patient comfort. Initially, devices focused on technologies involving a suture or collagen plug. These technologies close the hole or puncture site, however, they often leave an intravascular component in the vessel which can cause complications and result in residual bleeding or tract ooze. Some amount of slow and steady tract bleeding is a common occurrence. This bleeding usually requires direct management by a trained health care professional until it is completely stopped. Anticoagulant medications typically given to catheterized patients can exacerbate bleeding and may require management with manual compression until the medication wears off.

BRIEF SUMMARY OF THE INVENTION

This application is directed to a vessel closure device for delivering rapid hemostasis at a puncture site in a wall of a blood vessel. The vessel closure device can include an intravascular anchor having one or more suture attachment points, an extravascular cap having a lumen, a sealant, and a suture connected to at least one of the one or more suture attachment points of the intravascular anchor and threaded through the lumen of the extravascular cap. Each of the intravascular anchor, extravascular cap, sealant, and suture can be formed of bioabsorbable materials.

The present invention relates to a vessel closure device for delivering immediate hemostasis at a puncture site in a wall of a blood vessel, the closure device includes an intravascular anchor comprising one or more suture attachment points, an extravascular cap having a lumen, a sealant, and a suture connected to at least one of the one or more suture attachment points of the intravascular anchor and threaded through the lumen of the extravascular cap and through the sealant to connect the intravascular anchor to the extravascular cap and to the sealant. Each of the intravascular anchor, extravascular cap, sealant, and suture are formed of bioabsorbable materials.

The present also relates to a vessel closure device having one or more of an elongate body having a flexible member and a keel (optionally with a plurality of ribs radiating from the keel to a raised edge of the elongate body), an extravascular cap being formed of an elastomeric material, the sealant being formed of polyethylene glycol (PEG), the suture having a distal suture portion and a proximal suture portion, the diameter of the lumen of the extravascular cap being smaller than the diameter of the distal suture portion, the intravascular anchor being formed or having a material selected from Polyglycolic acid (PGA), Poly-L-Latic acid (PLLA), Polycaprolactone (PCL), Poly-DL-lactic acid (PDLLA), Poly trimethylene carbonate (PTMC), and Poly para-dioxanone (PPDO), and the sealant can expand up to 4 times its original size when introduced to fluids.

A vessel closure device for delivering immediate hemostasis at a puncture site in a wall of a blood vessel, the closure device including an intravascular anchor having one or more suture attachment points, an extravascular cap having a lumen, a sealant having a lumen, and a suture connected to at least one of the one or more suture attachment points of the intravascular anchor and threaded through the lumen of the extravascular cap and through the lumen of the sealant to connect the intravascular anchor to the extravascular cap and to the sealant. The suture can include a proximal suture portion and a distal suture portion, wherein the distal suture portion has a diameter greater than a diameter of the lumen of the extravascular cap. The distal suture portion can create an interference fit to lock the extravascular cap over the puncture site, and each of the intravascular anchor, extravascular cap, sealant, and suture are formed of bioabsorbable materials.

The present also relates to a vessel closure device having one or more of the extravascular cap is formed of flexible material, the suture being a braided suture, the sealant is threaded onto the suture at a location proximal to the extravascular cap, the sealant when activated locks the extravascular cap in place and coagulates an access tract of the puncture site providing immediate hemostasis, the intravascular anchor having an elongate body, a raised keel located on a central axis of the elongate body and spanning the length of the elongate body (optionally including one or more suture attachment points), and the sealant being formed of polyethylene glycol (PEG).

The present invention also relates to an intravascular anchor for a vessel closure device for delivering immediate hemostasis at a puncture site in a wall of a blood vessel, the intravascular anchor including an elongate body comprising a flexible membrane for conforming to the wall of the blood vessel, a keel having one or more suture attachment points, wherein the keel is an elongate member centrally located along a central axis of the elongate body, and wherein the intravascular anchor comprises a bioabsorbable material selected from Polyglycolic acid (PGA), Poly-L-Latic acid (PLLA), Polycaprolactone (PCL), Poly-DL-lactic acid (PDLLA), Poly trimethylene carbonate (PTMC), and Poly para-dioxanone (PPDO).

These and other objects and features of the present invention will become more fully apparent from the following description and appended claims, or may be learned by the practice of the invention as set form hereinafter.

BRIEF DESCRIPTION OF THE DRAWINGS

A description of various aspects and features of the invention will be rendered by reference to various representative embodiments thereof illustrated in the appended drawings. It is appreciated that these drawings depict only typical embodiments of the invention and are therefore not to be considered limiting of its scope.

FIGS. 1A-1C illustrate a delivery system in which a closure device can be implemented according to one example.

DETAILED DESCRIPTION

Figure 1A:
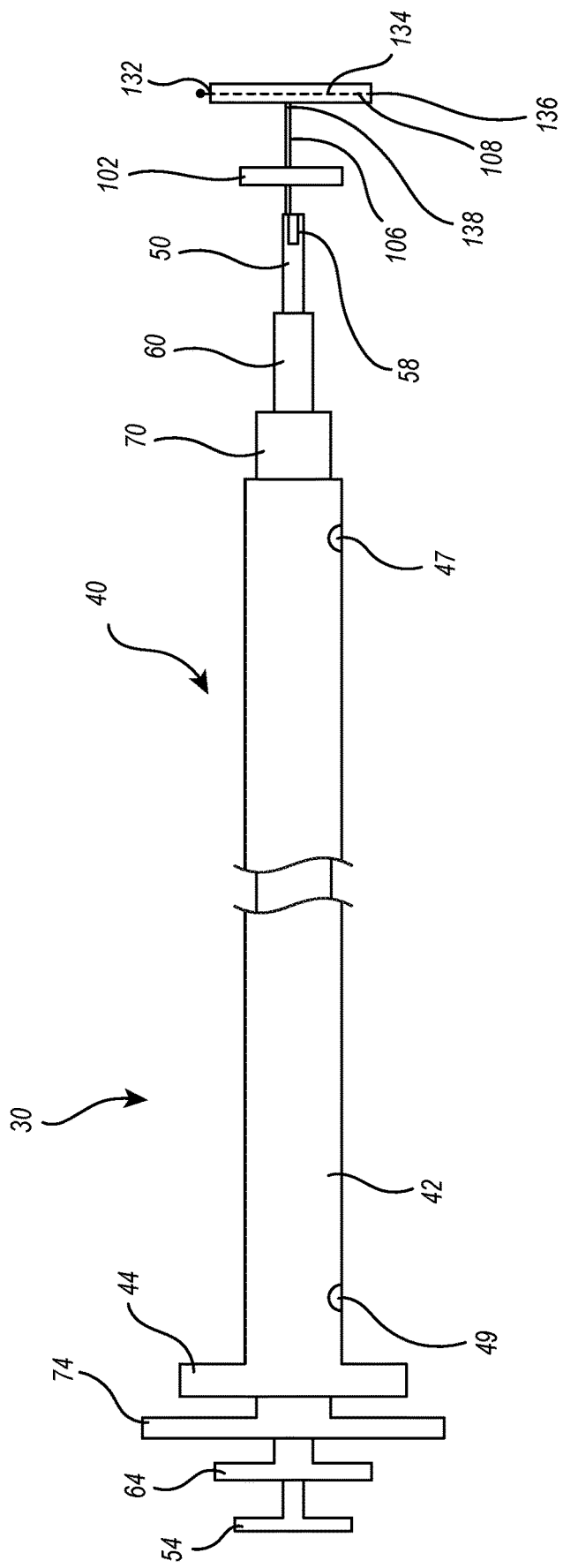

One or more specific embodiments of the present disclosure will be described below. In an effort to provide a concise description of these embodiments, some features of an actual embodiment may be described in the specification. It should be appreciated that in the development of any such actual embodiment, as in any engineering or design project, numerous embodiment-specific decisions will be made to achieve the developers' specific goals, such as compliance with system-related and business-related constraints, which may vary from one embodiment to another. It should further be appreciated that such a development effort might be complex and time consuming, but would nevertheless be a routine undertaking of design, fabrication, and manufacture for those of ordinary skill having the benefit of this disclosure.

One or more embodiments of the present disclosure may generally relate to apparatuses, systems, and methods to provide a closure device or closure implant configured to close an opening formed in tissue. The closure devices or closure implants can be configured to provide immediate or substantially immediate hemostasis at the vessel puncture and delivery of a hemostatic agent in the access tract to eliminate track ooze. The configuration of the disclosed closure devices or closure implants can prevent extravascular components from passing through the puncture site, as well as improved resistance to fracture and possible embolization.

One or more embodiments of the present disclosure may also generally related to apparatuses, systems, and methods used to close an opening, with a portion of the closure device or closure implants temporary remaining within the patient to close the opening and being subsequently degraded, absorbed, or resorbed over a period of time.

While the present disclosure will describe a particular implementation of apparatuses and systems, with associated methods, for removing closing an opening in tissue, it should be understood that any of systems, apparatuses, and methods described herein may be applicable to other uses, including and not limited to closing existing or formed openings in tissue or body lumens in other locations with a patient's anatomy. Additionally, elements described in relation to any embodiment depicted and/or described herein may be combinable with elements described in relation to any other embodiment depicted and/or described herein.

Vessel Closure Delivery System

The present disclosure relates to devices, systems, and methods for closing an opening in a blood vessel. For example, the present disclosure includes an anchor, such as an intravascular anchor formed from, in one configuration, a bioabsorbable, bioresorbable, and/or biodegradable material. The anchor may be passed through an opening defined in a wall of a blood vessel and deployed. The anchor can then be drawn proximally to draw the anchor into contact with a distal side of the blood vessel lumen wall. A closure element, such as an extravascular cap, can then be deployed to close the puncture.

In at least one example, once deployed within a blood vessel, the anchor (and optionally the cap) may degrade, absorb, or resorb in a predetermined amount of time, such as between about 36-72 hours, in less than 48 hours, less than about 36 hours, in a day, less than an hour, or some other amount of time as desired. The rapid degradation, absorption, or resorption of one or more components of the device can allow the anchor, for example, to be left in place after the closure device or closure implant has been deployed by obviating the need for removal of the anchor. By leaving the anchor in place until it degrades, absorbs, or resorbs, damage that may occur by drawing the anchor through the closed puncture and/or the deployed closure element can be reduced or eliminated.

In addition, the degradation, absorption, or resorption time of the anchor may fall within the time frame of the action of an anti-thrombotic medication being used in conjunction with the treatment of a patient. Accordingly, the closure device or closure implant of the present disclosure may reduce the risk of formation of intra-arterial clots associated with the closure of the blood vessel puncture site.

While reference has been made to the anchor remaining in the blood vessel and degraded, absorbed, or resorbed by the patient's body, it will be understood that in other configurations the anchor may be deployed and subsequently removed once sufficient closure of the puncture has occurred.

Figure 1B:
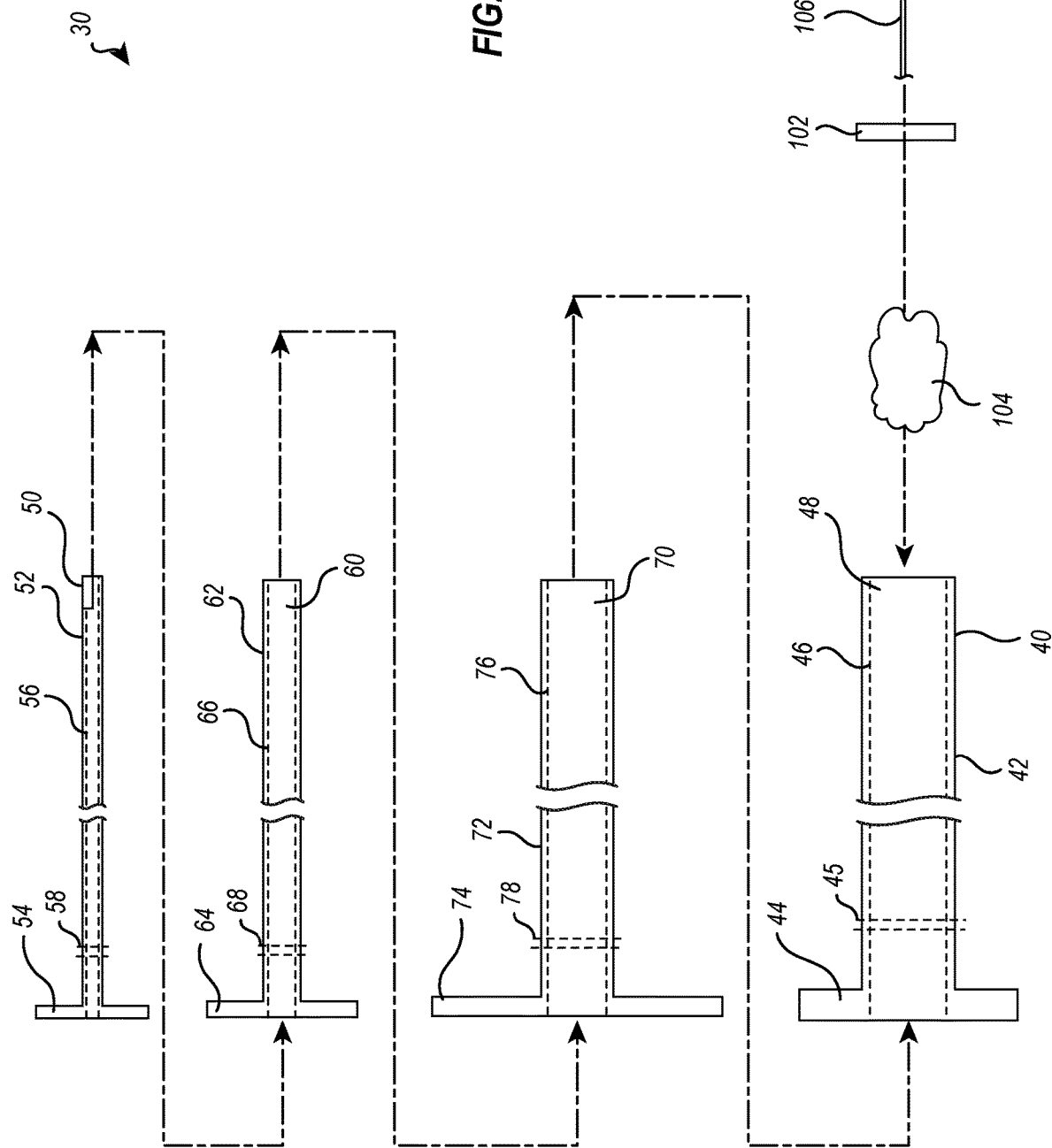

Reference is now made to FIGS. 1A-1B, which illustrates a closure device delivery system or closure implant delivery system 30 according to one example. As shown in FIGS. 1A-1B, the delivery system 30 may include a delivery sheath 40 with a nested set of actuators 50, 60, and 70 that are configured to cooperate to deploy a closure device or closure implant 100 including an anchor 108, such as an intravascular "foot" or anchor, a closure element, such as a cap 102 (see FIGS. 2-4), a fluid-blocking component 104, such as a sealant (see FIGS. 2-4) (the term fluid-blocking component and sealant will be used interchangeably herein), and a suture element 106. For instance, the actuator 50 can be used to deploy the anchor 108, the actuator 60 can be used to deploy the cap 102, and the actuator 70 can be used to deploy the fluid-blocking component 104. In at least one example, the delivery sheath 40 is configured to house the anchor 108, the cap 102, and the fluid-blocking component 104 while the actuators 50, 60, and 70 are configured to deploy the anchor 108, the cap 102, and the fluid-blocking component 104, respectively from the delivery sheath 40. The exemplary delivery sheath 40, actuators 50, 60, and 70, anchor 108, and closure device 100 of FIG. 1A will be discussed in more detail with reference to FIG. 1B.

Figure 1D:
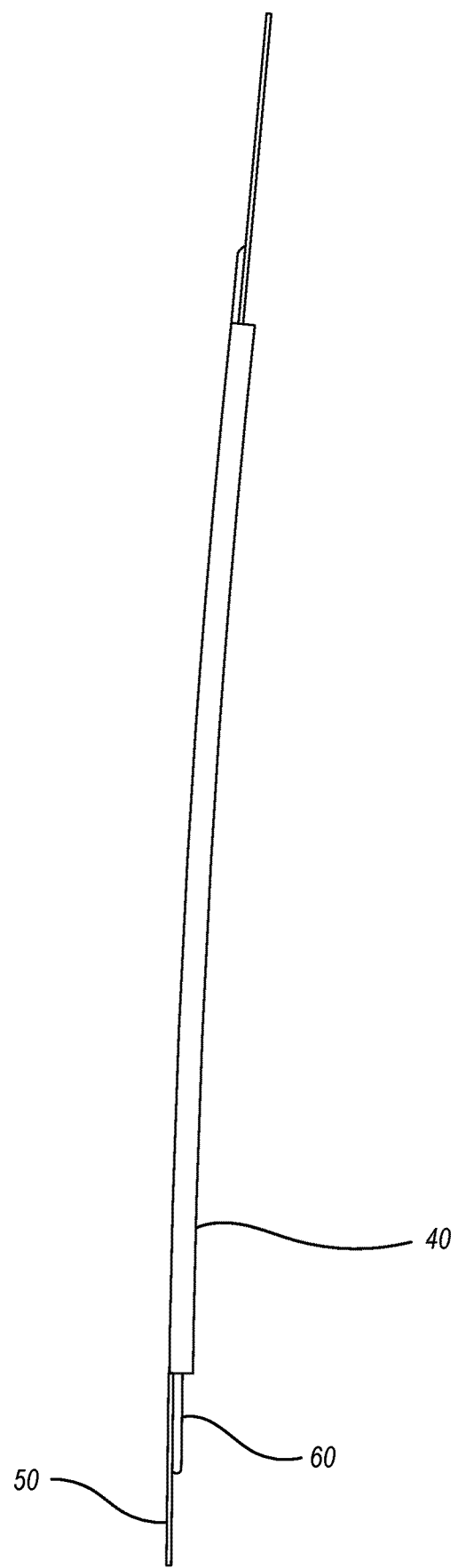
FIG. 1D illustrates an alternate delivery system for deploying the closure device according to the present invention.
Figure 1E:
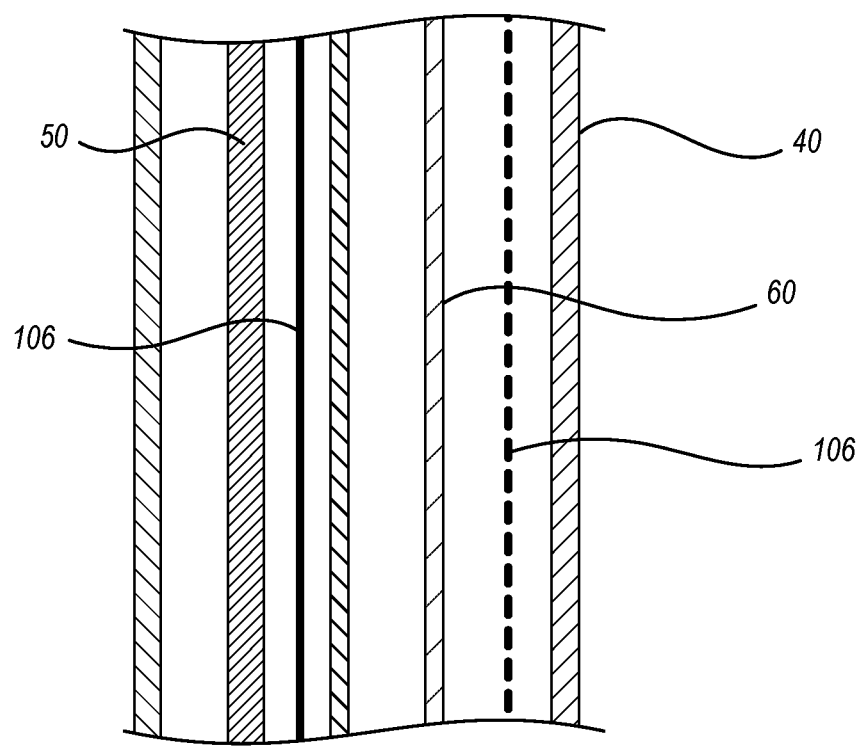
FIG. 1E illustrates a partial cross-sectional view of the alternate delivery system of FIG. 1D.

While the set of actuators 50, 60, and 70 are illustrated as being coaxially disposed within the delivery sheath 40, the actuators 50, 60, and 70 can be non-coaxially disposed in the delivery sheath 40, such as illustrated in FIGS. 1D and 1E where the actuator 50 is disposed to a side of the actuator 60. Additionally, returning to FIGS. 1A-1B, while the following discussion provides one manner by which specific actuators can be used to deploy the anchor 108, the cap 102, and the fluid-blocking component 104, it will be understood by those skilled in the art that one of the actuators 50, 60, and 70 can deploy any combination of the anchor 108, the cap 102, and the fluid-blocking component 104 in any order or sequence. For instance, while the actuator 60 can deploy the cap 102 and the actuator 70 can deploy the fluid-blocking component 104, in other configurations one of the actuators can be eliminated, such as for example the actuator 70, and the actuator 60 can deploy the cap 102, advance the fluid-blocking component 104 toward the cap 102, and deploy the fluid-blocking component 104 through a combination of distal and/or proximal movement in relation to the anchor 108. In other configurations, the delivery system 30 can include two or more actuators, such as two or more of the actuators 50, 60, or 70, to delivery/deploy the anchor 108, the cap 102, and the fluid-blocking component 104. It is also possible for other combinations of deployment functions to be performed by other individual or combination of actuators. The one or more lumens of the one or more actuators 50, 60, or 70 can include one or more valves or seals 58, 68, and 78, and the delivery sheath 40 can also include one or more valves or seals 45, to prevent blood flowing from the ends of the delivery sheath 40 and the actuators 50, 60, and 70.

FIG. 1B illustrates an exploded view of the delivery system 30. As shown in FIG. 1B, the delivery sheath 40 includes an outer housing 42 and a handle or grip portion 44. Each of the actuators 50, 60, and 70 include, respectively, a shaft or housing portion 52, 62, 72, a handle or grip portion 54, 64, and 74, and distal ends that can cooperate with, respectively, the anchor 108, the cap 102, and the fluid-blocking component 104. For instance, the actuator 50 can include a notch 58 (FIG. 1A) to receive the suture 106 and optionally a portion of the anchor 108. An interior lumen 46 is defined in the outer housing 42 that is configured to receive the actuators 50, 60, and 70 in such a manner as to allow the actuators 50, 60 and 70 to be extended from and retracted within a distal end 48 of the outer housing 42. Each actuator 50, 60 and 70 also includes, respectively interior lumens 56, 66, and 76 to allow for translation of the actuators 50, 60, and 70, either independently or in combinations of 2 or more of the actuators, and the delivery sheath 40. Translation distance of the actuators 50, 60, and 70 can be controlled through contact between adjacent handle or grip portions 44, 54, 64, and 74. For instance, the grip portion 44 can limit distal movement of each of the grip portions 54, 64, and 74 associated with the actuators 50, 60, and 70, while grip portion 74 can limit distal movement of each of the grip portions 54, and 64 and the grip portion 64 can limit movement of the grip portion 54. In this way, over translation of individual actuators is limited and the anchor 108, cap 102, and fluid-blocking component 104 can be effectively deployed to access and close a tissue opening.

While reference is made to the handle or grip portions limiting actuator translation, it is understood that other approaches can be used for controlling translation. For instance, complementary structures can be formed in the housings and the interior lumens to limit translation. In another configuration, the handle or grip portions are combined into a single handle assembly having different actuation controls, such as switches, knobs, sliders, etc. to allow independent or combined movement of one or more of the actuators 50, 60, and 70.

In another configuration, as illustrated in FIG. 1C, an interior lumen 46' can include a first portion 46A' configured to receive the shaft portion 54' of the actuator 50' while a second portion 46B' of the interior lumen 46' can be configured to receive a distal end 54A' of the shaft portion 54' having the interior lumen 56'. More specifically, the second portion 46B' of the interior lumen 46' may have a larger width aspect than the width aspect of the first portion 46A'. The width aspects of the first portion 46A' and the second portion 46B' can be the diameters thereof or other cross-sectional profiles that are generally transverse to a center axis C of the delivery sheath 40'. For ease of reference, the center axis C of the delivery sheath 40' will be referenced in describing the position and movement of the other components described herein. In the illustrated example, the interior lumen 46' may transition from the smaller diameter of the first portion 46A' to a second larger diameter of the second portion 46B' at a shoulder 46C'.

Such a configuration can allow the actuator 50' to translate axially relative to the delivery sheath 40' within a desired range of motion. In particular, the handle portion 52' can translate within the second portion 46B' of the interior lumen 46' to advance the shaft portion 54' within the outer housing 42' and in relation to the handle or grip port 44' to thereby move the distal end 54A of the shaft portion 54' relative to the distal end 42A of the outer housing 42'. Interaction between the handle portion 52' and the shoulder 46C' can help ensure the distal end 54A' does not extend beyond a desired position within the outer housing 42.

In the illustrated example, the first portion 46A' may also be configured to receive the anchor 108 and the cap 102 proximally of the distal end 54A' of the shaft portion 54'. Accordingly, as the distal end 54A' of the shaft portion 54' is advanced toward the distal end 42A' of the outer housing 42', the distal end 54A' of the shaft portion 54' can engage the anchor 108 and/or the cap 102 to move the anchor 108 and/or the cap 102 distally from the outer housing 42.

Returning to FIG. 1A, the anchor 108 can be configured to move from a pre-deployed state having a pre-deployed width aspect to a deployed state having a deployed width aspect. The deployed width aspect may be greater than the pre-deployed width aspect. The anchor 108 can have any configuration that allows for this. In the illustrated example, anchor 108 is configured to rotate or be rotated between the pre-deployed state and the deployed state. In other examples, portions or all of the anchor 108 may be configured to unfold from a configuration have a pre-deployed width aspect to a deployed state having a greater width aspect. For example, one or more arms or wings may be configured to unfold and fold about a plurality of pivot points, hinges, living hinges, bending locations, preferential bending location, combinations or modifications thereof.

As shown in FIG. 1A, the anchor 108 includes wing members 132, 134 that define a major axis 136 of the anchor 108. The anchor 108 can further include one or more holes or eyelets 138 disposed along a length of the anchor 108. The holes or eyelets 138 can be located at a position that causes the anchor 108 to rotate when a force acting initially parallel to the major axis 136 is exerted on the eyelets 138. Such a configuration can allow the anchor 108 to move from a state in which the major axis 136 is aligned with the central axis C to a state in which the major axis 136 is oriented more obliquely to the central axis C, such as generally perpendicular to the central axis C.

This rotation can be accomplished by applying a distally acting force on the anchor 108 to move the anchor 108 out of the outer housing 42 and then a proximally directed force to the anchor 108 by way of the interaction between the suture 106 and the eyelets 138. In at least one example, the distally acting force applied to the anchor 108 can be provided from the actuator 50 while the proximally directed force can be applied by way of the suture element 106. The anchor 108 can thus be used to position the delivery system 30 for deployment of the closure element 102.

In one embodiment, the closure element 102 may be configured to close an opening in a lumen of a blood vessel as well as at least partially obstruct a tissue tract leading from an external surface of the tissue to the lumen. The shape of the closure element 102 may be configured to be housed within the interior lumen 46 (or one of the other lumens of the actuators 50, 60, 70). For example, the closure element 102 may conform to the shape of the interior lumen 46. In one embodiment, the closure element 102 may be generally cylindrical in shape prior to being deployed from the delivery sheath 40 in which portions of the closure element 102 are at least partially wrapped around or curved towards a central portion of the closure element 102, whether or not those peripheral portions curve proximally, distally, or transverse to a direction of deployment of the closure element 102 toward the previously deployed anchor 108. Once deployed from the delivery sheath 40, at least a portion of the closure element 102 may be at least partially deformable to conform to any desired shape of the vessel wall to close an opening in a blood vessel and/or the tissue tract leading to the lumen opening.

As shown, the suture element 106 can loop through the anchor 108 such that the suture element 106 passes through or near the closure element 102, and extends proximally into or beyond the handle portion 52 of the actuator 50'. In at least one example, the free end of the suture element 106 passes through separate portions or channels of the closure element 102. The suture element 106 can be extended from the closure element 102 and into the actuator 50 by way of the interior lumen 56.

Generally, the structures and components of the delivery system 30 can be formed of polymers, metals, alloys, combinations or modifications thereof. For instance, by way illustration only, the delivery sheath and the actuators can be formed from metal hypotubes, polymer tubes, composite tubes have a multilayer configuration, or other tubular structures optionally including reinforcing members or braids. The delivery sheath and the actuators can range in outside diameter from about 6 F to about 10 F, from about 2 mm to about 4 mm, from about 2 mm to about 3.33 mm, or other sizes as known to those skilled in the art.

Vessel Closure Device

Figure 2A:
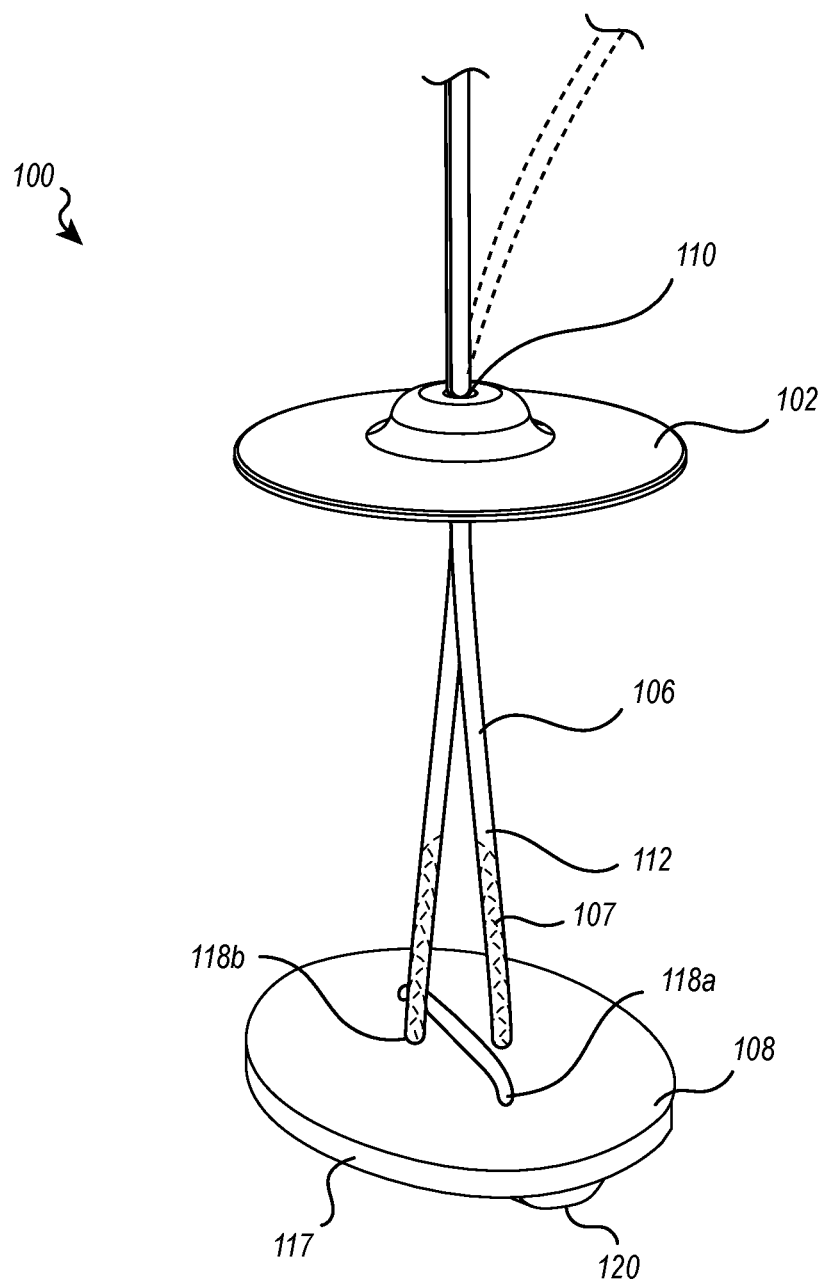
FIGS. 2A and 2B illustrate example embodiments of a closure device.
Figure 2B:
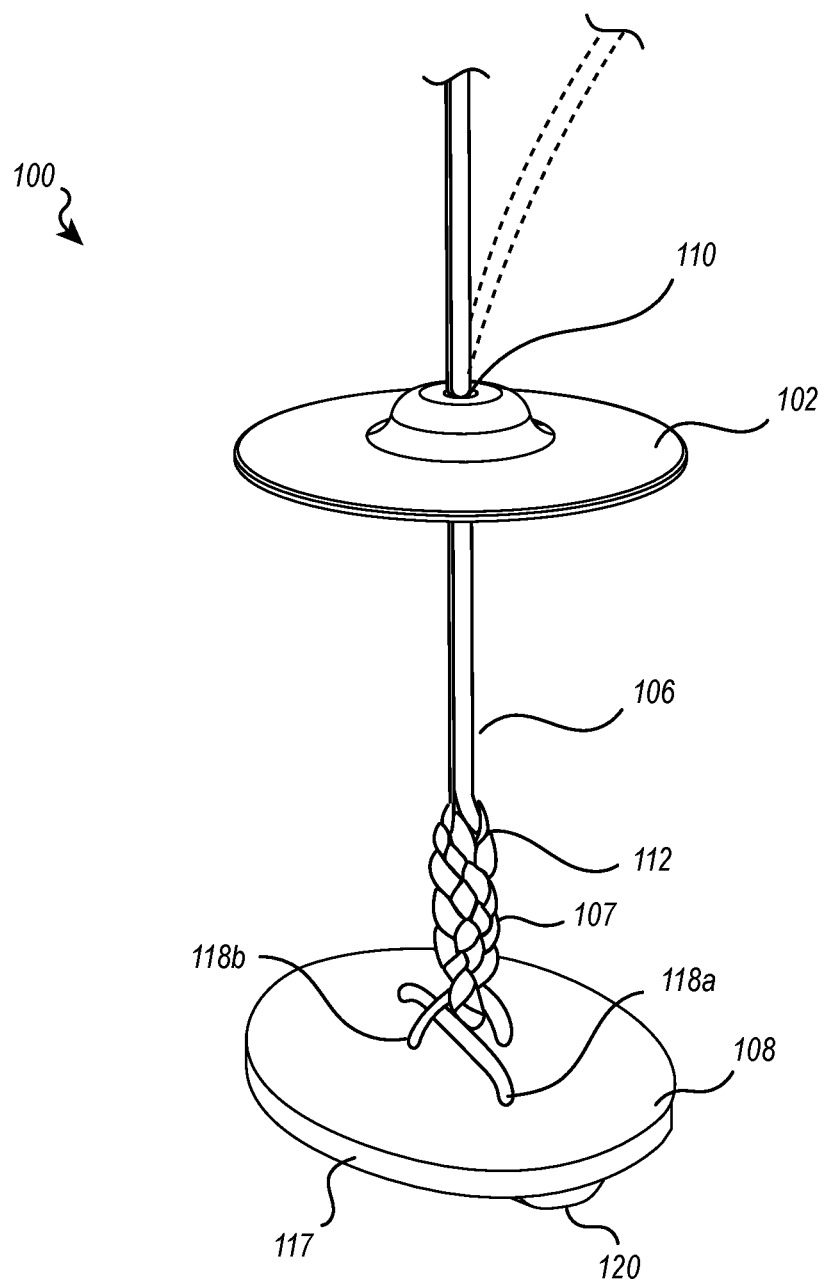

FIGS. 2A-2B illustrates an example of the closure device 100. In this particular configuration, the closure device 100 can be a fully bioabsorbable vessel closure implant including intravascular and extravascular components. The extravascular components can include an extravascular cover or cap 102 (hereinafter "extravascular cap" or "cap") and a second extravascular component or fluid-blocking component 104, such as a bioabsorbable sealant (see FIGS. 4-6B), which can also be collectively referred to as a closure element. The intravascular components can include an intravascular foot or anchor 108 and a suture 106, both of which can be bioabsorbable. As mentioned above, in other configurations, the intravascular foot or anchor 108 can be temporarily deployed, with the extravascular components being fully bioabsorbable (such as through degradation, absorption, and/or resorption).

The extravascular cap 102 can be made from bioabsorbable materials and be of sufficient size and geometry to prevent it from passing through the punctured access site 18 at the surface of the blood vessel 10. The size and geometry of the extravascular cap 102 can significantly increase patient safety by preventing extravascular components from passing through the access site 18 during or after deployment. The cap 102 can have a diameter from about 1 mm to about 10 mm, from about 3 mm to about 8 mm, from about 4 mm to about 5 mm, or other size based upon the specific dimensions of the access site 18 so that the cap 102 does not pass through the access site 18.

The cap 102 can be of low profile and made from a biodegradable material having desired flexibility to conform to the patient's access site anatomy (especially in vessels with significant calcification present) and provide more effective sealing than would rigid materials. The cap can be deployed through a small catheter access tissue tract 22 and placed on top of the vessel 10 as the primary extravascular seal.

Turning to FIGS. 2A-3B, illustrated is one configuration of the cap 102. As illustrated, the cap 102 can have a generally circular disk shape, though in other embodiments, the shape of the cap 102 can be interrupted (e.g. star-shape) which can impart the cap 102 with increased flexibility to allow it to conform to the access tract 22 which is typically narrow. The cap 102 can include a medial portion 113 which may be raised relative to the surrounding surface 111 of the cap 102. The medial portion 113 can have a thickness of about 0.050 mm to about 5 mm, from about 0.10 mm to about 2 mm, from about 0.10 mm to about 0.5 mm, or various other thicknesses. The cap surface 111 can include relief cuts 115 which may provide for increased cap flexibility and conformance to the access tract 22 above the vessel 10. The relief cuts 115 can extend to a longitudinal axis of the cap 102, inclined, curved, non-linear, combinations or modifications thereof. Alternatively, or in addition to the relief cuts 115, a relief cut 115a can have a generally circular form disposed around the medial portion 113, such as to circumscribe, surround, or encircle all or a portion of the medial portion 113. The relief cut 115a can modify the flexibility of surface 111 to improve conformance to the tract and resist entry to the vessel. The cap 102 can have a mass ranging from about 4.0 mg to about 10.0 mg (for 4 mm to about 6 mm diameter cap). With a lower overall mass, less force is used to hold the cap 102 in place between the frictional engagement between the cap 102 and the suture 106. This results in smaller overall system, thereby making positioning within the patient simpler with reduced overall impact on the patient's recovery.

The access tract 22 (see FIGS. 4-6B) is typically size restricted, circular, and formed at an angle in relation to the vessel wall. The cap 102 can be configured to slide down a delivery system 30 through the access tract 22 and be deposited on top of the artery or vessel 10. The suture 106 can then be pulled to tension the cap 102 and intravascular anchor 108 towards each other to seal the access site 18. The cap 102 can include a lumen 110 in the medial portion 113 through which the suture 106 can be threaded to attach the suture 106 to the intravascular anchor 108. The lumen 110 can have a diameter ranging from about 0.010" (0.254 mm) to about 0.020" (0.508 mm), from about 0.012" (0.3048 mm)

to about 0.017" (0.4318 mm), or from about 0.014" (0.3556 mm) to about 0.015" (0.381 mm).

Figure 4:
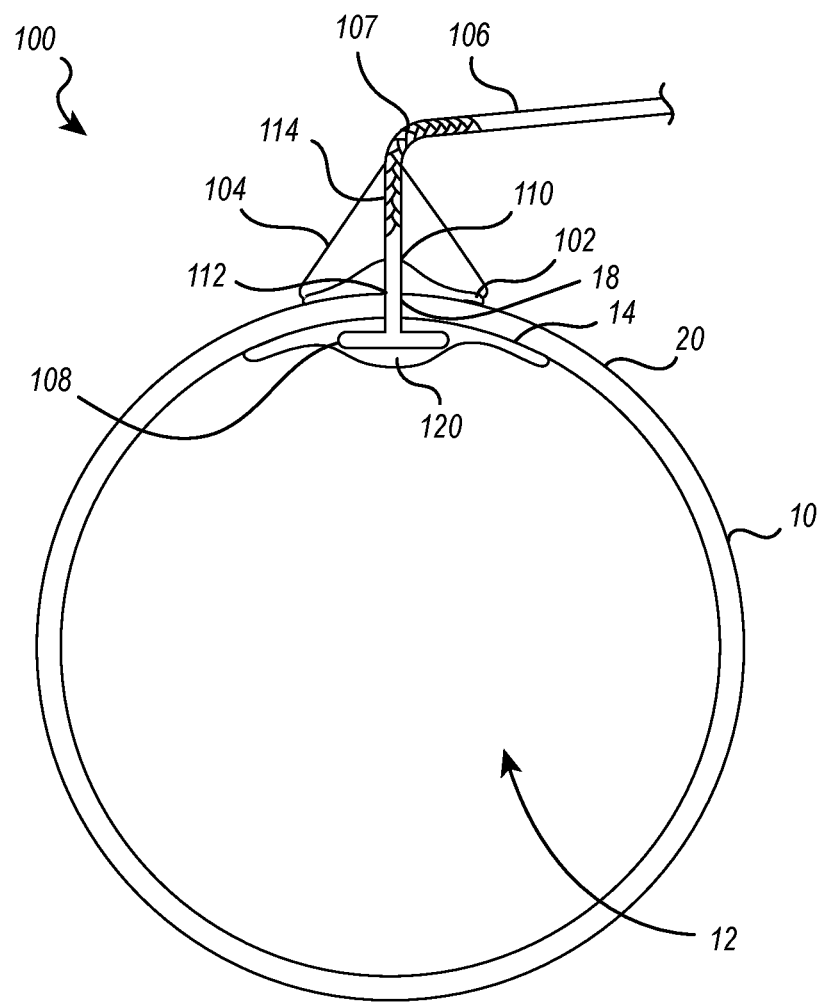
FIG. 4 illustrates a cross-sectional view of a closure device as applied to a vessel.
Figure 5:
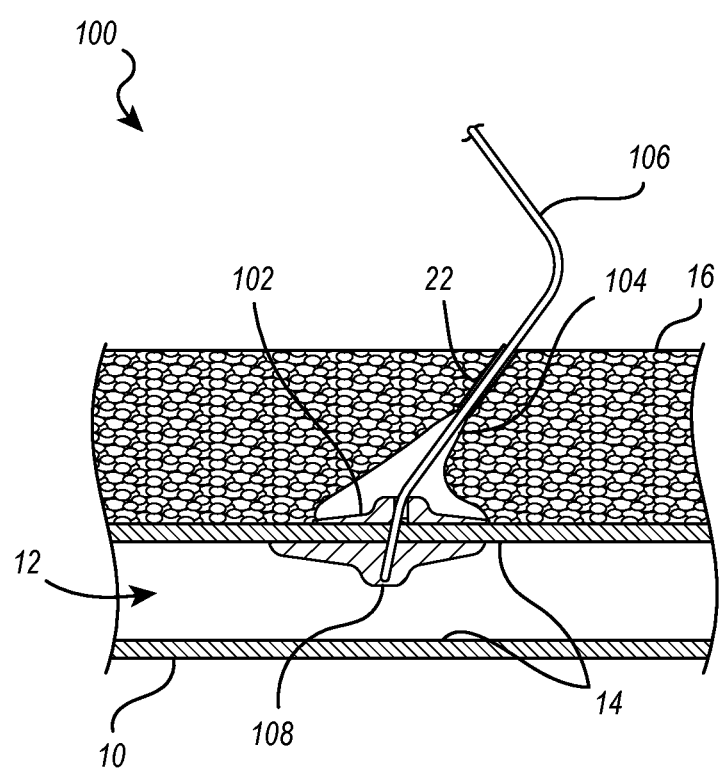
FIG. 5 illustrates a cross-sectional view of a closure device as applied to a vessel through an access tract.
Figure 6A:
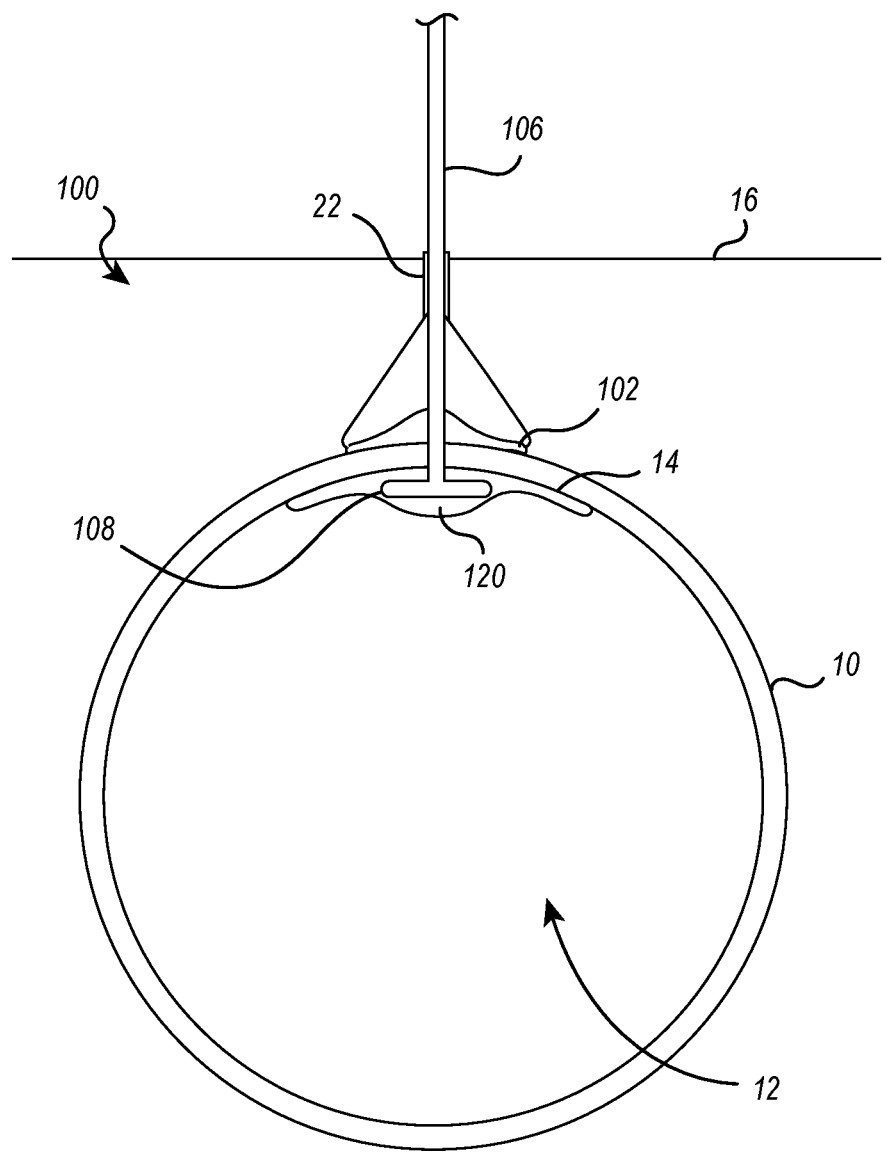
FIGS. 6A and 6B illustrate cross-sectional views of a closure device as applied to a vessel through an access tract.
Figure 6B:
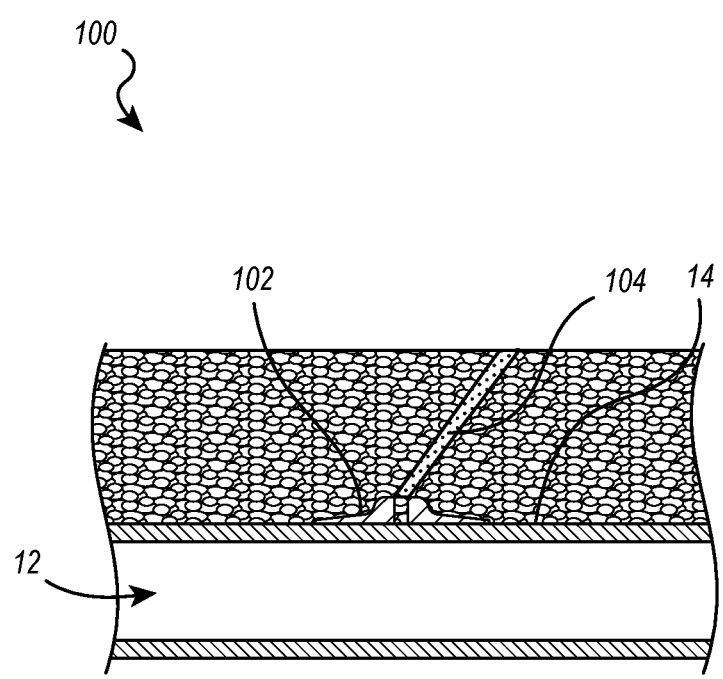
Figure 7A:
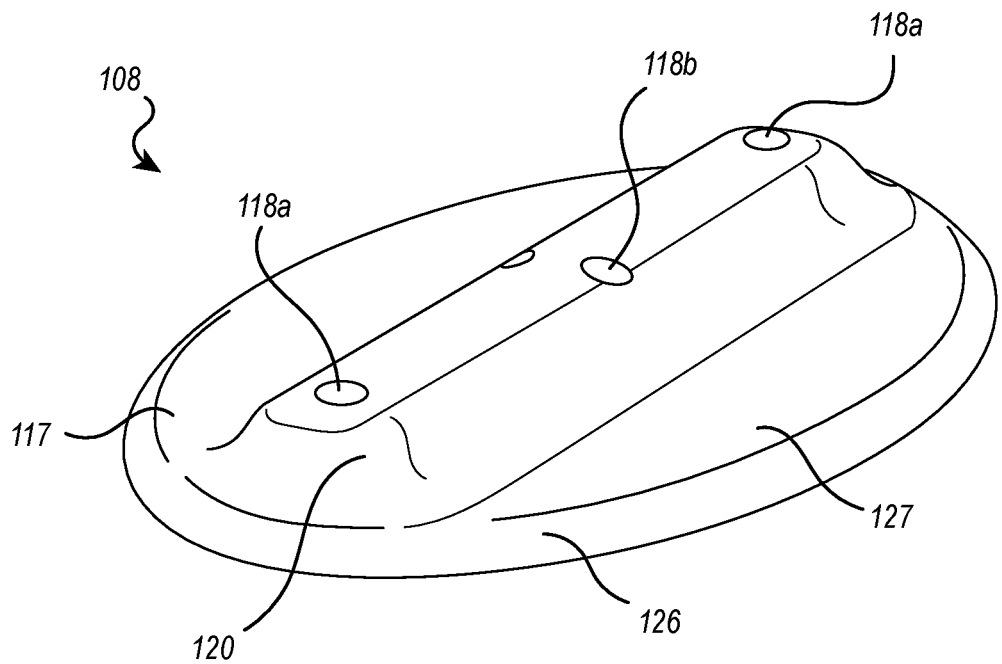
FIGS. 7A-7D illustrate an embodiment of an intravascular anchor of a closure device.
Figure 7B:
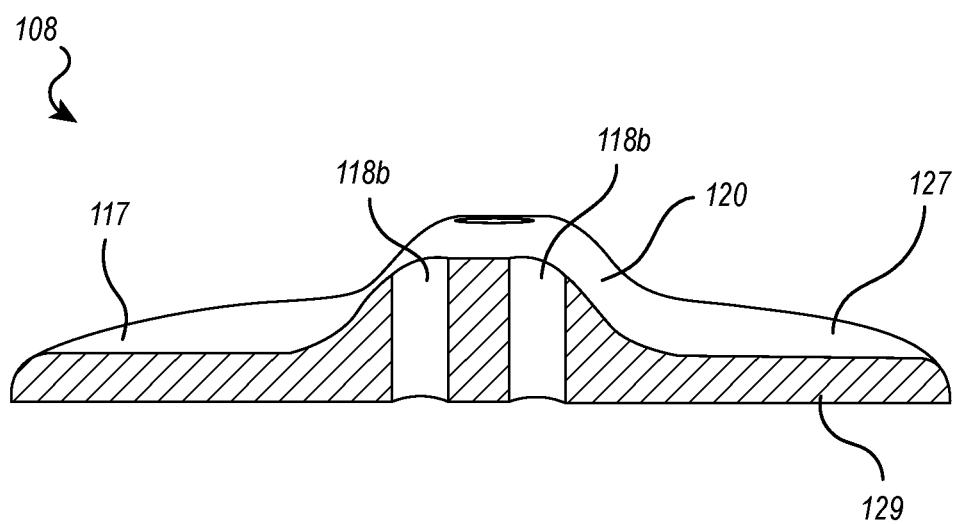
Figure 7C:
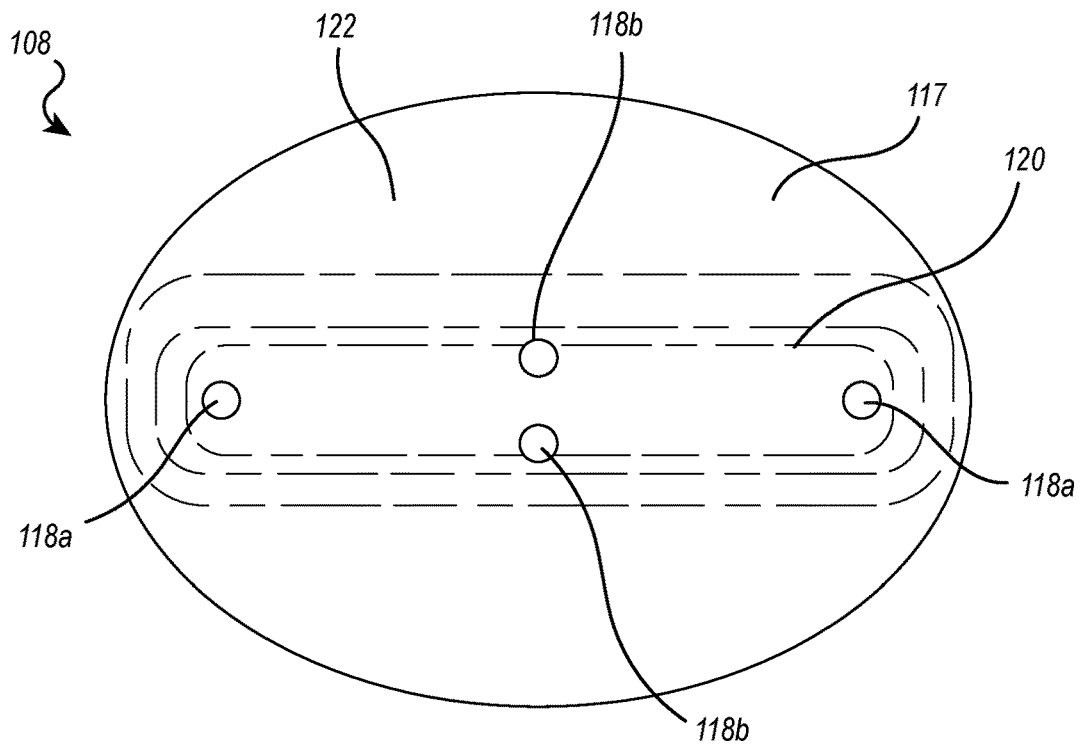
Figure 7D:
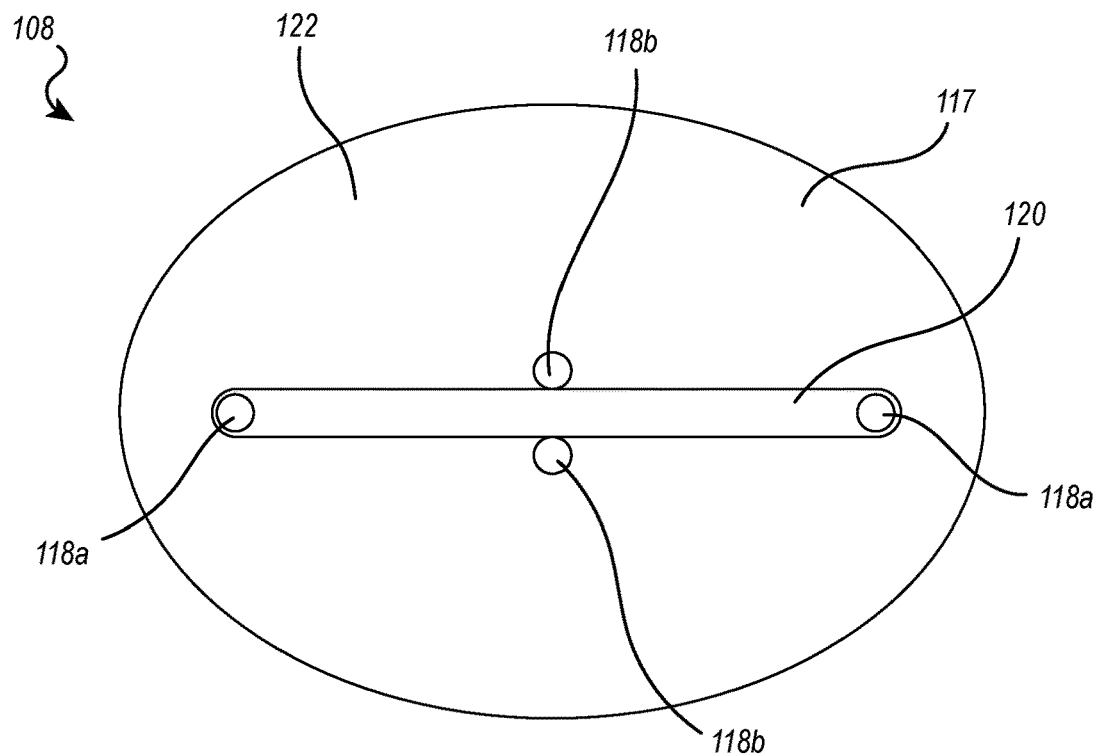
Figure 7E:
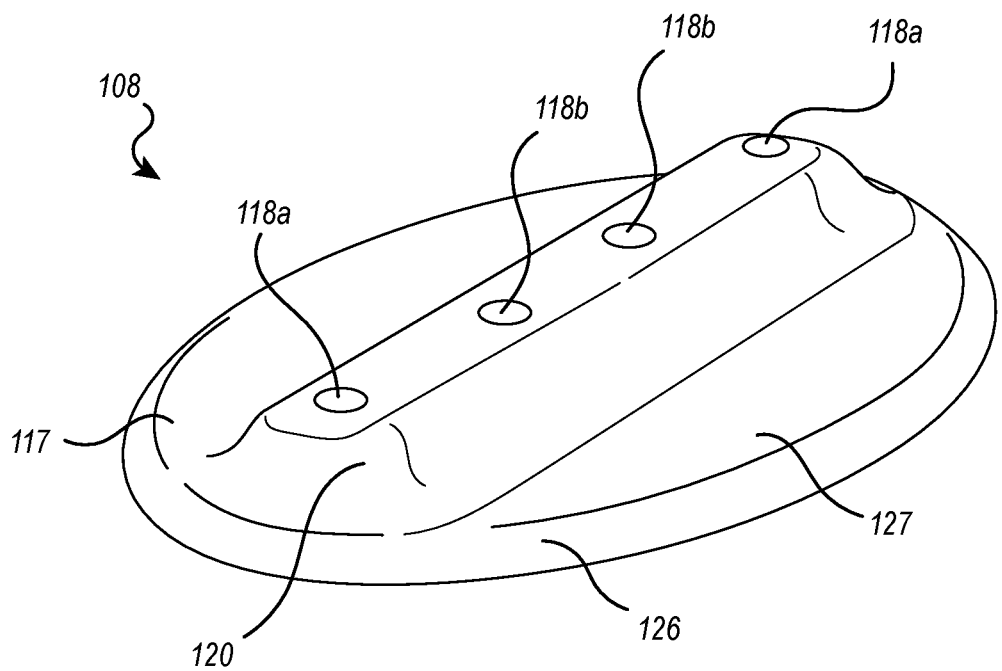
FIGS. 7E and 7F illustrate an alternate embodiment of an intravascular anchor of a closure device.
Figure 7F:
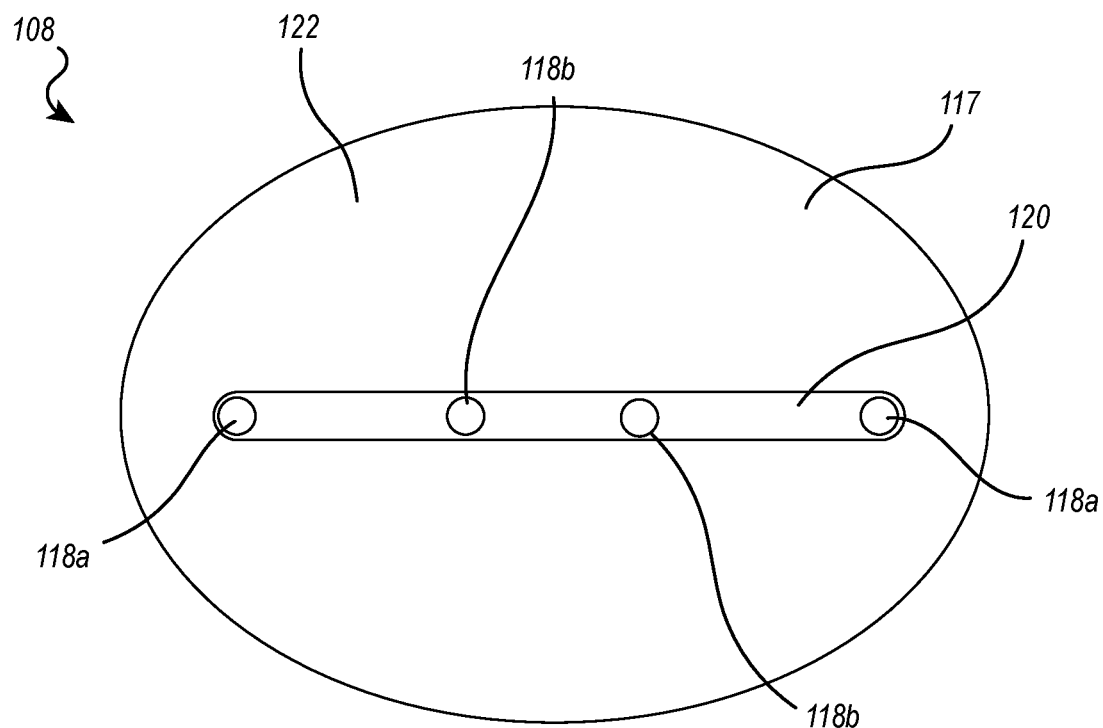
Figure 7G:
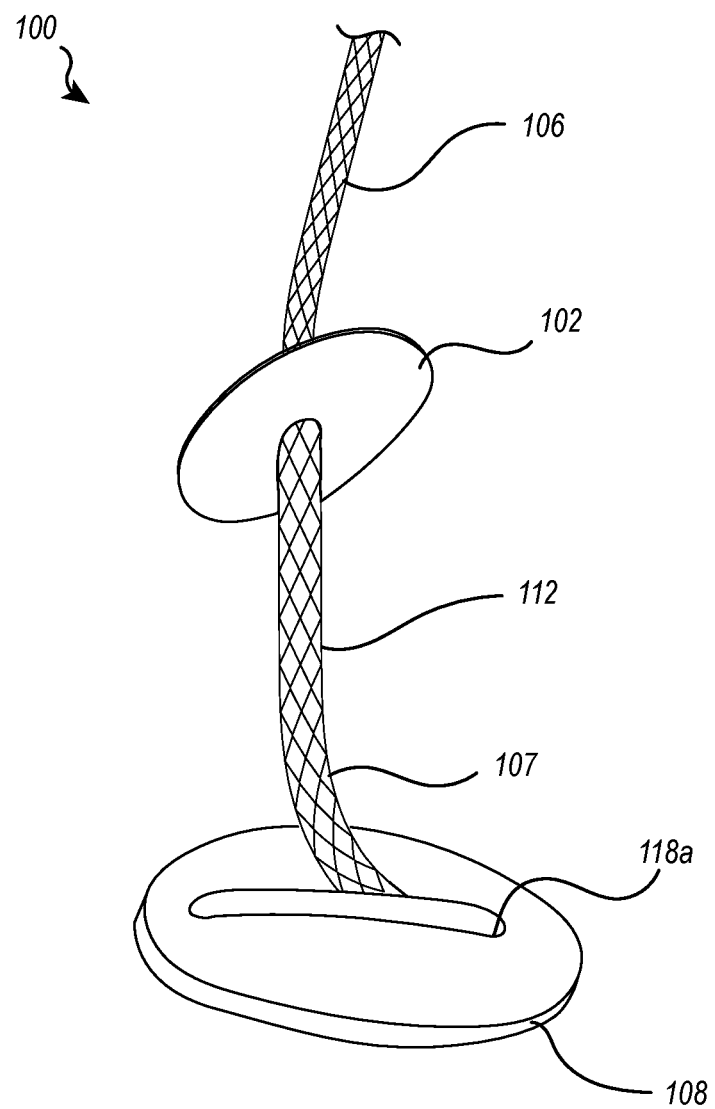
FIGS. 7G and 7H illustrate an alternate embodiment of a closure device.
Figure 7H:
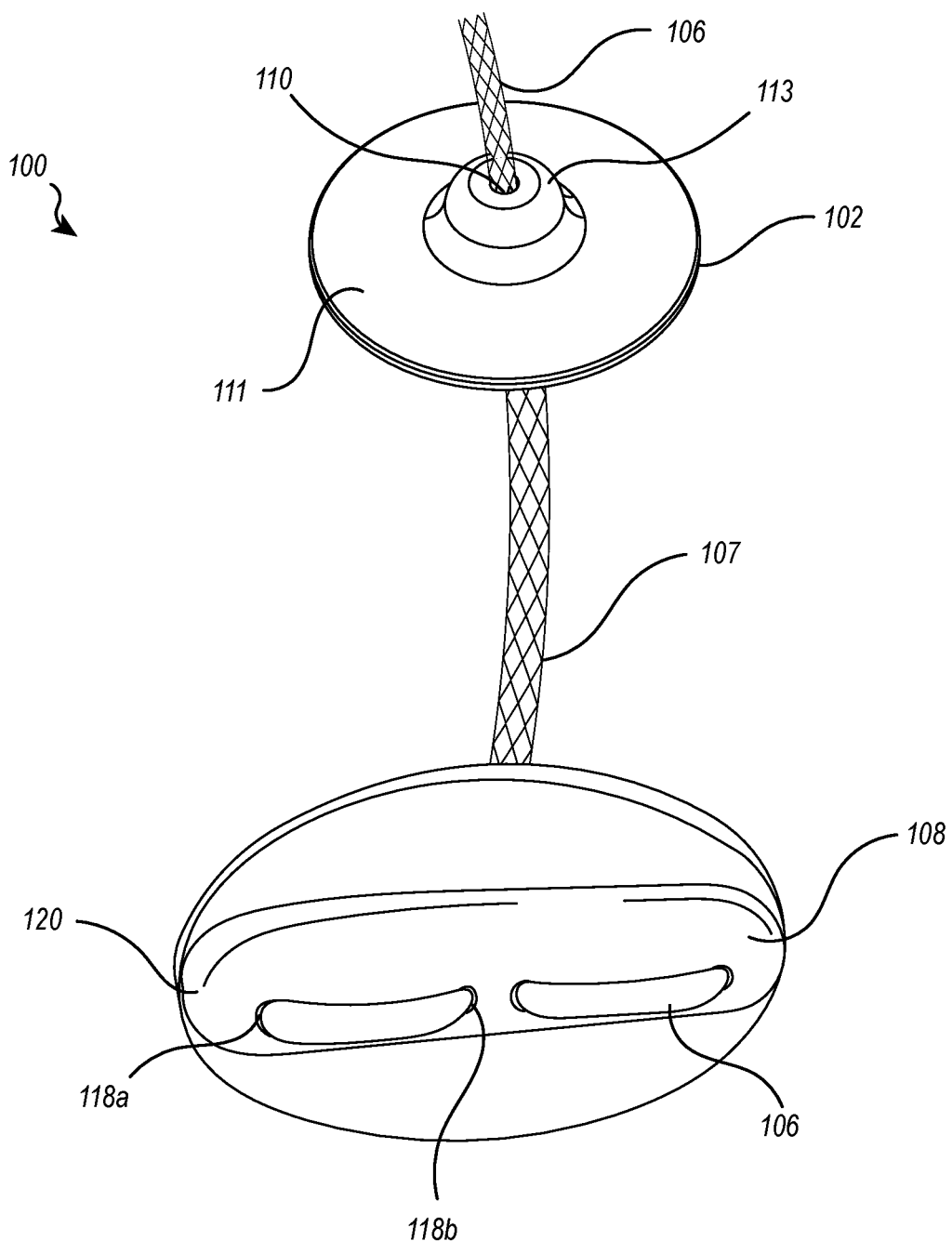

The lumen 110 can be sized to accommodate the suture 106 of a certain diameter. For instance, as illustrated FIGS. 2A-2B, with the suture 106 looped around the anchor 108, two rails or portions of the suture 106 can pass through the lumen 110 and proximally along the delivery device 30. Optionally, portions of the two sutures 106 can be braided together with two suture tails extending proximally from the cap 102. Alternatively, as illustrated in FIG. 4, the suture 106 is looped back on itself and braided into itself to increase a portion of the suture that interference fits or otherwise engages with the lumen wall of the lumen 110, with a single rail extending proximally along the delivery device 30. In still another case, the two sutures 106 can pass through or cooperate with an elongate member 107 (such as another suture portion or braided tubular member), shown in phantom in FIG. 2A-2B, and be braided to and with the elongate member 107, to increase a size of the portion(s) of the suture 106 disposed within the cap 102. One or more elongated member 107 can optionally be inserted into the one or more sutures 106 to increase their dimensions. In each case, i.e., the two adjacent non-braided sutures rails, two adjacent braided suture rails, braided suture and tubular member, or a suture end braided into another portion of the suture after being interwoven through 2 or more holes of the anchor 108, a thick suture portion 112 is formed which can interference fit with the lumen 110, which is narrow relative to the thick suture portion 112, to secure the cap 102 in the desired position. The thick suture portion 112 can have a diameter ranging from about 0.020" (0.508 mm) to about 0.040" (1.016 mm), from about 0.024" (0.6096 mm) to about 0.034" (0.8636 mm), from about 0.028" (0.7112 mm) to about 0.030" (0.762 mm).

The suture 106 can be made of a bioabsorbable material. For example, the suture 106 can be a multifilament or braided absorbable suture, such as those available from VITREX®. In one configuration, the suture is a braided 3-0 suture. It may be advantageous for the suture to have a high tensile strength which can maintain its integrity under the application of from about 3 lbf. to about 6 lbf., although other sutures can accommodate application of forces ranging from about 1 lbf. to about 16 lbf., from about 1 lbf. to about 8 lbf., from about 2 lbf. to about 6 lbf., from about 2.5 lbf. to about 5 lbf., or about 2 lbf.

The cap 102 can be initially positioned on the proximal suture end 116, or the end of the suture 106 which does not have a diameter larger than the diameter of the lumen 110 of the cap 102. When the cap 102 is advanced along the suture 106 to the external vessel surface 20 at the arteriotomy location, the thick suture portion 112 causes an interference that can lock the cap 102 in place, resulting in an immediate dry close.

The interference fit can eliminate the need for the use of a knot to maintain the dry close. Use of a knot can pose serious risk to a patient if the set tension on the suture becomes overtightened. The suture can become stressed by a patient walking or coughing causing the suture to over tension and break. The interference fit may be advantageous because it is knotless and the flexibility of the cap can adapt to force applied to the suture.

Figure 3A:
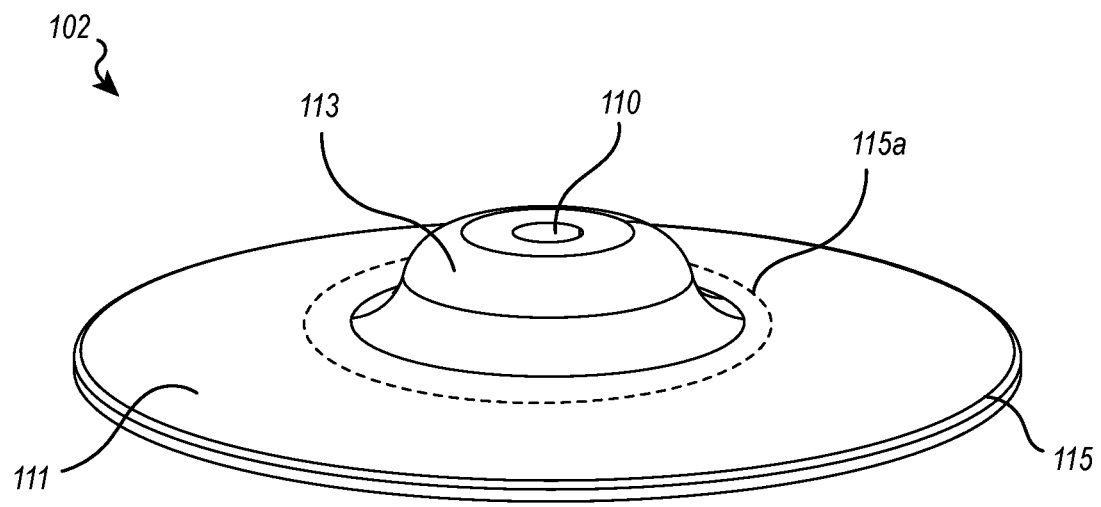
FIG. 3A illustrates an embodiment of a cap of a closure device.
Figure 3B:
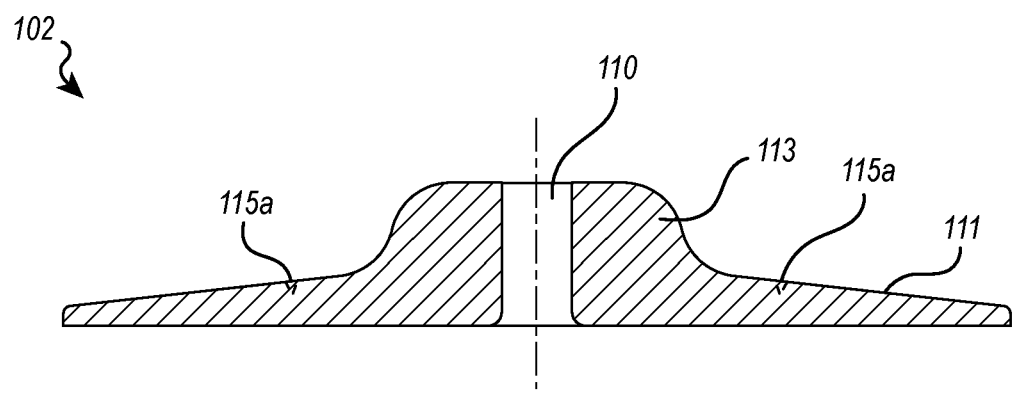
FIG. 3B illustrates a cross-sectional view of the cap of FIG. 3A.
Figure 3C:
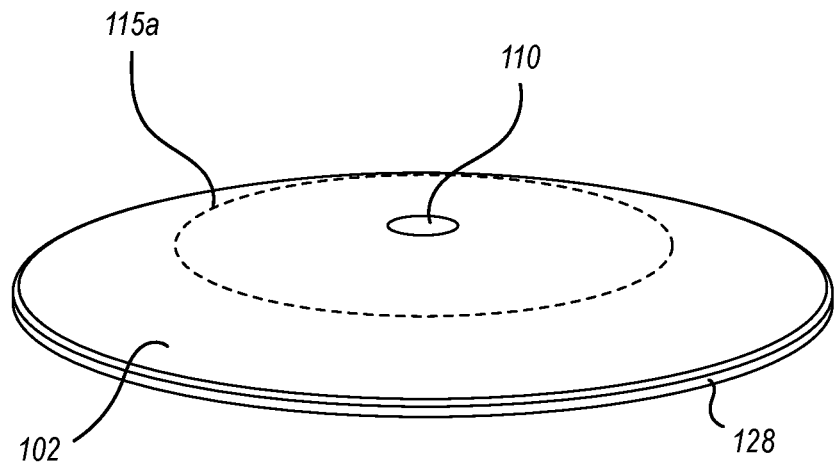
FIG. 3C illustrates the cap of FIG. 3A with an adhesive layer.
Figure 3D:
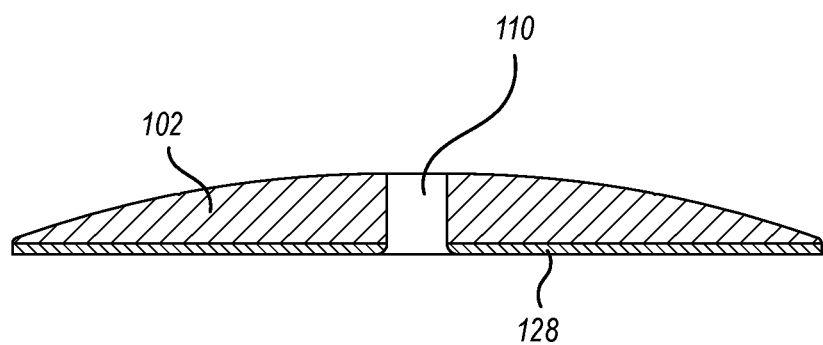
FIG. 3D illustrates a cross-sectional view of the cap of FIG. 3C.

In addition to, or instead of the interference fit between the cap 102 and the thick suture portion 112, the cap optionally include an adhesive applied to a side of the cap contacting the extravascular tissue, as illustrated in the embodiment of FIGS. 3C-3D. For instance, the cap 102 can include an adhesive layer 128 that bonds to the extravascular tissue when the cap 102 is advanced towards the anchor 108. The adhesive for the adhesive layer 128 can be a non-migrating adhesive in that it will not flow through the puncture as the extravascular tissue is sandwiched between the cap 102 and the anchor 108. Such adhesive can include a non-expanding glue, such as a non-expanding polyethylene glycol (PEG), a glue protein, such as a barnacle glue, cross-linked gelatins (non-biologic) cyanoacrylates, polyurethane adhesives, or glues or adhesives, combinations and modifications thereof. More generally, the adhesives can use cross-linking mechanisms that rely on chemical conjugation between reactive groups, free radical polymerization, oxidation reduction reaction, biological or biochemical coupling.

FIGS. 4-6B illustrate an example of a second extravascular component or fluid-blocking component 104, which can be a sealant. The fluid-blocking component 104 can be an active biologic material, such as polyethylene glycol (PEG), fibrin sealants, copolymer of glucosamine and N-acetyl glucosamine, dextran (complex branched glucan(a polysaccharide. polypeptide adhesive structures, adhesive protein containing L-3,4-dihydroxyphenylalanine (L-DOPA), adhesive protein containing DOPA and phosphoserine, collagen, polyacrylic acid, cross-linked with allyl sucrose or allyl pentaerythritol, polyacrylic acid, cross-linked with divinyl glycol, Acrylic resinous polymer composed of methyl-2-cynoacrylate units, or another fully bioabsorbable sealant-type material that could be optionally incorporated into a shaped, flexible substrate. The sealant material could be activated by fluids present in the patient's tissue tract, such as blood or other fluids, and can be protectively stored inside the sheath/actuators or a chamber of the delivery device until positioned directly on top of the cap 102.

Once advanced into the desired location, the sealant 104 can be exposed to the blood or fluid, such as through unsheathing the fluid-blocking component 104 and positioning the fluid-blocking component 104 into direct contact with the tissue where it can react by coming into contact with blood and other fluids. This reaction can cause the fluid-blocking component 104 to expand and absorb blood and other fluids and bond to surrounding tissue and the cap 102. The sealant can act as a glue and aid with "locking" the cap 102 in place on the blood vessel 10, and actively coagulates the entire access tract 22. The chemical formulation, quantity, carrier matrix, and dimensions of the fluid-blocking component 104 can be selected specifically to provide one or more of the functions of locking in place of the sealing component (e.g. cap 102), to provide a fast acting and leak-free dry close, and reduce tissue tract oozing.

For instance, the sealant can form a plug having a length of about 1 mm to about 10 mm and can optionally be trimmed to length in the patient along with the suture after deployment, or the adhesive component can extend the full length of the tissue tract and trimmed to fit the patient. When the fluid-blocking component 104 is formed of a matrix, the matrix can have an area of about 0.012 square inches to about 0.12 square inches, about 0.12 square inches to 0.6 square inches, about 0.6 to 1.0 square inches. The matrix material can be thin and flexible such that it can be wrapped around the suture in the delivery system to fit inside a tube for delivery to the implant location. This results in a volume of fluid-blocking component, optionally including a matrix containing a sealant such as PEG or other biocompatible material, of between about 0.004 to about 0.040 cubic inches in volume, about 0.0.040 to about 0.100 cubic inches, about 0.100 to about 0.400 cubic inches.

The fluid-blocking component 104 can be deployed so that is disposed on the suture 106. The fluid-blocking component 104, therefore, can be deployed in a flowable composition without a carrier matrix or can be formed as part or with a carrier matrix. For instance, the fluid-blocking component 104 can be disposed around the suture in a generally cylindrical component, can be bonded to the suture itself, can be bonded to the cap, and combinations or modifications thereof. Because the sealant 104 is positioned proximal relative to the cap 102, the sealant 104 can actively coagulate the access tract 22 and optionally actively coagulate all of access tract 22 to the surface of the skin 16.

Sealant 104, as shown in FIGS. 4-6B, can have a conical configuration when deployed, though in other embodiments the sealant 104 can have a continuous or uniform thickness along its length. The extravascular cap 102 can displace tissue at the access site 18 because the cap 102 can be larger than the arteriotomy. The sealant 104 can also fill the space created by the displaced tissue. The sealant 104 can be formed of material with properties which can cause it to swell from its original size when it comes into contact with bodily fluids, causing it to effectively cover and reinforce the seal formed by the cap 102. The sealant 104 can swell from its original size about 1 time to about 6 times, from about 2 times to about 4 times, or from about 2.5 times to about 3.5 times. It can be advantageous to optionally have the sealant expand up the access tract 22 as close as possible to the skin 16 to mitigate any bleeding.

When the sealant has a predetermined conical or tapered shape, the sealant 104 can be formed as a separate sealant component with a hole through the center, or other locations, to allow the sealant 104 to be threaded on to the suture 106. More generally, the suture may be threaded through one or more points through or around the sealant. The sealant component could be foam matrix or other formed substrate that a biocompatible material can be infused into and then formed into the desired shape, such as PEG. The sealant 104 can be a combination of two or more components which can be loaded into one of the actuators 50, 60, or 70, and then simultaneously activated by pressing down the handle or grip portions to expose the sealant 104 to bodily fluid. The two or more components can include one or more flowable component, with or without a matrix having a preformed shape or being biased to a particular shape.

In other embodiments, the sealant 104 and cap 102 can be deployed together as if they are one component. The cap 102 can cover the access site 18 and the sealant 104 can be activated on top of and above the cap 102 to seal the access tract 22.

Figure 1F:
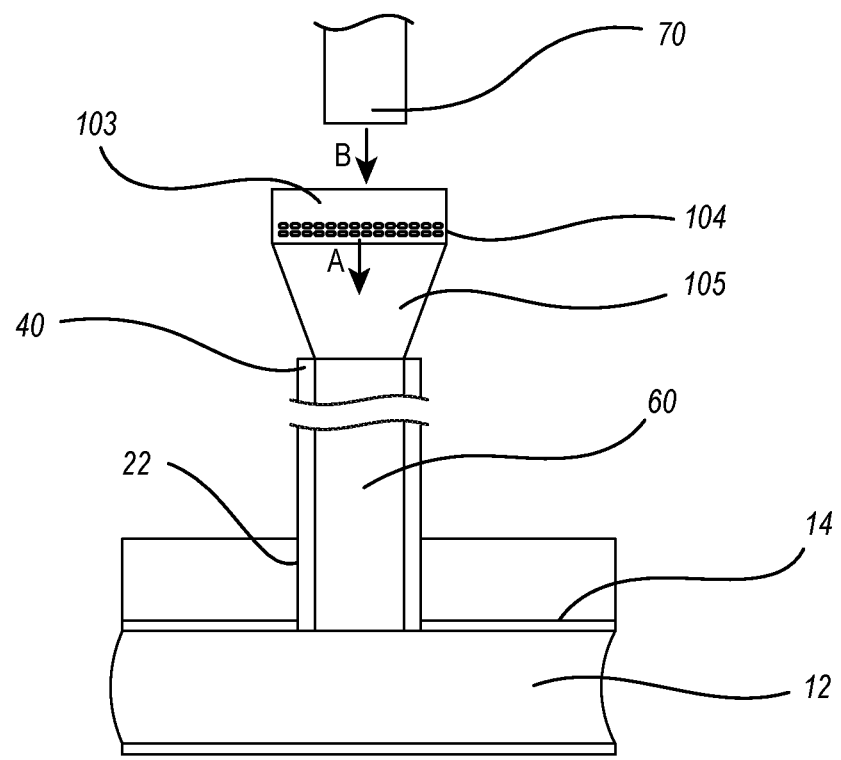
FIG. 1F illustrates a schematic representation of another alternate delivery system according to the present invention.

In other embodiments, as illustrated schematically in FIG. 1F (in which the actuator 50, the anchor 108, and the cap 102 are omitted for ease of explanation), the fluid-blocking component or sealant 104 can be stored in a chamber 103 at a proximal end of the delivery system. The fluid-blocking component or sealant 104 can be stored in a generally planar or flat-sheet form, optionally biased to that generally planar or flat-sheet form, and advanced to the cap 102 through a funnel 105 or other proximal deployment port that curls, folds, or otherwise changes the planar or flat-sheet form to a formed capable of being advanced toward the cap 102. In one configuration, the actuator 70 can be used to advance the fluid-blocking component or sealant 104 from the chamber (arrow A) along the actuator 60 to deploy the sealant 104 from within the actuator 60, such as when the actuator 70 is distally advanced (arrow B), when the actuator 60 is partially withdrawn proximally from engagement with the cap 102 following sandwiching the tissue between the cap 102 and the anchor, through movement of another actuator or structure, or combinations or modifications thereof. The movement exposes the fluid-blocking component or sealant 104 to the blood or other fluids causing the fluid-blocking component or sealant 104 to expand.

When introducing a coagulant or sealant, there is a risk of introducing embolizing material into the vessel 10 which can cause a clot and threaten a limb. Emergency surgery may be required to remove the foreign body. This risk can be mitigated by the configuration of closure device 100 due to the use of the cap 102 to first cover the access site 18 so that the extravascular fluid-blocking component or sealant 104 104 cannot pass into the vessel 10.

The combination of a low profile cap component, including degradable, absorbable, or resorbable material that is stable (material does not expand or aggressively bond to tissue), plus the active sealant material on top, combined as an extravascular implant is unique and distinguishes this design from other closure devices.

Turning now to FIGS. 7A-7H, the closure device 100 can include an intravascular anchor 108, for example, a graft-type anchor. The intravascular anchor 108 can include one or more of the following elements: 1) a large surface area in an elongate shape otherwise referred to as elongate member 117, 2) a central keel 120 which can provide suture attachment and overall rigidity, 3) a flexible portion or membrane 122 which can conform to a vessel wall, 5) holes, eyelets, or other structure 118 which can provide for suture attachment to an extravascular component (e.g., cap 102) of a closure device 100, and 6) flexible edges 126 of the flexible portion or membrane which can allow for storage in a cylindrical state to permit delivery of the closure device 100 to the vessel 10. The anchor 108 can be formed of multiple sub-components that are joined together or be formed as a monolithic component where the identified one or more elements are formed as a single component, such as through casting or through machining of a starting workpiece.

The intravascular anchor 108 (also referred to as "anchor") can be formed of a bioabsorbable material, while having flexibility properties that allow the anchor 108 to be curled up into a smaller profile inside of a delivery sheath, such as the delivery sheath 40. This allows a larger sealing surface that can unfurl once free of the delivery tube. The intravascular anchor 108 is attached to the suture 106 using a pattern that can distribute the tensile load more widely across the breadth of the anchor 108 to prevent fracture from a high concentration of force during device deployment.

The intravascular anchor 108 can have a curved profile in order to better conform to the curvature of the vessel wall. The anchor 108 can also have an enlarged central portion or a keel 120. The keel 120 can help to reinforce the seal formed over the access site 18 by the closure device 100 and provide a suture attachment point. The rigidity of the keel 120 can provide mechanical leverage and a robust location to advance and eject the anchor 108 out from the delivery sheath 40. The keel 120 can have a thickness of about 0.5 mm to about 0.8 mm, of about 0.6 mm to about 0.9 mm, of about 0.7 mm to about 1.0 mm, or other thickness to provide the desired suture attachment location.

Surrounding the keel 120 is the elongate member 117. The materials forming the elongate member 117 can be the same as the keel 120, such a bioabsorbable material, with the material a have a durometer ranging from about 50 Shore A to about 100 Shore A, from about 80 Shore A to about 90 Shore A, or durometers as chosen based upon the closure location. The elongate member 117 can have thinner, flexible sections relative to the keel 120, which can conform to the curved vessel wall 14. The flexibility can also allow the anchor 108 to conform to the unique calcification buildup in the vessel 10. The elongate member 117 can have an ellipse or oval shape having a minor axis dimension from about 2.0 mm to about 10.0 mm, from about 3.0 mm to about 5.0 mm, or about 4 mm, while a major axis can range from about 4.0 mm to about 12.0 mm, from about 6.0 mm to about 8.0 mm, or about 6.0 mm. It is understood that the configuration of the anchor, and more generally, the closure device or implant can be varied based upon the particular opening to close so that the dimensions can be adjusted to accommodate, generally, 5-8 F openings or openings larger than 8 F and smaller than 5 F.

The ridge or keel 120 can run the length of the central axis of the elongate member 117 and can impart rigidity where suture 106 can be attached. The suture 106 can be attached through suture attachment points or holes 118 in the keel 120. One or more holes 118 can provide points through which the suture 106 can be threaded to attach the anchor 108 to the cap 102 and sealant 104. The holes 118 can be evenly or non-evenly spaced along the length of the keel 120. The spacing of the holes 118 can help to spread the tensile load across a desired length of the anchor 108, such as all or some portion of the length of the anchor 108, and can prevent fracture of the anchor 108 under load. In the embodiment shown in FIGS. 7A-7H, free distal ends of the suture 106 can each be threaded through each of the outermost holes 118a and then both can be threaded through the middle holes 118b and up through the access site 18 and braided back onto the suture 106 to form the thick suture portion 112.

The anchor 108 can be injection molded, cast, stamped, machined, combinations or modifications thereof, and include one or more bioabsorbable materials, bioabsorbable polymers, or bioabsorbable elastomers depending on the degree of strength, stiffness and absorption rate desired. The anchor 108 structure can be formed of a homogenous material mixture where flexibility is adjusted through a combination of geometry and material formulation. A secondary adhesive material may be attached or bonded to the bottom surface of anchor 108 to increase attachment strength and improve sealing performance against the blood vessel. The anchor provides a safe manner for the sealant to interact directly with the blood vessel tissue without risk of embolizing into the blood vessel lumen because it is attached to anchor 108. The bioabsorbable materials can include, for example, and not by way of limitation, Polyglycolic acid (PGA), Polylactide (PLA), Poly-L-Latic acid (PLLA), Polycaprolactone (PCL), Poly-DL-lactic acid (PDLLA), Poly trimethylene carbonate (PTMC), Poly paradioxanone (PPDO), combinations and/or modifications thereof. More generally, the materials forming the anchor 108 can have a durometer ranging from about 80 Shore A to about 90 Shore A. Alternatively, when the anchor 108 is temporarily deployed, the anchor can be formed of a non-bioabsorbable material, such as polyvinyl chloride (PVC), Polyether ether ketone (PEEK), Polytetrafluorethylene (PTFE), nylon, silicone, urethane, thermoplastic elastomers like Polyether block amide (PEBAX), polyethylene terephthalate (PET), Fluoropolymers, or biocompatible materials, combinations and/or modifications thereof.

The anchor 108 can have a mass ranging from about 4 mg to 8 mg (for 4 mm×6 mm ellipse), from about 8 mg to about 16 mg (for 5 mm×7 mm ellipse), or from about 15 mg to 30 mg (for 8×10 mm ellipse). With a lower overall mass, less force is used to hold the anchor 108 in place between the frictional engagement between the cap 102 and the suture 106. This results in smaller overall system, thereby making positioning within the patient simpler with reduced overall impact on the patient's recovery.

Figure 8A:
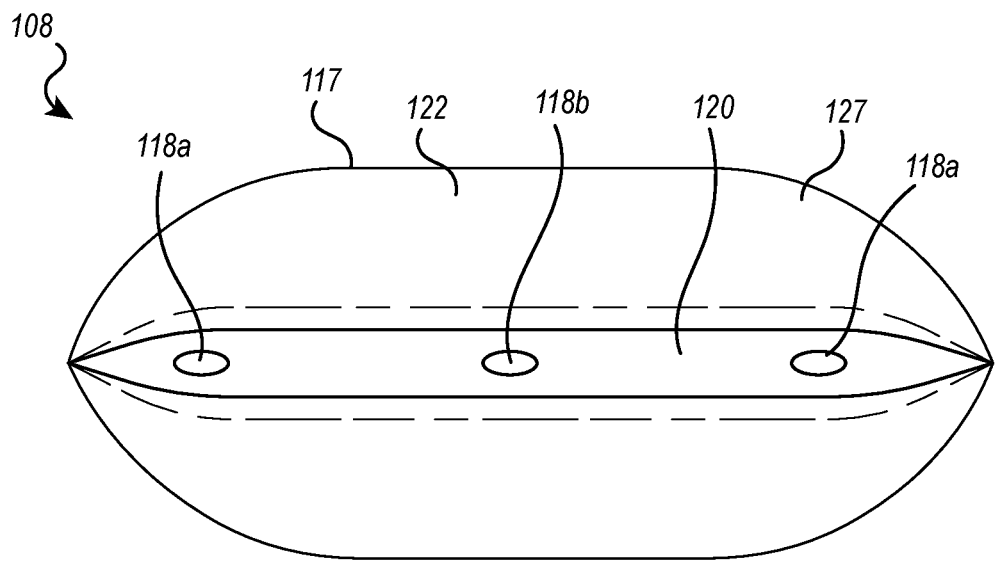
FIG. 8A illustrates a lumen facing side of an alternate embodiment of an intravascular anchor.
Figure 8B:
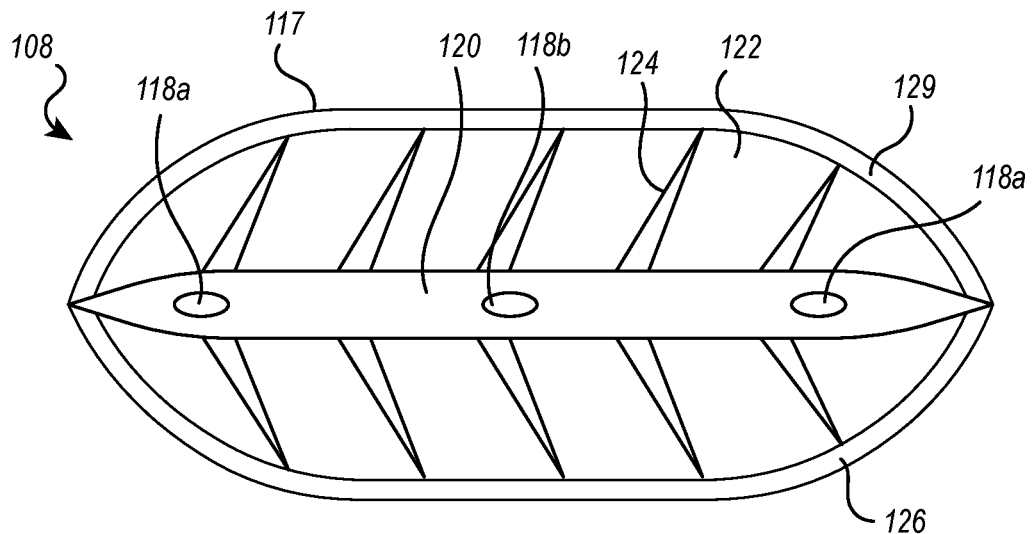
FIG. 8B illustrates an intima facing side of the embodiment of the intravascular anchor of FIG. 8A.

FIGS. 8A and 8B illustrate another example embodiment of the intravascular anchor 108. In FIGS. 8A-8B, the anchor 108 includes a lumen facing side 127 (FIG. 8A) and an intima facing side 129 (FIG. 8B). The anchor 108 can include an elongate body 117 having a flexible member or membrane 122, a keel 120 positioned at the central axis of the elongate body 117 and spanning the length of the elongate body 117 which can provide adequate stiffness for attachment of the intravascular anchor 108 to the extravascular element of the closure device 100 by suture 106 (e.g., cap 102).

The keel 120 can be raised relative to the lumen facing side surface of the anchor 108, which can help to maintain the position of the anchor 108 on the vessel wall 114. The intima side of the anchor 108 can include a plurality of ribs 124 radiating outward from the keel 120 to the raised edge 126 forming the perimeter of the elongate body 117. The raised elements of the ribs 124 and raised edge 126 provide for encapsulation of localized plaque on the vessel wall 114. The stiffness of the raised edge 126 of the anchor 108 may be correlated to the stiffness and/or pattern, number, and/or thickness of the ribs 124 ribs radiating from the keel 120. The width and taper of the ribs 124 may be varied to influence the compliance or the stiffness of the edge 126 of the anchor 108.

Figure 9A:
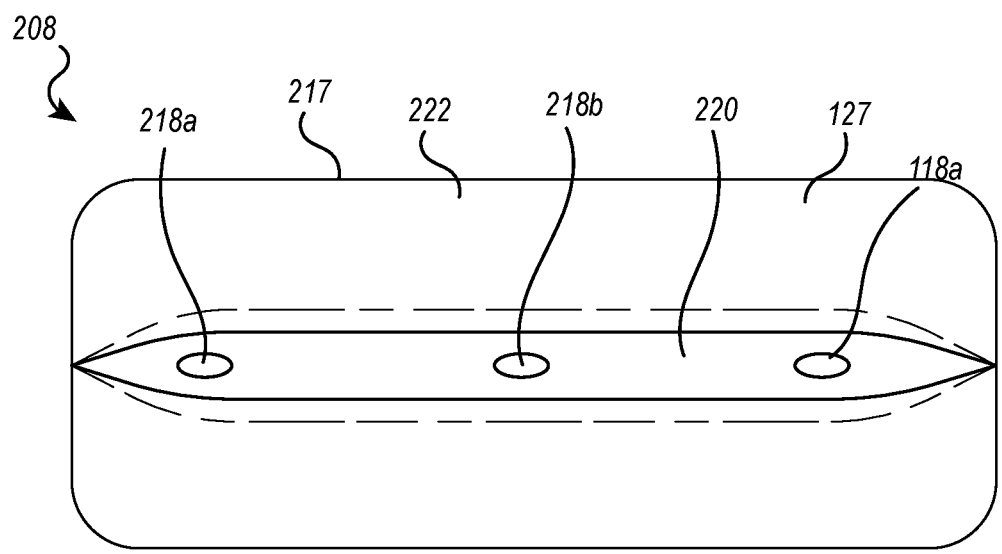
FIG. 9A illustrates a lumen facing side of another embodiment of an intravascular anchor.
Figure 9B:
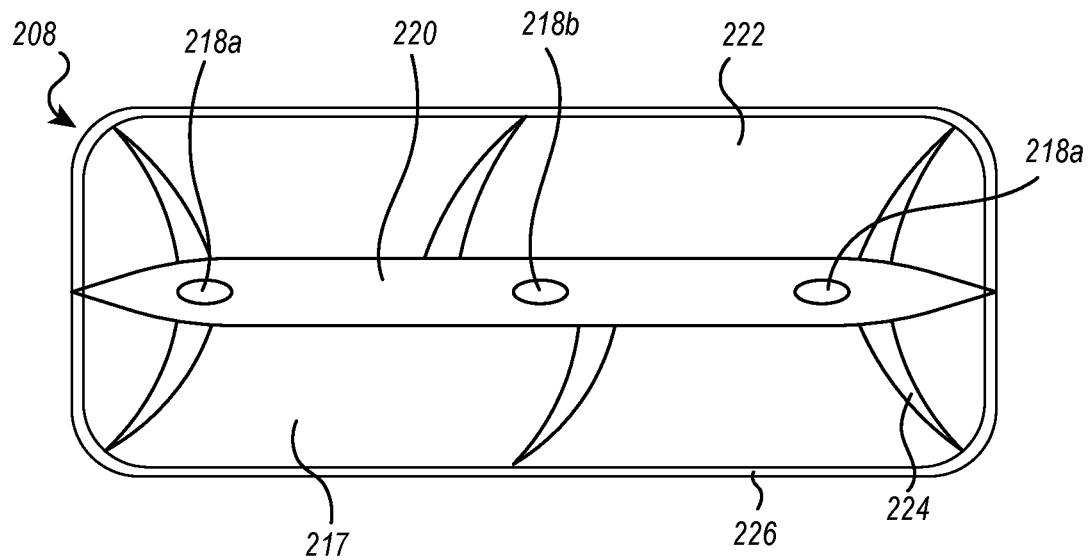
FIG. 9B illustrates an intima facing side of the embodiment of the intravascular anchor of FIG. 9A.

FIGS. 9A-9B illustrate another embodiment of an anchor 208. The anchor 208 can include an elongate body 217 having a flexible member or membrane 222 and a centrally-located raised keel 220 spanning the length of the elongate body 217. The elongate shape of the anchor 208 is modified to maximize the surface area of the anchor 208. In this depiction the number of ribs 224 is reduced which may increase compliance to the vessel lumen wall 14. The anchor 208 can also have a raised edge 226 running the perimeter of the elongate body 117. One or more holes 218 in the keel 220 provide points through which a suture 106 can be threaded to attach the anchor 208 to extravascular components of the closure device 100.

Figure 10A:
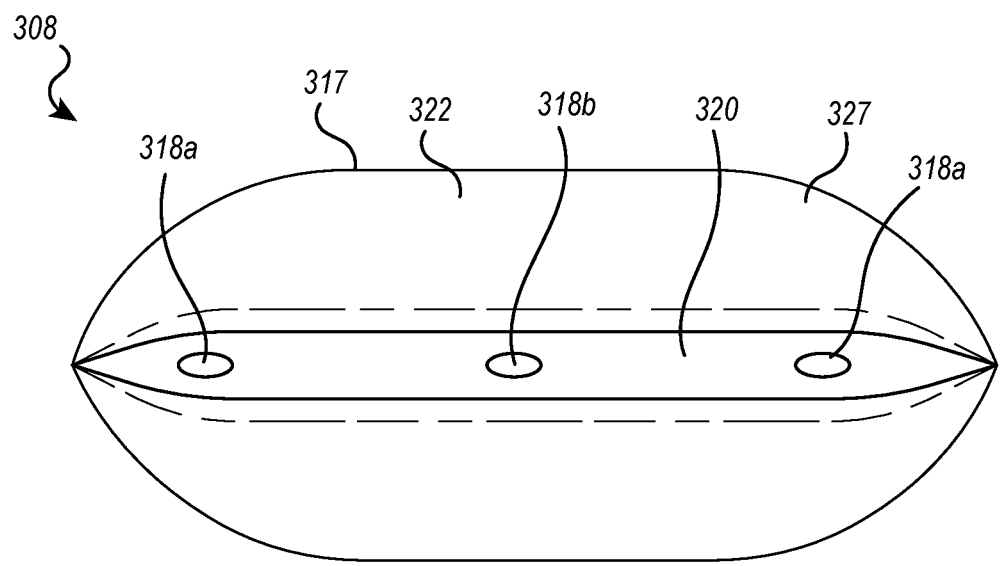
FIG. 10A illustrates a lumen facing side of another embodiment of an intravascular anchor.
Figure 10B:
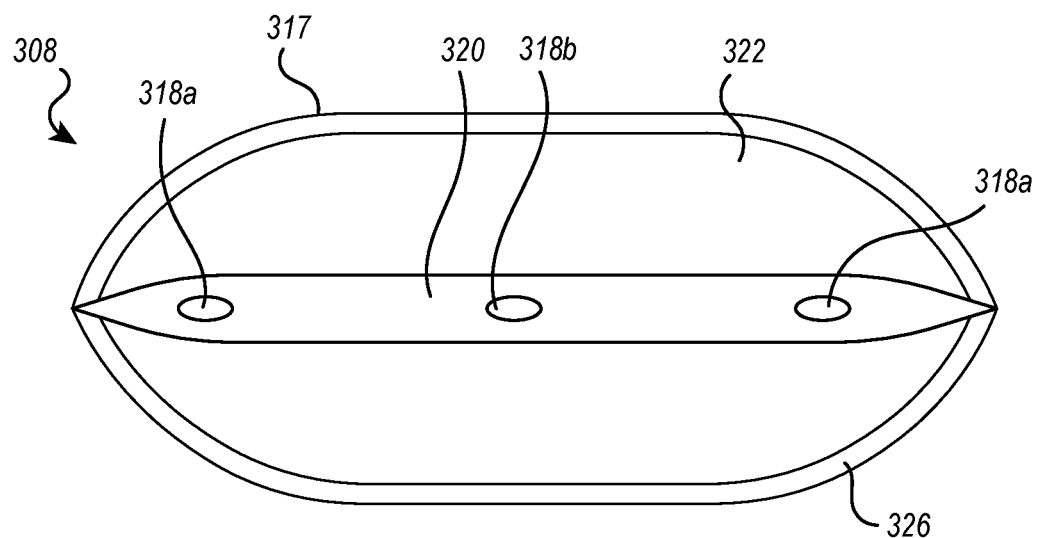
FIG. 10B illustrates an intima facing side of the embodiment of the intravascular anchor of FIG. 10A.

FIGS. 10A-10B, illustrate another embodiment of an anchor 308. The anchor 308 can include an elongate body 317 having a flexible membrane and a raised keel 320 located on and spanning the length of the central axis of the elongate body 317. The keel 320 can include one or more holes 318 through which suture 106 can be threaded. In this embodiment the ribs (124, 224) are omitted to permit maximum flexibility of the anchor 308. The raised edge 326 running the perimeter of the intima side of the anchor 308 can impart the anchor 308 with requisite structural integrity to maintain the shape of the anchor 308 when positioned on the lumen wall 14.

Method of Closure Device Insertion

Figure 11A:
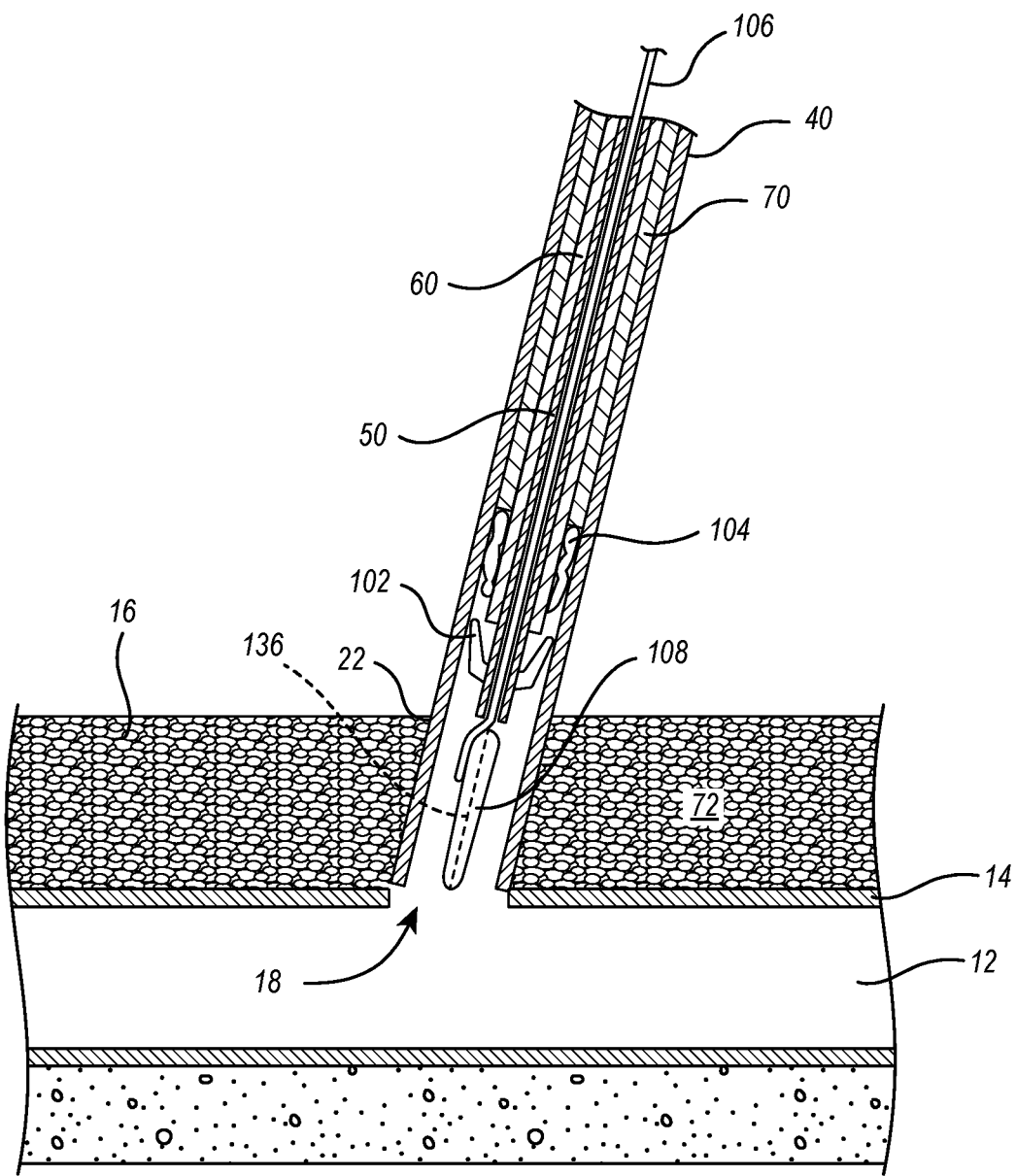
FIGS. 11A-11D illustrate a method of delivering a closure device to an access site on a vessel.

Reference is now made to FIG. 11A, which illustrates a step in the process of deploying the anchor 108. As shown in FIG. 11A, the delivery sheath 40 can be positioned to move the distal end of the outer housing 42 through an access tract 22 defined in tissue 72 and into proximity with a lumen 12 and a puncture or access site 18 defined in a lumen wall 14 in particular. The distal end of the delivery sheath 40 is advanced into the lumen 12 until pulsating blood is visually observed from a proximally positioned blood outlet port 49 (FIG. 1A) of a bleed back or blood marker lumen formed in a wall of the delivery sheath 40 or formed by a separated bleed back tube formed either interior or externally of the delivery sheath 40. The blood inlet port 47 (FIG. 1A) in fluid communication with the blood outlet port 49 is disposed toward the distal end of the delivery sheath.

Once blood flow is observed, the actuator 50 can be manipulated as described above (and as shown in FIG. 11B) to cause the anchor 108 to be pushed out of the distal end 42A of the outer housing 42. Alternatively, the actuator 60 may push the closure element or cap 102 which may, in turn, push the anchor 108 distally relative to the outer housing 42, thereby deploying the anchor 108 from the distal end 42A of the outer housing 42. In such a case the actuator 50 can optionally be omitted.

Figure 11B:
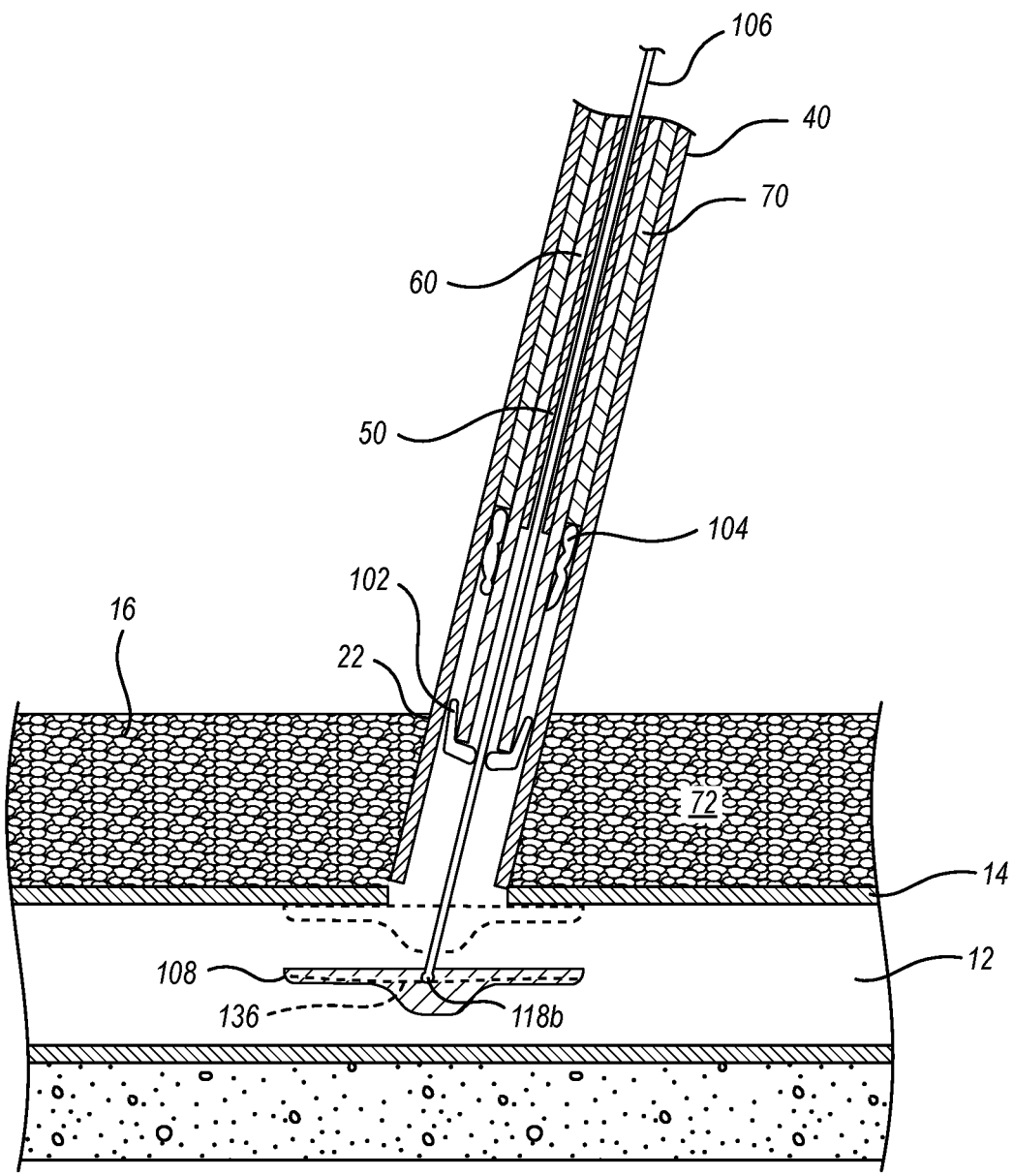

In one embodiment, once deployed, the anchor 108 may rotate or be rotated from a first orientation, in which the major axis 136 of the anchor 108 is at a small angle or generally parallel with the outer housing 42 and generally perpendicular to the lumen wall 14 as shown in FIG. 11A, to a second orientation in which the major axis 136 of the anchor 108 is generally parallel with the lumen 12 and at a greater angle or generally perpendicular to the delivery sheath 40 as shown in FIG. 11B.

Figure 15:
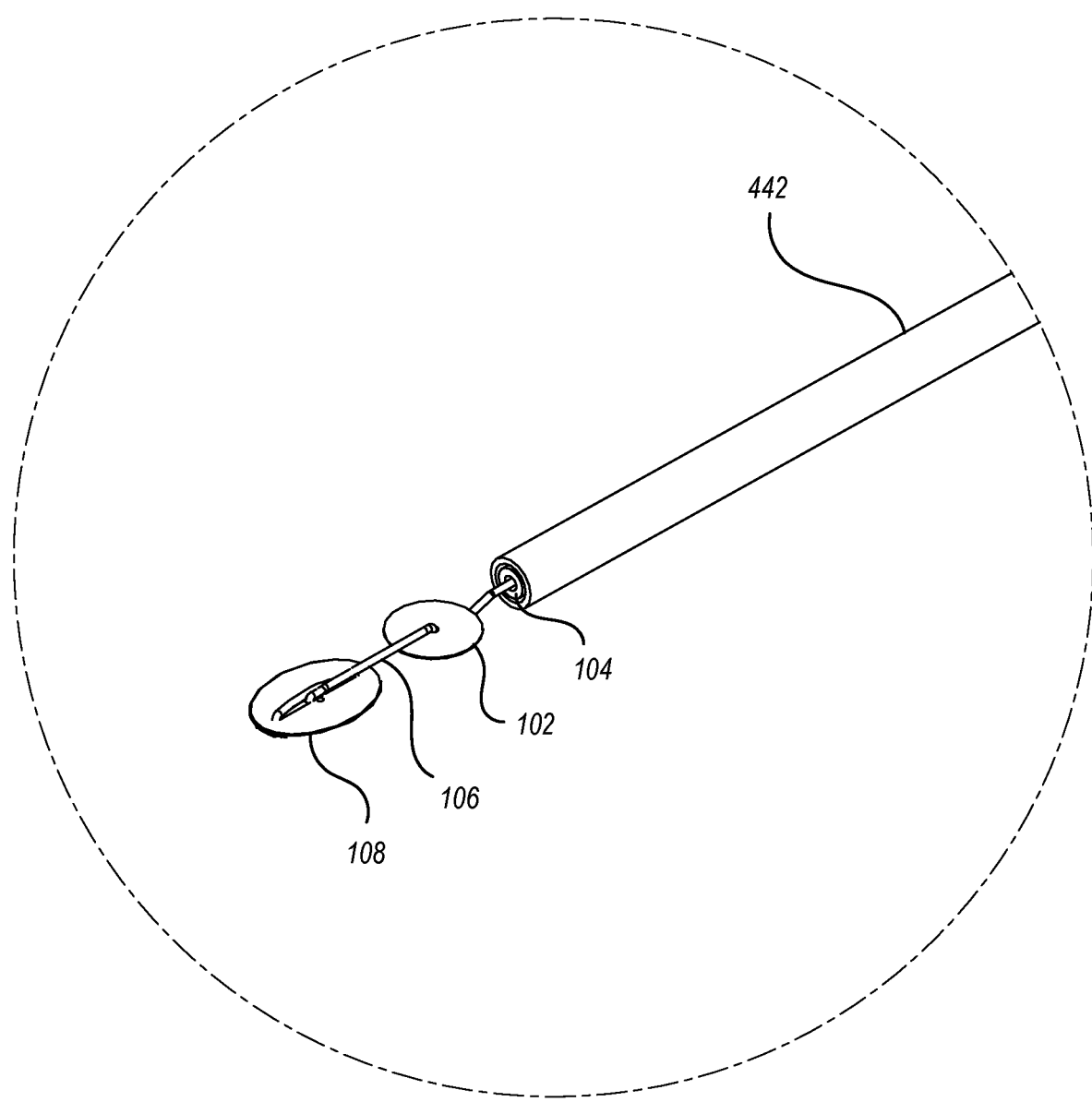
FIG. 15 illustrates the implant assembly of FIGS. 14A and 14C.
Figure 16:
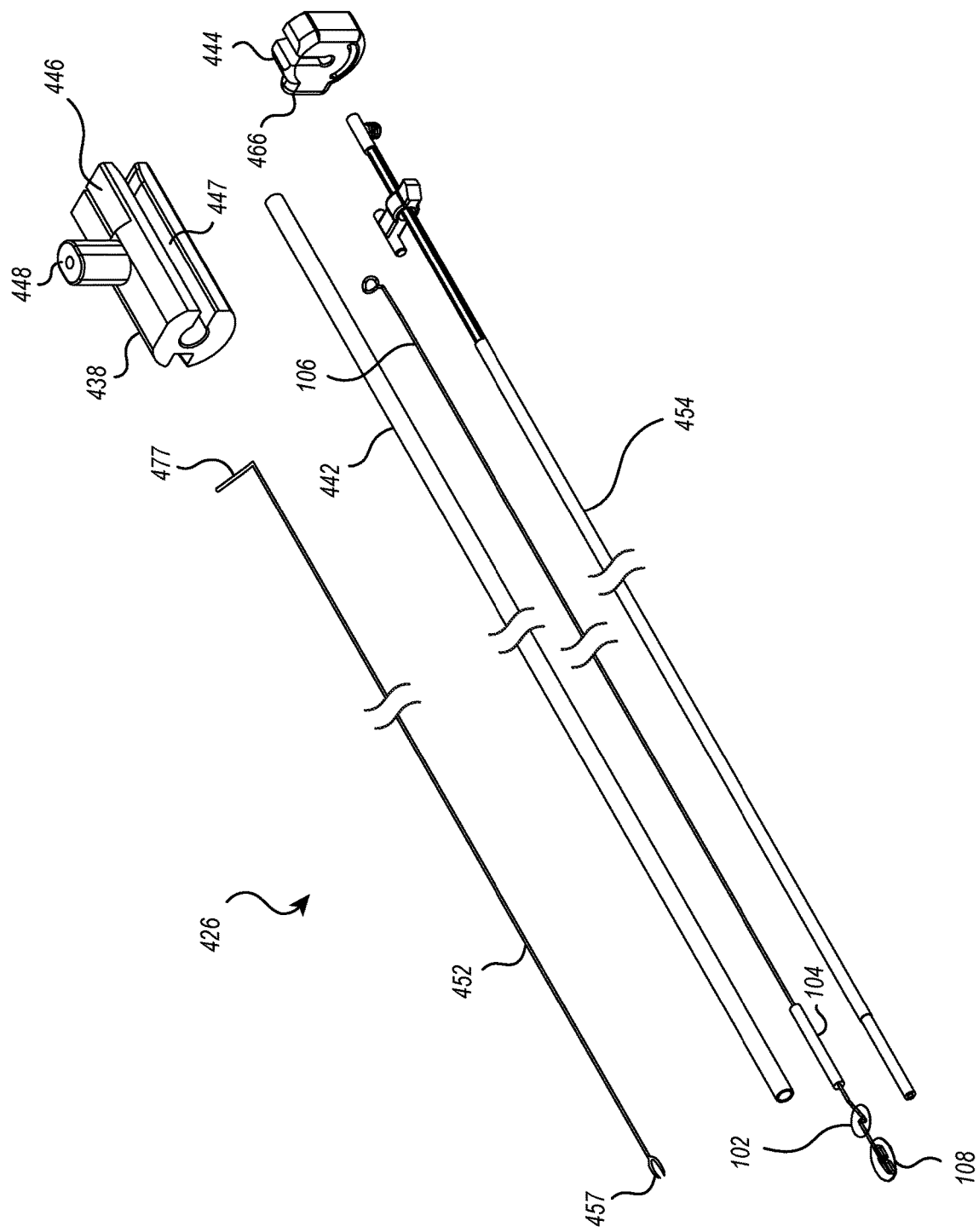
FIG. 16 illustrates an exploded view of the implant assembly of FIG. 15.

In particular, as shown in FIG. 11B, once the anchor 108 is pushed from the distal end 42A of the outer housing 42, the anchor 108 may rotate or be rotated to the second orientation, such as by tension applied to by the suture element 106 to the anchor 108 by way of the central or middle hole 118b. The anchor 108 can then be drawn in the proximal direction to secure the anchor 108 against a distal surface 14A of the lumen wall 14, as illustrated in phantom in FIG. 11B. While the suture 106 is illustrated extending proximally within the lumen of the actuator 50 in FIG. 11A and FIG. 11B, when the actuators are non-coaxial, such as illustrated in FIGS. 15 and 16, the suture 106 need not extend within a lumen of the actuator 50 and actuator 50 need not include a lumen. The suture 106 can extend within any lumen of the delivery system 30, such as illustrated in solid and dashed schematic representations of the suture 106 in FIG. 16

Figure 11C:
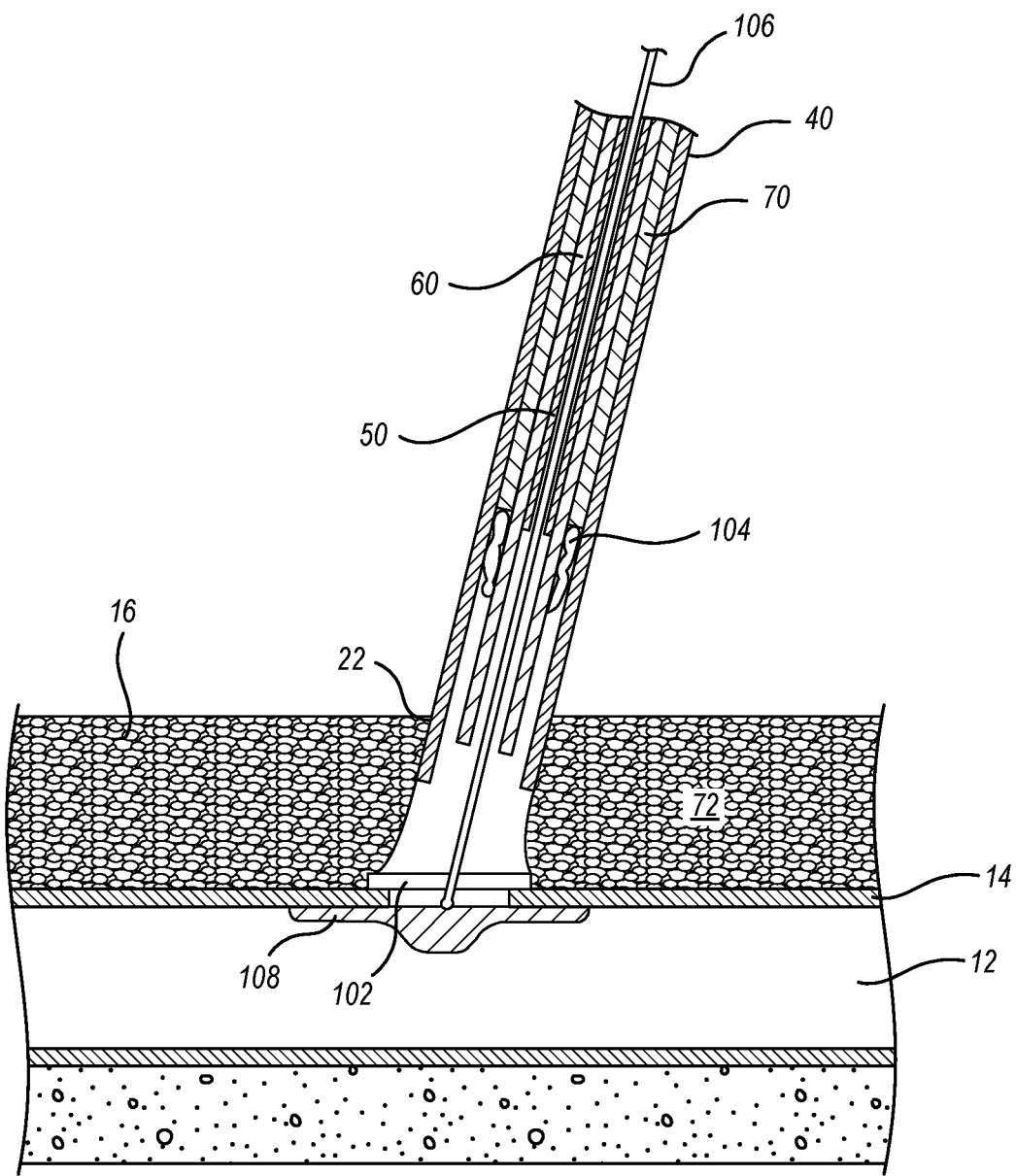

With the anchor 108 deployed and positioned against the lumen wall 14 and the delivery sheath 40 partially retracted into the access tract 22 so that the distal, the actuator 60 may then deploy the cap 102 proximal the puncture 18 between the lumen wall 14 and the tissue 72 through which the tract 22 is formed. In particular, as shown in FIG. 11C the actuator 60 can be advanced distally, the delivery sheath 40 can be drawn proximally, and/or some combination of such movements can be used to move the cap 102 distally out of the outer housing 42 and into contact with the proximal side or extravascular side 14B of the lumen wall 14 adjacent the puncture 18. The lumen wall 14 is positioned between the anchor 108 and the cap 102 with the cap 102 positioned on the extravascular side of the access site 18 and "locked" in place as a result of an interference fit created by the thick suture portion 112. Thus, the cap 102 can be positioned to reduce or stop the flow of fluid out of the tract 22 by covering the puncture 18 and/or obstructing the tract 22.

To verify that flow is reduced or stopped, the practitioner can view blood flow from the blood outlet port 49 (FIG. 1A) and determine a degree of hemostasis. A continued degree of blood flow from the blood outlet port 49 (FIG. 1A) may indicate that hemostasis has not been adequately achieved and indicate to the practitioner to continue positioning the cap 102 against the tissue to provide improved hemostasis. Alternatively, blood flow can be observed by maintaining one or more of the valves or seals 58, 68, 78 of the actuators 50, 60, or 70 or the one or more valves or seals 45 of the delivery sheath 40 open to allow blood to flow from an end of one or more of the actuators 50, 60, or 70 or the delivery sheath 40. For instance, by way of example of one particular configuration, the actuator 60 can include an enlarged portion that maintains the valve or seal 45 of the delivery sheath 40 open so that blood exits from the end of the lumen when hemostasis has not been achieved. As with the blood flow from the blood outlet port 49 (FIG. 1A), a continued degree of blood flow from the end of one or more of the actuators 50, 60, or 70 or delivery sheath 40 may indicate that hemostasis has not been adequately achieved and indicate to the practitioner to continue positioning the cap 102 against the tissue to provide improved hemostasis. Retracting the enlarged portion away from or advancing the enlarged portion through the one or more valves or seals allows the valves or seals to close following advancing the cap 102 towards the anchor 108 to improve hemostasis and reduce blood flow.

Returning to FIG. 11C, advancing the cap 102 towards the anchor 108 aids with stabilizing the tissue around the puncture 18 in order to facilitate closure of the puncture 18. In particular, once the anchor 108 and the cap 102 are deployed, tension can be applied to the suture 106 to secure the anchor 108 against a distal side 14A of the lumen wall 14 while the actuator 60 advances the cap 102 distally. In one example, a suture lock (not shown) can be utilized to help maintain the tension in the suture element 106. The combination of the forces exerted by the anchor 108 and the cap 102 on the lumen wall 14 provides a compressive force on the tissue near the puncture 18, i.e., sandwiching the tissue between the anchor 108 and the cap 102. The tension applied to the suture can range 1 lbf. to about 16 lbf., from about 1 lbf. to about 8 lbf., from about 2 lbf. to about 6 lbf., or about 2.5 lbf. Because the anchor 108 is formed of a resilient compliably material and the cap 102 can be formed of elastomeric materials (such as bioabsorbable polymers, bioabsorbable elastomers, etc.), the properties allow the anchor 108 and the cap 102 to accommodate the applied forces without fracturing. The suture 106 can also include a visual indicator to show the user when the cap 102 has reached the proper depth, i.e. the cap 102 has reached the artery. If too much force is applied, this may cause the suture to break, however, due to the lack of a knot or other static element maintaining the cap 102 in a fixed position, the cap 102 and the anchor 108 will not over-tension. Because of this feature, the user does not have to worry about the degree of force applied.

Placement of the cap 102 also pushes the tissue 72 in a transverse direction in relation to an axis of the tract 22. This increases a space for subsequent delivery of the sealant 104 and so increases a surface area of the lumen wall 14 and the cap 102 that can receive the sealant 104. By so doing, the efficacy of access site closure is enhanced.

Optionally, in a configuration when the actuator 60 can deploy both the anchor 108 and the cap 102, the actuator 60 can remain in continuous contact with the cap 102 throughout the deployment process. Such a configuration can allow the anchor 108 and/or cap 102 to be deployed by advancing the actuator 60 in a single direction. By facilitating deployment of the anchor 108 and cap 102 using one-way movement of the actuator 60, and by utilizing a single actuator, the delivery system can be used quickly and easily deploy the anchor 108 and/or cap 102 and sealant 104.

Optionally, in one configuration when the actuator 60 can both deploy the cap 102 and advance the sealant 104 towards the cap 102, the distal movement of the actuator 60 advances the sealant 104 towards the cap 102, with subsequent proximal movement releasing the sealant 104 from within the actuator 60. In this configuration, the actuator 70 is optionally omitted.

Figure 11D:
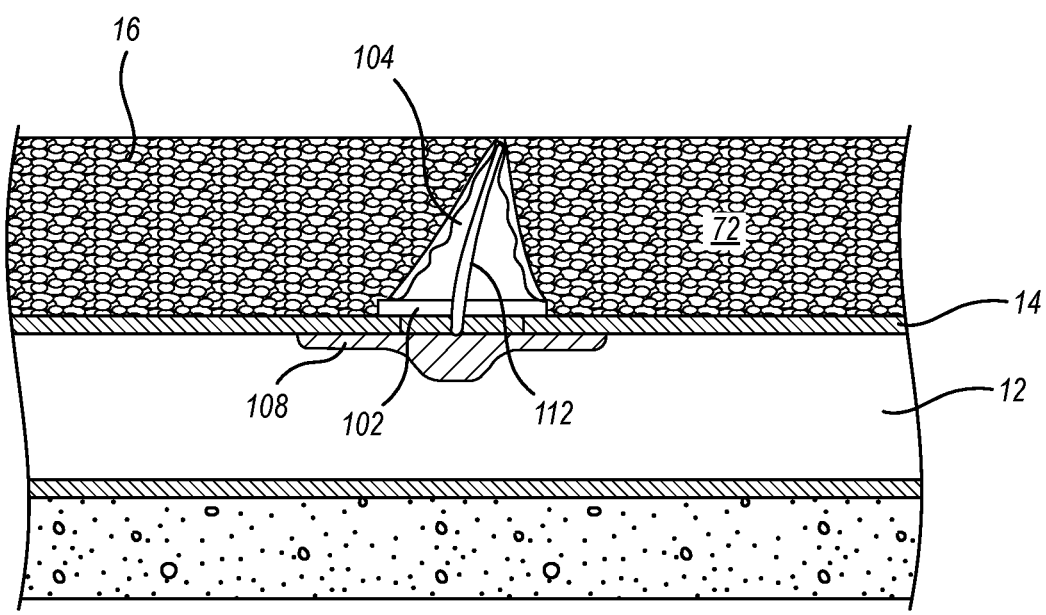

Returning to the illustrated configuration, once the cap 102 is placed, the sealant 104 can be deployed from the delivery sheath 40 by proximally withdrawing the delivery sheath 40, and optionally the actuator 60, and distally advancing the actuator 70, or some combination of one or more of such movements, to advance or release the sealant 104 from the outer housing 42 and into contact with the proximal side 14B of the lumen wall 14 and the cap 102. As the delivery sheath 40 is proximally moved or removed, and/or the actuator 60 is proximally moved or withdrawn, the sealant 104 is exposed to bodily fluids to activate the sealant 104, as illustrated in FIG. 11D. The activated sealant 104 can act as an adhesive to secure the cap 102 in place as well as reinforce the hemostatic effect of the cap 102 by preventing leakage and coagulating the access tract 22. It can be advantageous to have the sealant as close to the surface of the skin as possible to mitigate any potential bleeding.

While the sealant is activated, such as can occur in from about 0.25 minutes to about 5 minutes, from about 0.5 minutes to about 4 minutes, from about 1 minute to about 3 minutes, from about 0.25 minutes to about 1 minute, from about 0.25 minutes to about 0.75 minutes, the practitioner can view blood flow, if any, from the blood outlet port 49 (FIG. 1A) and determine a degree of hemo stasis. Based upon the force applied to the cap 102 to seal the access site 18, the cap 102 can seal or substantially seal the access site 18 resulting in the sealant 104 being used to limit tissue oozing around the cap 102 and from the tissue tract 22 and provide secondary securing of the cap 102 in relation to the suture 106 and the access site 18. Stated another way, primary closure of the access site 18 can be achieved through the sealing provided by the anchor and cap, while the sealant 104 provides secondary sealing and/or stopping of tract ooze. If there is, however, a continued degree of blood flow from the blood outlet port 49 (FIG. 1A), the physician can manipulate the actuators and anchor to tighten the cap 102 on the suture 106 or optionally wait for the sealant 104 to sufficiently activate to reduce or eliminate blood flow to the physician's preferences. More generally, with the cap 102 and sealant 108 combination, dry close may be achieved within seconds of activating the sealant. Users can also compress the area with a gauze to express out any blood and then check for hemostasis. While illustrative times to hemostasis are provided, time to hemostasis can be impacted by anticoagulant medications given to patient. With the combination of cap and proximal sealant, hemostasis may be achieved faster than sealant alone.

Whether complete or substantial complete hemostasis occurs from the cap 102, or a combination of the cap 102 and the sealant 104, after hemostasis is achieved, the suture 106 can be trimmed by pushing down on the skin 16 while tensioning the suture 106 and using a suture trimming device (not shown), such as scalpel or other suture trimming device, to trim the suture as close to the skin as possible. Once the skin is released, the suture will sit well below the surface of the skin as shown in FIG. 11D.

While reference has been made to the anchor 108 (208, 308) remaining in the blood vessel and degraded, absorbed, or resorbed by the patient's body, it will be understood that in other configurations, the anchor 108 may be deployed and subsequently removed once sufficient closure of the puncture has occurred. In such a case, the anchor 108 is "temporarily" deployed and the other portions of the closure element, such as the cap 102 with the adhesive layer 128 (see FIGS. 3C and 3D) and the fluid-blocking component 104 described herein can be used to close the access site following removal of the anchor 108. The cap 102 with the adhesive layer 128 may or may not cooperate with a suture 106 and lock onto a suture 106 that is optionally attached to the anchor 108. The cap 102 is maintained in place against the vessel wall 14 by the adhesive layer 128 and optionally the fluid-blocking component 104, with the fluid-blocking component 104 reducing or eliminating any tissue tract oozing. Delivery of the temporary anchor, the cap, and the sealant in this alternate configuration can be performed using the delivery systems and devices described herein, while accommodating removal of the anchor 108 by proximally drawing on the suture 106, or another anchor actuator, to remove the anchor 108. The anchor 108 may optionally pass through the lumen 110 of the cap 102, with the body of the cap being sufficiently resilient to return to a closed state to close the access site. Alternatively, the anchor 108 can be withdrawn past a side of the cap 102, with the cap 102 having sufficient resiliency to temporary deformation to return to a state to seal against the extravascular side of the vessel wall.

Handle Assembly Vessel Closure Delivery System

FIGS. 12-23B illustrate a delivery system and method of inserting a closure device of the type disclosed above. Delivery system 430 can comprise a handle assembly 400 and a delivery sheath 440. The handle assembly 400 can be configured to be selectively attached to a delivery sheath 440 (similar to delivery sheath 40). Once attached to the delivery sheath 440, the handle assembly 400 can be used to insert a closure device, such as, for example, closure device 100.

Figure 12:
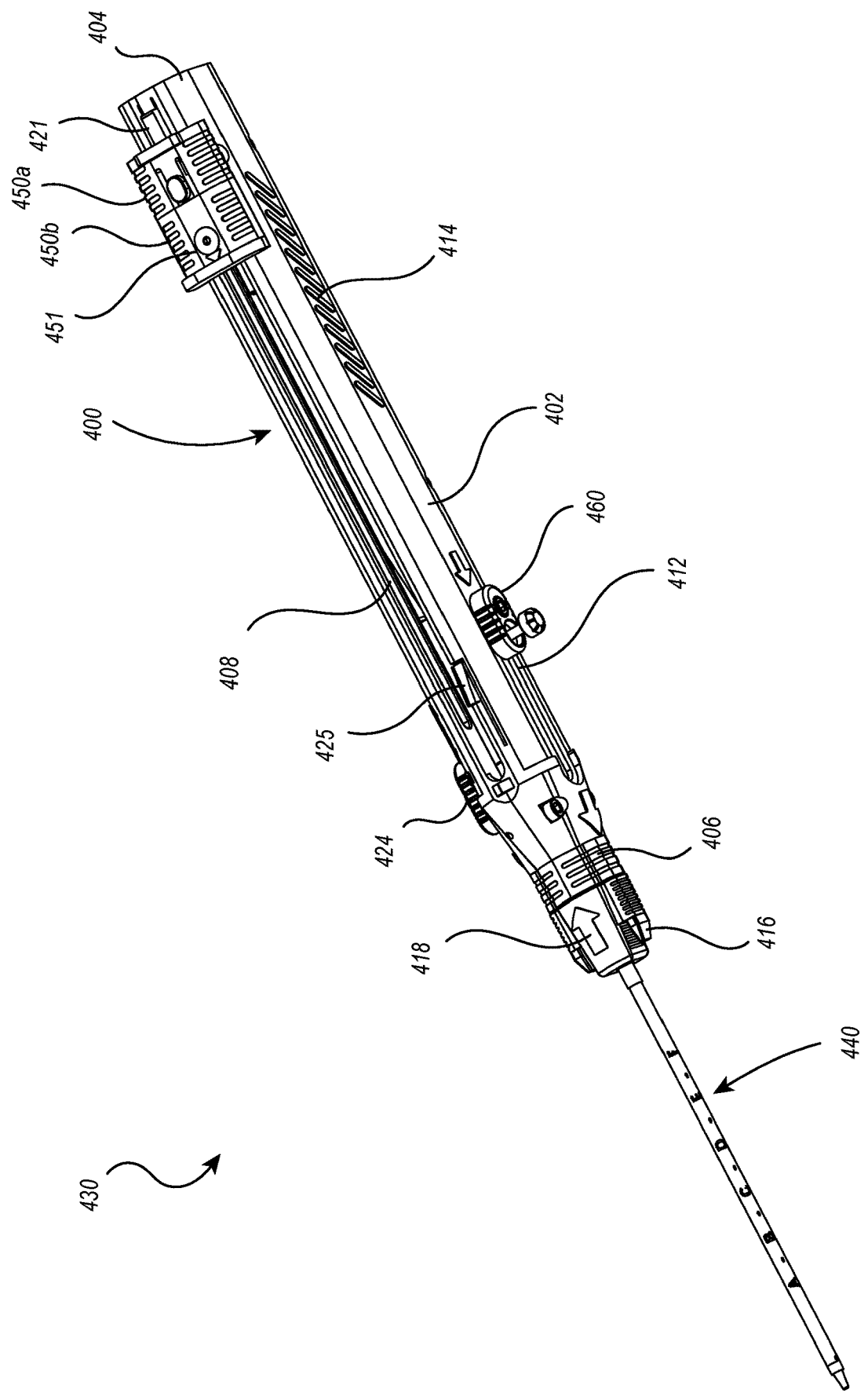
FIG. 12 illustrates an alternate embodiment of a delivery system in which a closure device can be implemented.
Figure 13A:
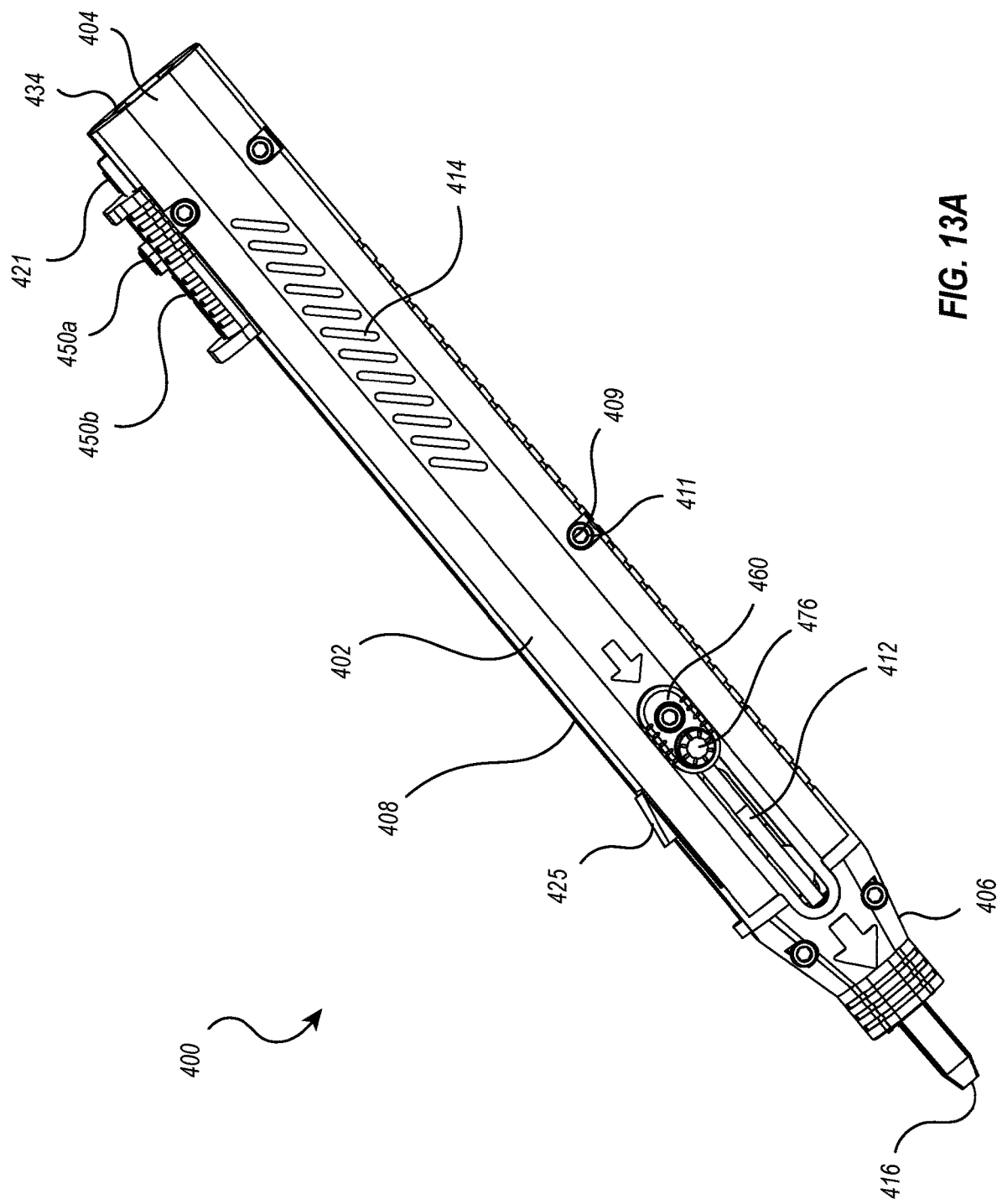
FIGS. 13A and 13B illustrate side views of a handle assembly of the delivery system of FIG. 12.
Figure 13B:
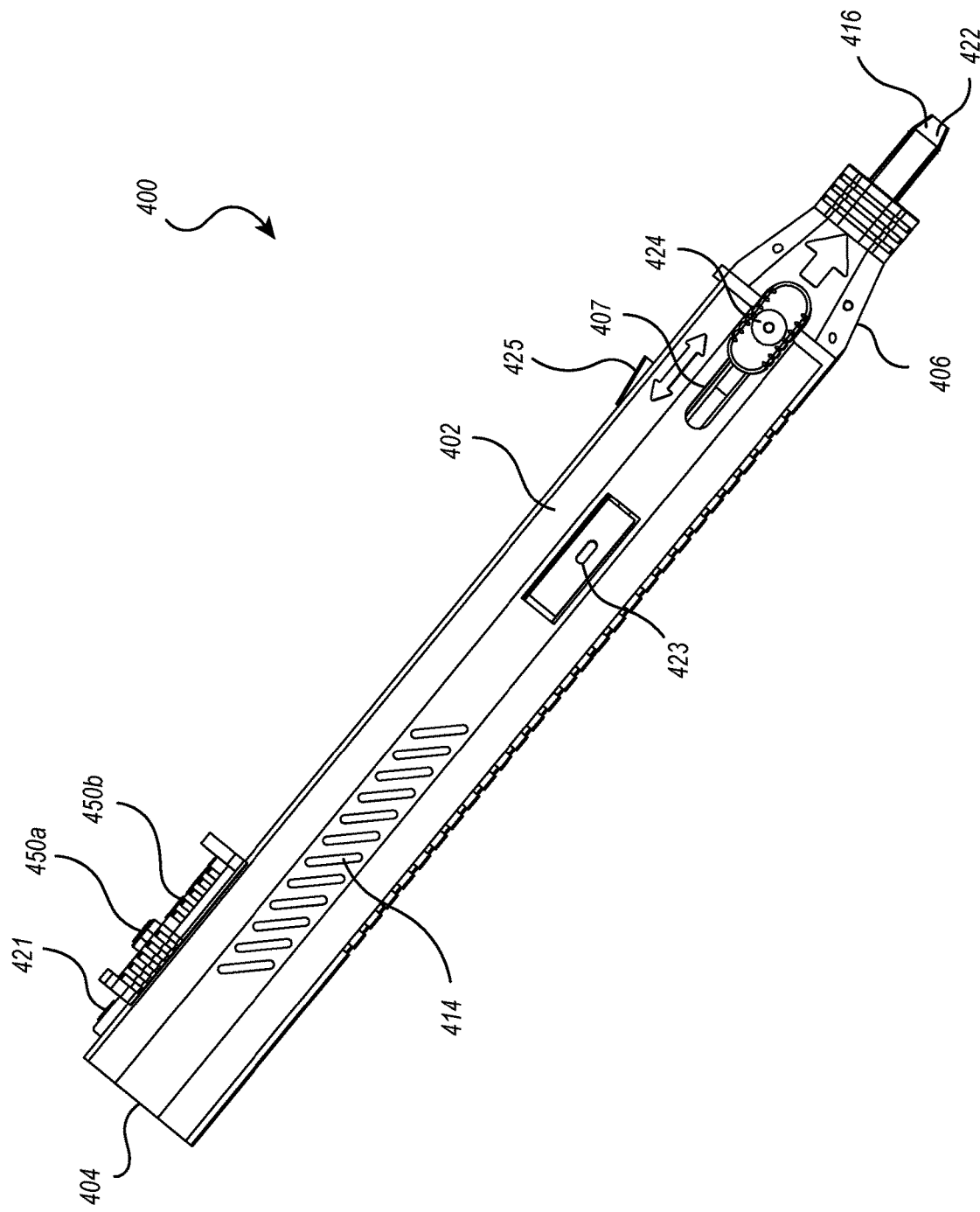
Figure 13C:
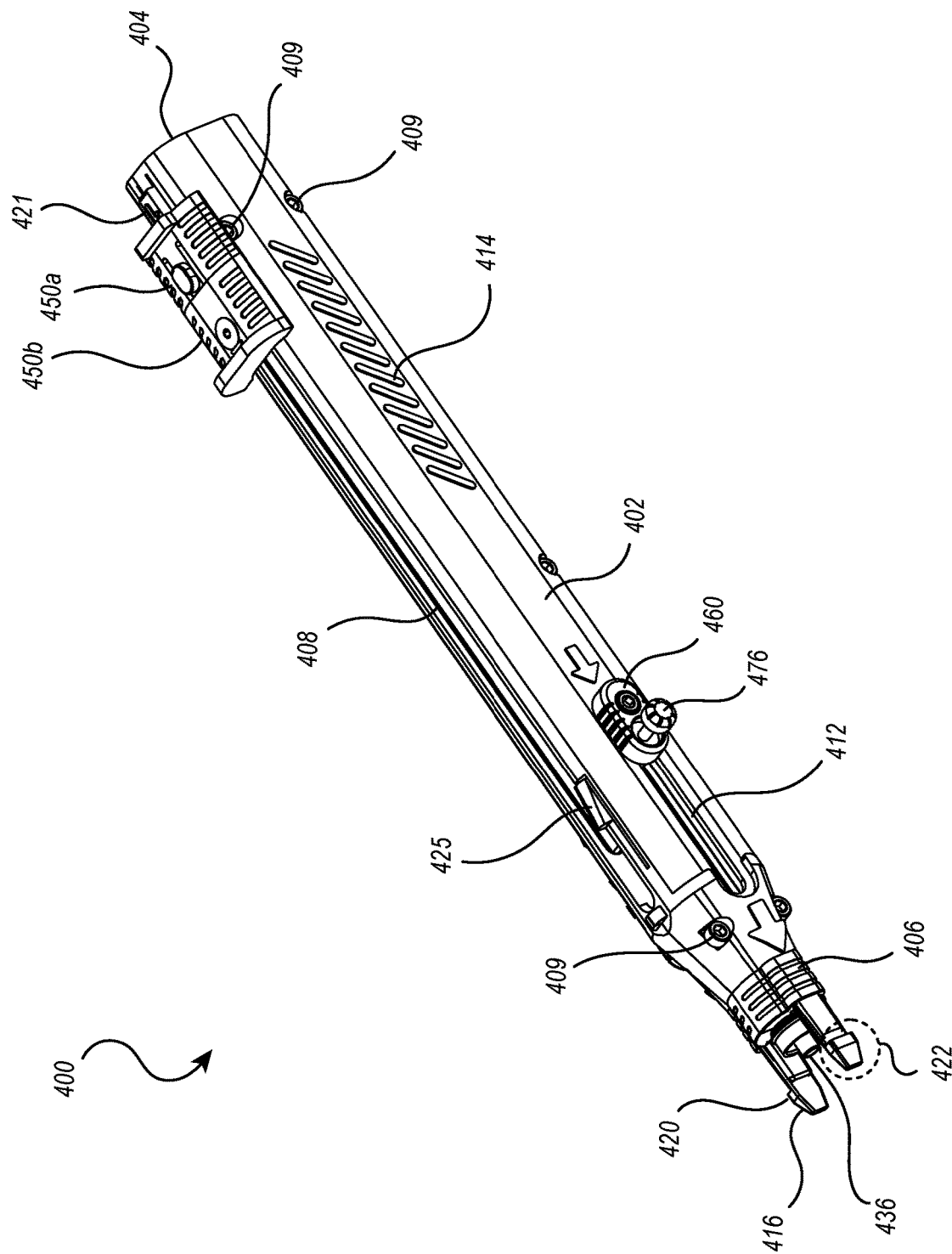
FIG. 13C illustrates a perspective view of the handle assembly of FIGS. 13A and 13B.
Figure 13D:
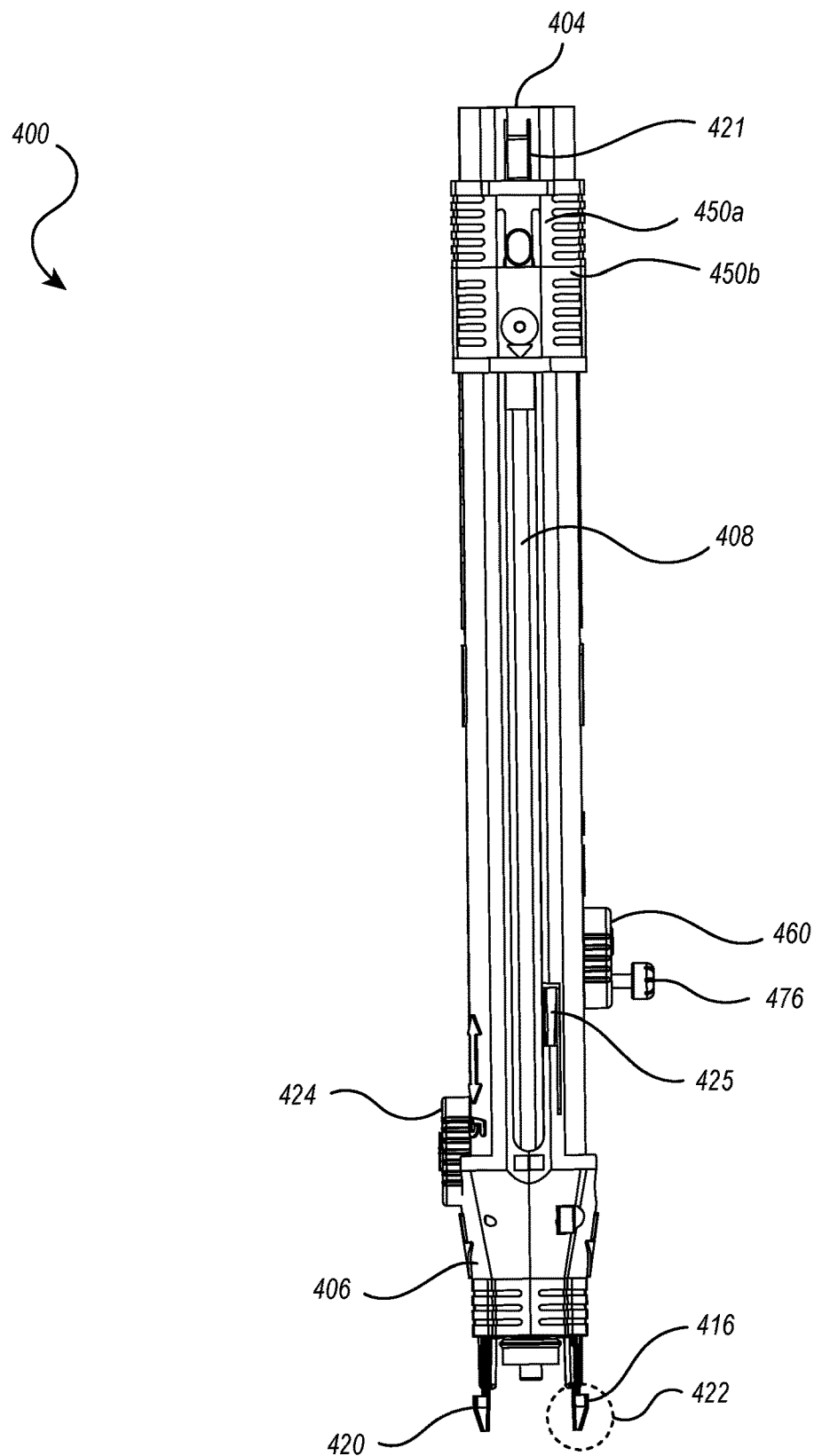
FIG. 13D illustrates a top plan view of the handle assembly of FIGS. 13A-13C.
Figure 13E:
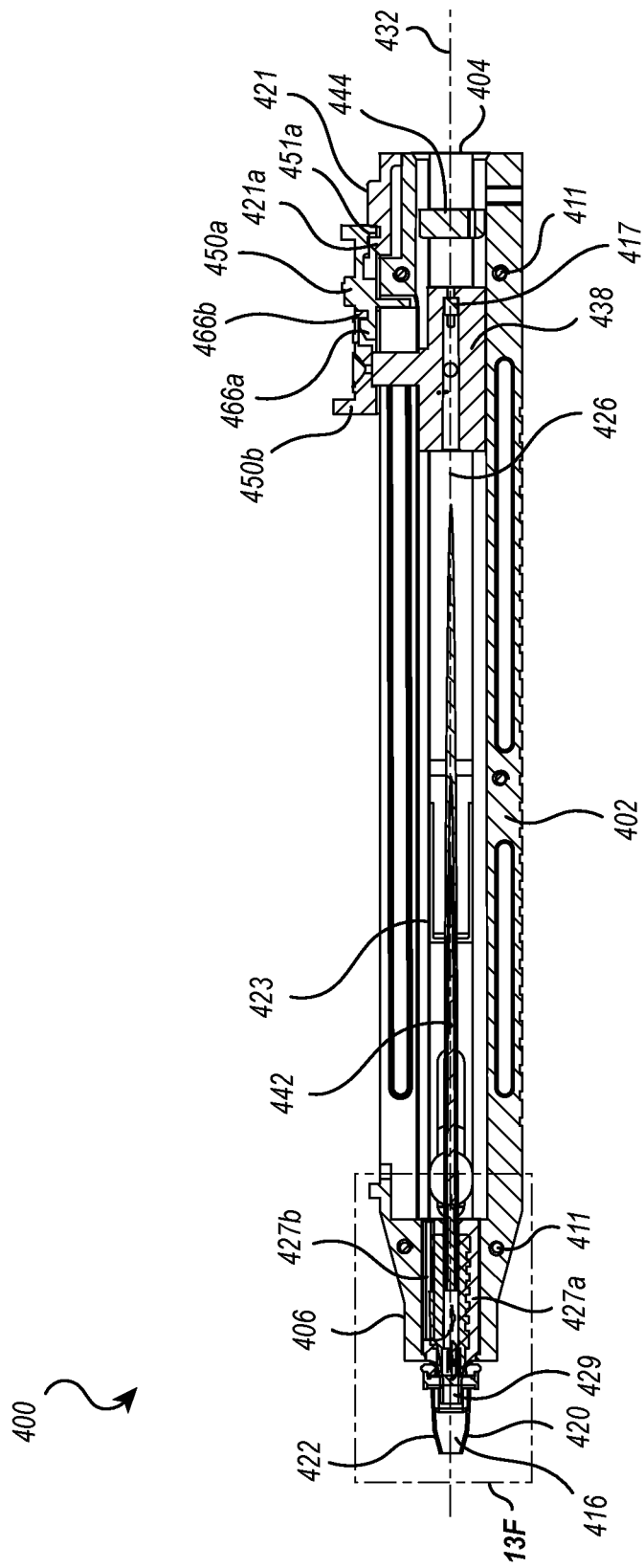
FIG. 13E illustrates a cross-sectional view of the handle assembly of FIGS. 13A-13D.

As shown in FIGS. 12-13E, the handle assembly 400 can include a handle body 402 having a proximal end 404 and a distal end 406, an actuator, such as slider 450, and an elongate opening 408 configured to provide a track for the slider 450. The slider 450 can be configured to slide along the elongate opening 408 when engaged by a user and be selectively locked in place by the locking assembly 425. This engagement can deploy the closure device 100. The handle assembly 400 can also include a second slider 460 (see FIG. 13A) configured in a second elongate opening 412 on the handle body 402. Engagement of the slider 450 can deploy the anchor 108, and then engagement of the second slider 460 can deploy the cap 102.

In other embodiments, the handle assembly 400 may only have one actuator element, such as slider 450, which when engaged can subsequently deploy the anchor 108 and cap 102 without the need for a second slider.

In some embodiments, such as the embodiment shown in the drawing, the handle body 402 can include one or more textured portions 414 to improve a user's grip on the handle assembly 400. The handle assembly 400 can further include a connecting member 416 located at the distal end 406 of the handle body 402 and configured to be selectively attached to and removeable from a delivery sheath 440. The connecting member 416 can be configured to attach to a sheath hub 418 of a delivery sheath 440. The connecting member 416, as shown in FIGS. 13A-13F, comprises a set of locking members 420 having hooked ends 422. The locking members 420 can be configured to selectively attach to the sheath hub 418 of a delivery sheath 440, which attaches the handle assembly 400 to the delivery sheath 440 to form the delivery system 430.

The handle assembly 400 can also include a release button 424 which can release the suture 106 once the closure device 100 is placed at a desired location. Engagement of the release button 424 can release the delivery system 430 from the implanted closure device 100. The release button 424 can include an engagement element such as release button fin 419. The release button fin 419 can fit within release groove 407 and can be configured to slide within the length of groove 407 to release the suture 106 of the closure device 100 from the handle assembly 400. In other embodiments, the functions of the release button 424 may be incorporated into one or more actuator elements such as slider 450 and/or secondary slider 460.

FIG. 13E illustrates a cross-sectional view of the handle assembly 400. As shown in the Figures, slider 450 can include a first slider portion 450*a* and a second slider portion 450*b*. Slider portions 450*a*,450*b* can be selectively connected together by interlocking ends 466*a*,466*b*. A proximal locking assembly 421 can engage slider 450 to "lock" slider 450 at the proximal end 404 of the handle assembly 400. For instance, complementary structures 421*a* and 451*a* on the proximal locking assembly 421 and the slide portion 450*a* of the slider 450 can engage to limit movement of the slider 450, while depressing the proximal locking assembly 421 detaches or separates the complementary structure 421*a* from the complementary structure 451*a* to allow the slider 450 to move distally. The slider portions 450*a*,450*b*, interlocking ends 466*s*,466*b* and proximal locking assembly 421 can be made of a resilient material, such as flexible plastic, to allow the components to flex when depressed by a user. For example, a user can depress proximal locking assembly 421 to release slider 450 and allow the slider 450 to slide along elongate groove 408. The proximal locking assembly 421 can be formed with the handle body 402, such as having a living hinge connection with the handle body 402 or can be a separated mechanism connected or mounted to the handle body 402.

Figure 14A:
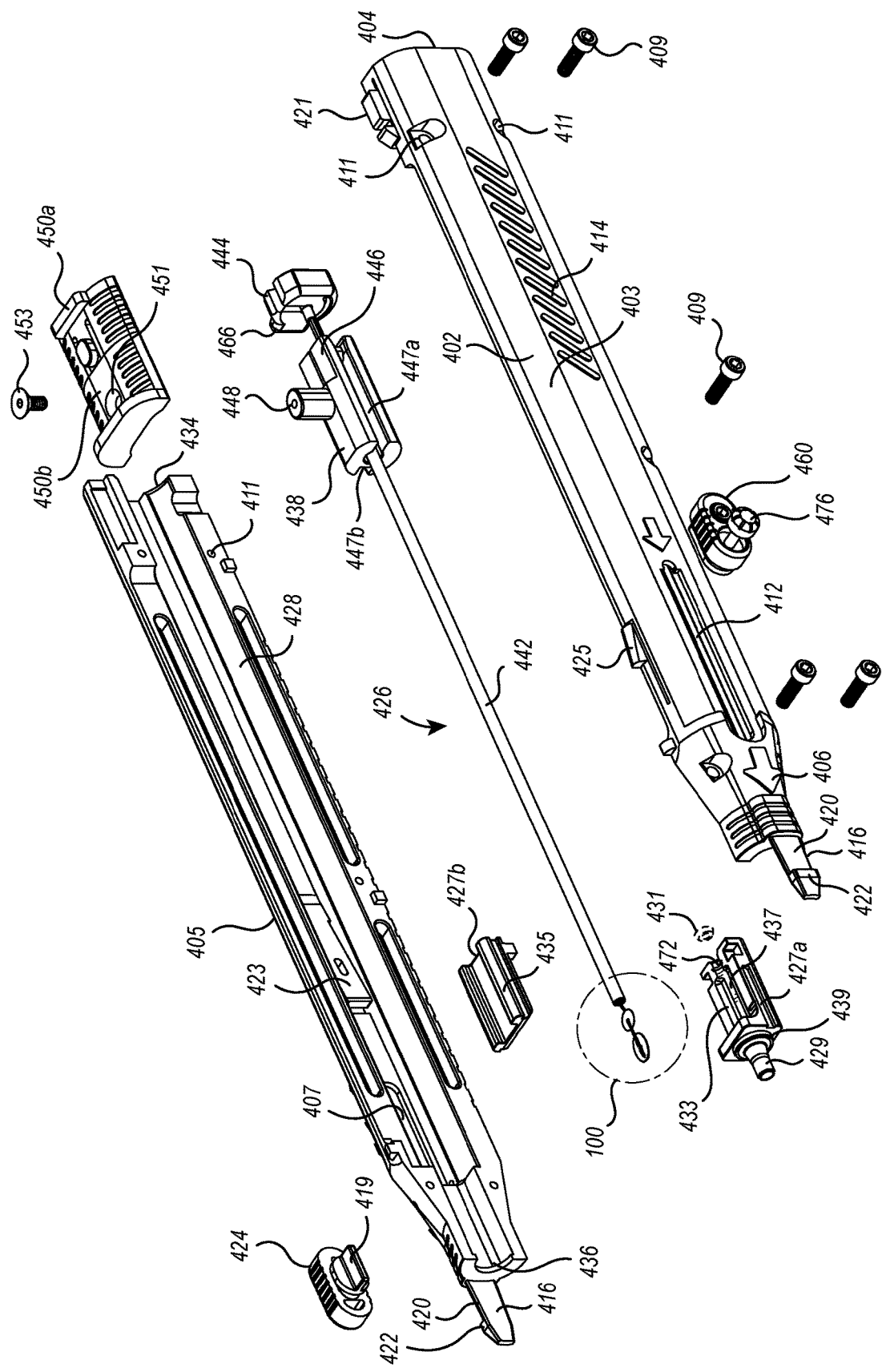
FIG. 14A illustrates an exploded view of the handle assembly of the delivery system.
Figure 14B:
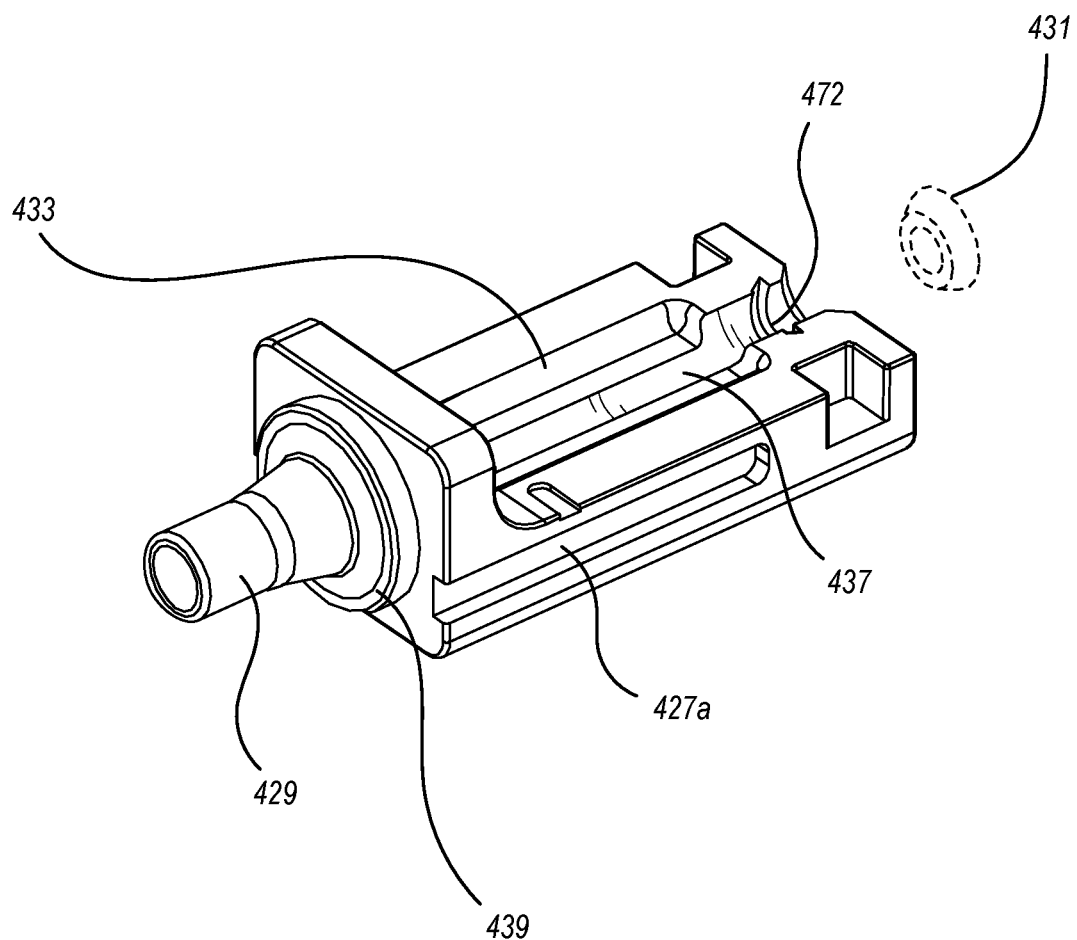
FIG. 14B illustrates an enlarged view of a chamber of the handle assembly of FIGS. 12-14A.
Figure 14C:
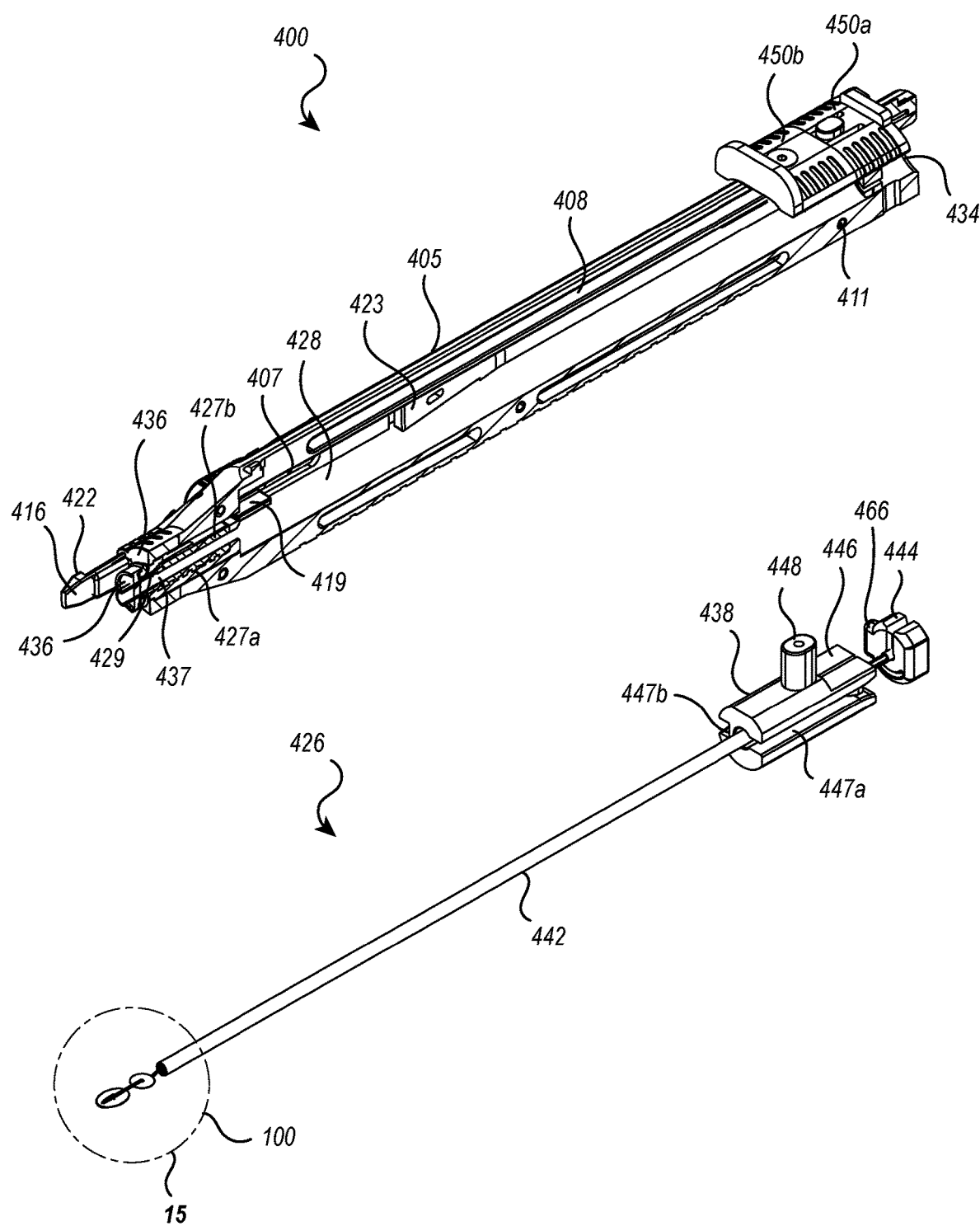
FIG. 14C illustrates a cross-sectional view of the handle assembly of FIGS. 13A-13E with an implant assembly removed from the handle assembly.

FIGS. 14A and 14C illustrate an exploded view of the handle assembly 400. The handle body 402 can comprise a first side 403 and a second side 405, which when assembled together form the lumen 428 of the handle body 402. The first side 403 and second side 405 can be assembled together to form the handle body 402 by using fasteners, such as screws 409 inserted into corresponding bores 411.

Figure 13F:
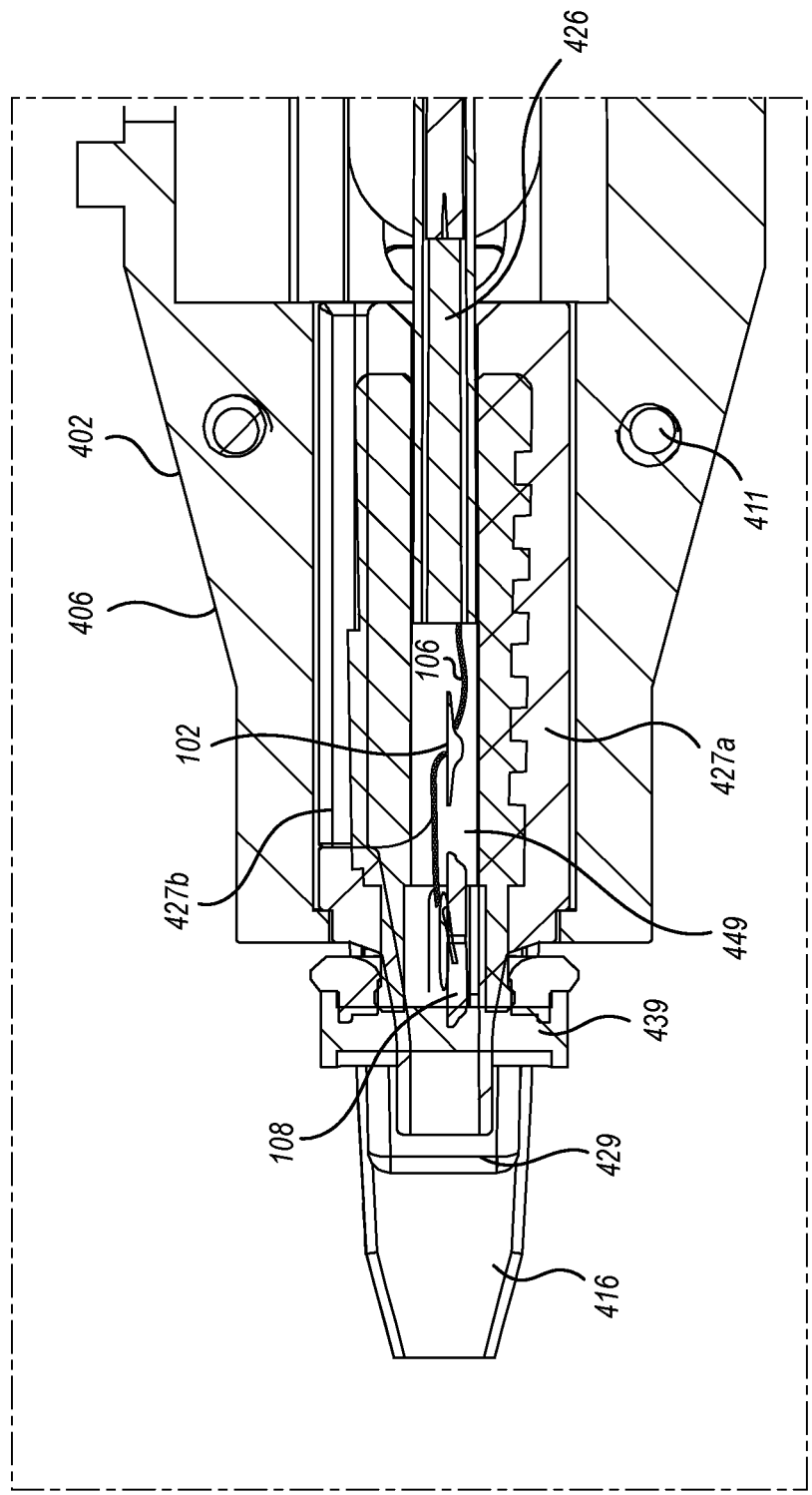
FIG. 13F illustrates an enlarged view of 13F of the handle assembly as shown in FIG. 13E.

The handle body 402 can also house a chamber assembly 427 having a chamber body 427*a* and a chamber cap 427*b* as shown in FIGS. 13F and 14B, which can be disposed at the distal end 406 of the handle body 402. While the chamber assembly 427 is illustrated as two pieces, it will be understood that the chamber assembly 427 can utilize less or more pieces to form an assembly that can provide the functions described herein. The chamber assembly 427 can also be formed separately from the handle body 402, as shown, though in other embodiments, the chamber assembly 427 may be integrally formed within the handle body 402. The chamber assembly 427, and in particular the chamber body 427 can align with the lumen 428 and the distal opening 436 to form a channel 437 through which the implant assembly 426 can deploy the closure device 100.

The chamber assembly 427 can include a chamber body 427*a* with a nozzle 429 and a nozzle ring 439. The nozzle 429 and ring 439 can be shaped to interface with the delivery sheath 440 and form a fluid-tight seal. The implant assembly 426 can be deployed from the lumen 428 through the channel 437 and then out of the nozzle 429 of the chamber assembly 427, such as from the chamber body 427*a*, into the delivery sheath 440. In some embodiments, the chamber assembly 427 can include a valve 431. The valve 431 can be a one-way valve, preventing fluids from entering the lumen 428 of the handle body 402. The valve 431 can be seated within a valve notch 472 at the proximal end of the chamber body 427*a*. The chamber body 427*a* can also include a plateau 433. The chamber assembly 427 as shown includes a chamber cap 427*b*. The chamber cap 427*b* can be situated on top of the chamber 427 in the distal end 406 of the handle body 402. The chamber cap 427*b* can help form the channel 437 and can include one or more positioning elements 435 which can retain the chamber cap 427*b* in the correct orientation and location in the handle body 402. The chamber body 427*a* and the chamber cap 427*b*, when connected or coupled together, form a cavity 449 to receive the closure device, as illustrated in FIG. 13F. The cavity 449 communicates with, and forms part of the lumen 428.

An implant assembly 426 is contained within the handle body 402. The implant assembly 426 houses the closure device 100 and other elements required to place the closure device 100. The implant assembly 426 can be configured to be positioned within the lumen 428 of the handle body 402. The lumen 428 can extend from a proximal opening 434 of the proximal end 404 along a longitudinal axis 432 and terminate at a distal opening 436 on the distal end 406 of the handle body 402. The implant assembly 426 can be situated within the lumen 428 so that it can be in mechanical communication with elements of the handle body (i.e., slider 450 and secondary slider 460).

The implant assembly 426, shown in detail in FIGS. 14A, 14C-14F, 15 and 16, includes a closure device such as closure device 100, a support tube 442, a slider 438, and a stopper 444. The slider 438 can comprise a slider body 446 having a protrusion 448 providing for mechanical interface between slider 450 on the external side of the handle body 402 and slider body 446 situated on the implant assembly 426 within the lumen 428 of the handle body 402. The slider 438 can also include a groove 447*a* configured to receive the nested elements (support tube 442, closure device 100, tamper tube 454, and push wire 452) of the implant assembly 426. Slider 438 can also include suture groove 447*b*, which can allow mechanical communication between the implant assembly and the handle body 402 to facilitate release of suture 106 from the implant assembly 426.

The stopper 444 can include a stopper elbow 466 configured to engage with interior locking mechanism 423. When the stopper 444 is moved in a distal direction towards the distal end 406 of the handle body 402 the stopper 444 will pass the interior locking assembly 423. Once past the interior locking assembly 423, the stopper elbow 466 can engage the interior locking assembly 423, preventing the stopper 444 from moving in a proximal direction. The stopper 444 can prevent closure device elements, such as the fluid blocking component 104, from flowing back into the handle assembly 400. The interior locking mechanism 423 can be formed with the handle body 402, such as having a living hinge connection with the handle body 402 or can be a separated mechanism connected or mounted to the handle body 402.

Figure 14D:
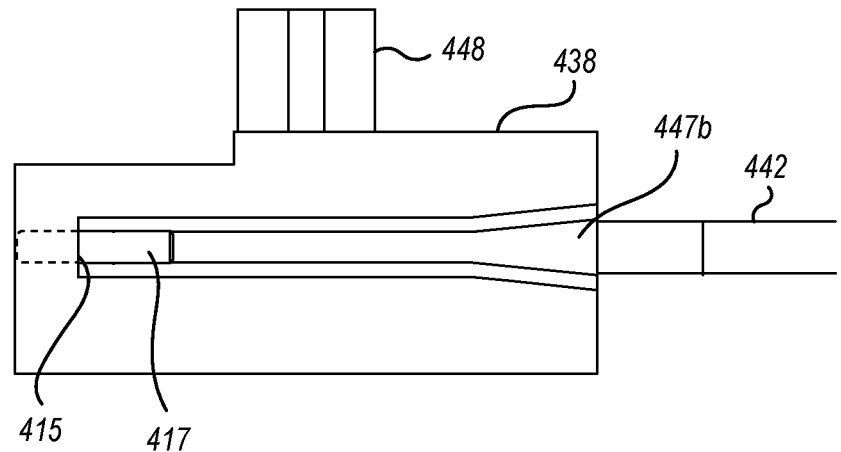
FIG. 14D illustrates a cross-sectional view of a slider of the implant assembly of FIG. 14C.
Figure 14E:
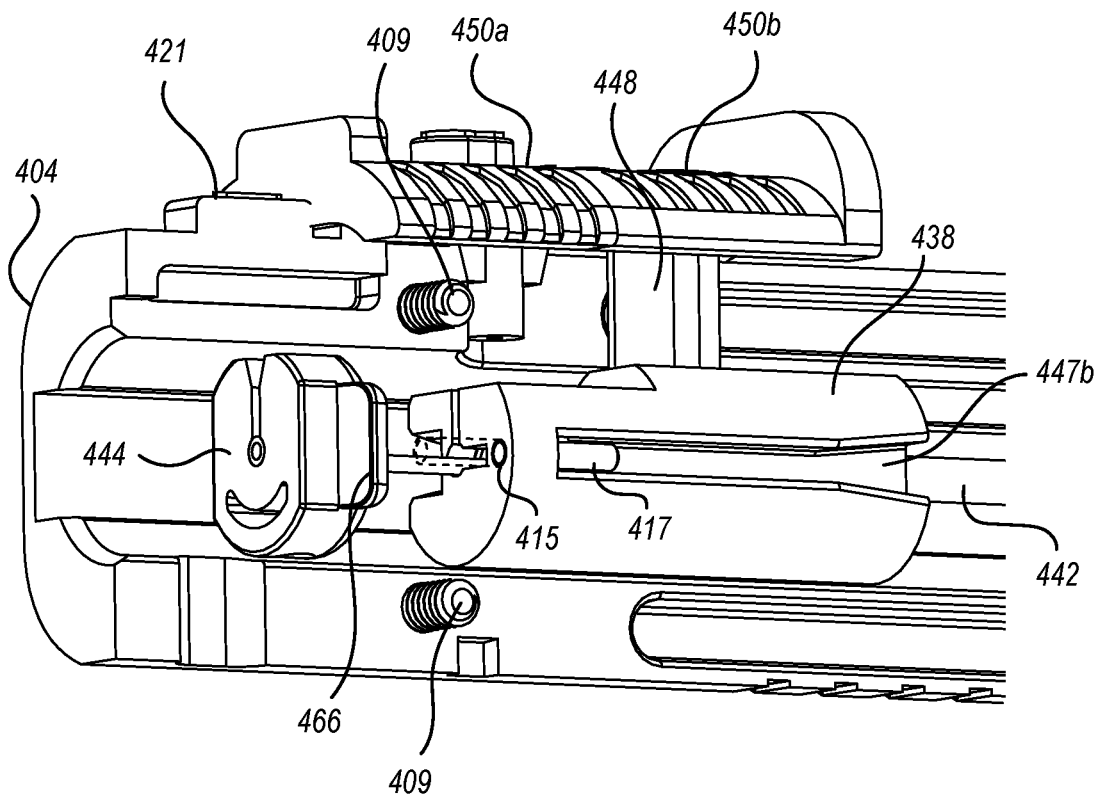
FIGS. 14E and 14F illustrates a perspective views of the slider of FIG. 14D as positioned within a handle body.

FIGS. 14D and 14E illustrate detailed views of slider 438 of the implant assembly 426. As discussed above, the slider 438 can include one or more structures configured to engage with exterior elements of the handle body 402 to control insertion and placement of the closure device 100 and disengagement of the closure device 100 from the delivery system 430. The suture groove 447*b* of slider 438 can house a pin 417 positioned within a bore 415.

Figure 14F:
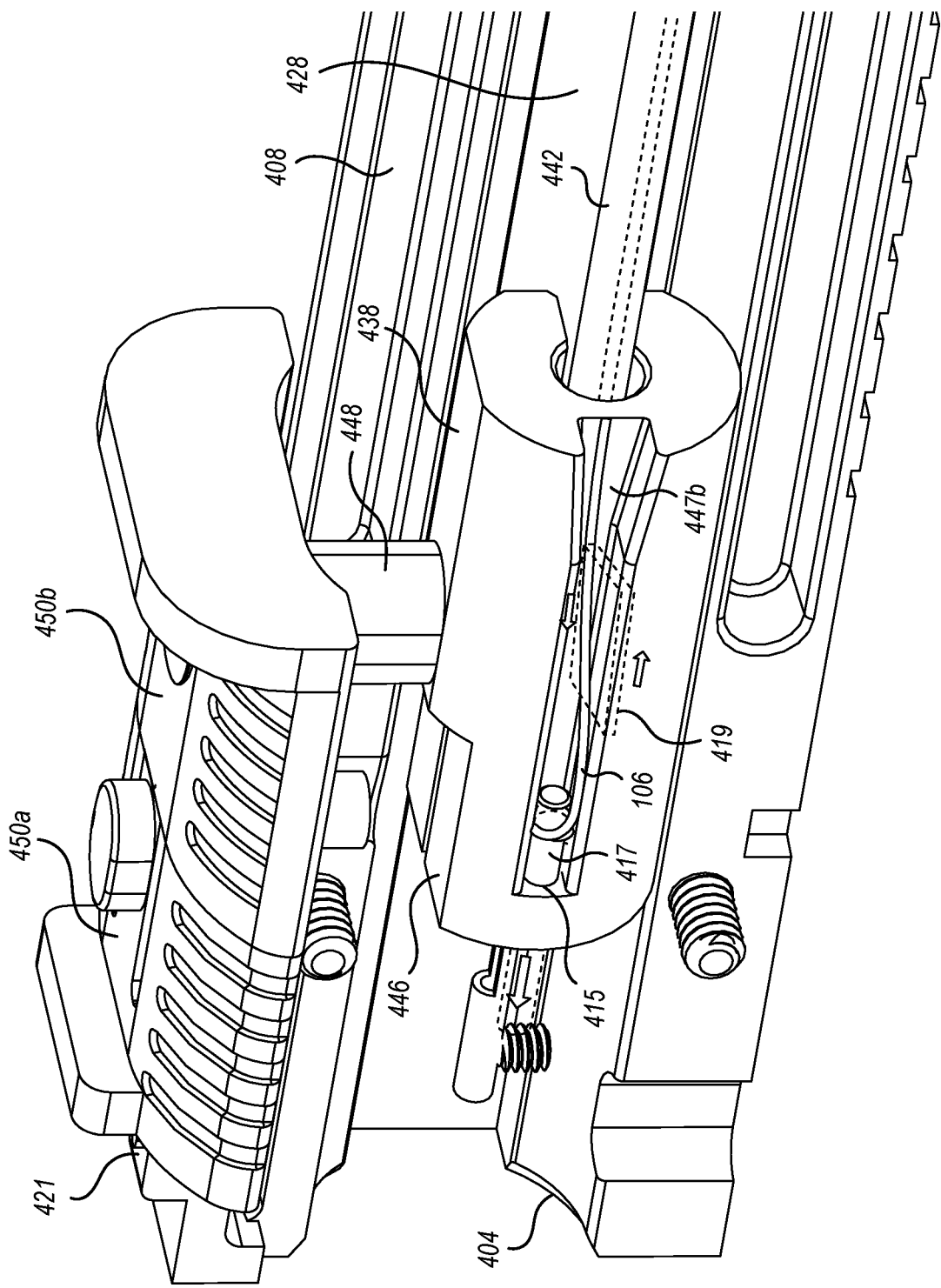

As shown in FIG. 14F, the suture 106 can be looped around the pin 417 during assembly and a friction fit of the suture 106 between the pin and the suture groove 447*b* can retain the suture 106 within the slider 438 during insertion of the closure device 100. After the closure device 100 is deployed to the blood vessel, the delivery system 430 is decoupled from the closure device 100 by releasing the suture 106 from the slider 438. The release button 424 is slid in a proximal direction towards the pin 417, causing the release button fin 419 to push the pin 417 into bore 415. When the pin 417 is pushed into the bore 415, the suture 106 is released from the pin 417, effectively releasing the suture 106 and closure device 100 from the delivery system 430.

The support tube 442 can contain the suture 106 which can be threaded therethrough. The support tube 442 can also contain a push wire 452 and a tamper tube 454. The distal tip 456 of the push wire 452 can have a forked or pronged shape to help push the closure device 100 out of the delivery system 430, while a proximal end includes a push wire bend 477 that mounts to the slider portion 450*a* so that the push wire 452 can be moved through movement of the slider portion 450*a*. The tamper tube 454 can be used to tamp the cap 102 of the closure device 100 after the anchor 108 is positioned. The stopper 444 can prevent the implant assembly 426 from sliding out of the distal opening 436 of the handle body 402. The closure device 100, as discussed above, can comprise an anchor 108, a cap 102, and a fluid-blocking component 104 all configured on a suture 106. The fluid-blocking component 104 can be an active biologic material, such as polyethylene glycol (PEG), fibrin sealants, copolymer of glucosamine and N-acetyl glucosamine, dextran (complex branched glucan(a polysaccharide. polypeptide adhesive structures, adhesive protein containing L-3,4-dihydroxyphenylalanine (L-DOPA), adhesive protein containing DOPA and phosphoserine, collagen, polyacrylic acid, cross-linked with allyl sucrose or allyl pentaerythritol, polyacrylic acid, cross-linked with divinyl glycol, Acrylic resinous polymer composed of methyl-2-cynoacrylate units, or another fully bioabsorbable sealant-type material that could be optionally incorporated into a shaped, flexible substrate. The sealant material could be activated by fluids present in the patient's tissue tract, such as blood or other fluids, and can be protectively stored inside the sheath/actuators or a chamber of the delivery device until positioned directly on top of the cap 102.

Once advanced into the desired location, the sealant 104 can be exposed to the blood or fluid, such as through unsheathing the fluid-blocking component 104 and positioning the fluid-blocking component 104 into direct contact with the tissue where it can react by coming into contact with blood and other fluids. This reaction can cause the fluid-blocking component 104 to expand and absorb blood and other fluids and bond to surrounding tissue and the cap 102. The sealant can act as a glue and aid with "locking" the cap 102 in place on the blood vessel 10, and actively coagulates the entire access tract 22. The chemical formulation, quantity, carrier matrix, and dimensions of the fluid-blocking component 104 can be selected specifically to provide one or more of the functions of locking in place of the sealing component (e.g. cap 102), to provide a fast acting and leak-free dry close, and reduce tissue tract oozing.

For instance, the sealant can form a plug having a length of about 1 mm to about 10 mm and can optionally be trimmed to length in the patient along with the suture after deployment, or the adhesive component can extend the full length of the tissue tract and trimmed to fit the patient. When the fluid-blocking component 104 is formed of a matrix, the matrix can have an area of about 0.012 square inches to about 0.12 square inches, about 0.12 square inches to 0.6 square inches, about 0.6 to 1.0 square inches. The matrix material can be thin and flexible such that it can be wrapped around the suture in the delivery system to fit inside a tube for delivery to the implant location. This results in a volume of fluid-blocking component, optionally including a matrix containing a sealant such as PEG or other biocompatible material, of between about 0.004 to about 0.040 cubic inches in volume, about 0.0.040 to about 0.100 cubic inches, about 0.100 to about 0.400 cubic inches.

The fluid-blocking component 104 can be deployed so that is disposed on the suture 106. The fluid-blocking component 104, therefore, can be deployed in a flowable composition without a carrier matrix or can be formed as part or with a carrier matrix. For instance, the fluid-blocking component 104 can be disposed around the suture 106 in a generally cylindrical component, can be bonded to the suture 106 itself, can be bonded to the cap 102, and combinations or modifications thereof. Because the sealant 104 is positioned proximal relative to the cap 102, the sealant 104 can actively coagulate the access tract 22 and optionally actively coagulate all of access tract 22 to the surface of the skin 16.

Figure 17A:
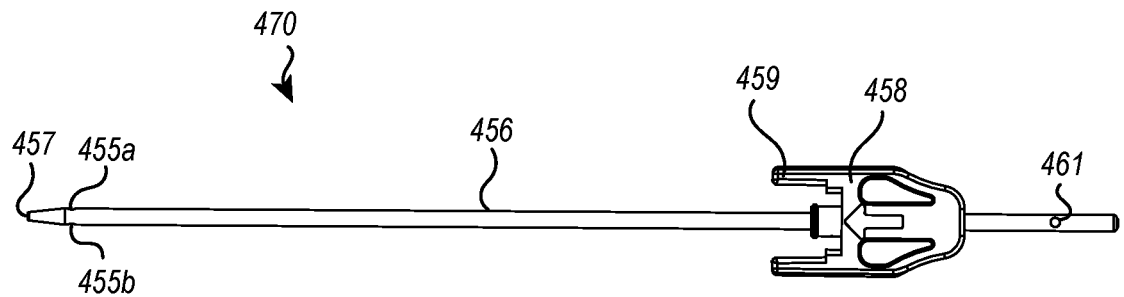
FIGS. 17A and 17B illustrate a dilator tube for implantation of a closure device.
Figure 17B:
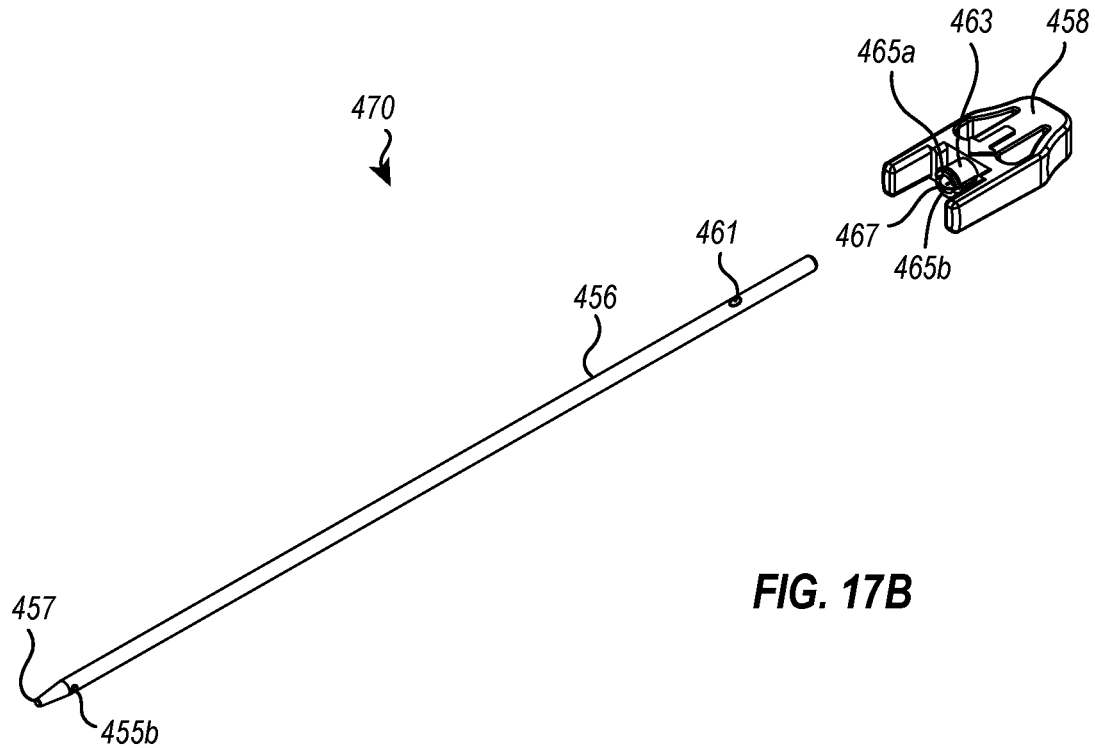

FIGS. 17A and 17B illustrate a dilator assembly 470 having a dilator tube 456 with a dilator hub 458 which can be assembled on the dilator tube 456. The dilator tube 456 can be inserted into the delivery sheath 440 in order to stretch the opening in the skin 16 and access tract 22 to allow for insertion of the delivery sheath 440. The dilator hub 458 can be configured to be selectively attached to and removed from the delivery sheath 440 via the sheath hub 418. The dilator hub 458 can include locking arms 459 which can selectively engage the receiving members 468 of the sheath hub 418, such as through an interference or friction fit. The dilator tube 456 and/or the dilator hub 458 can be formed of biocompatible materials, such as but not limited to nylon, Polyethylene, High Density Polyethylene (HDPE), or other polymeric materials.

The dilator tube 456 includes distal openings 455*a*,455*b* toward a distal end and a proximal opening 461 towards a proximal end. The distal openings 455*a*,455*b* communicate with a passageway 475 to form a fluid marker (e.g., blood marker) to aid with positioning the dilator tube 456 within a body lumen. For instance, a fluid from inside a body lumen, such as blood, is permitted to flow through one or both of the distal openings 455*a*, 455*b* and through the passage 475 and out of the proximal opening 461 to indicate a particular depth. While the distal openings 455*a*, 455*b* are illustrated as being positioned on opposite sides of the dilator tube 456, it will be understood that the location and number of openings can vary.

Disposed between the locking arms 459 is a mounting member 463 that aids with mounting the dilator hub 458 to the delivery sheath 440. The mounting member 463 can be bifurcated with a first leg 465*a* and a second leg 465*b* each having a protruding portion 467. The bifurcated structure allows for flexing of the mounting member 463 as it engages with the delivery sheath 440, while the protruding portion 467 friction or interference fits within the sheath hub 418.

Figure 18A:
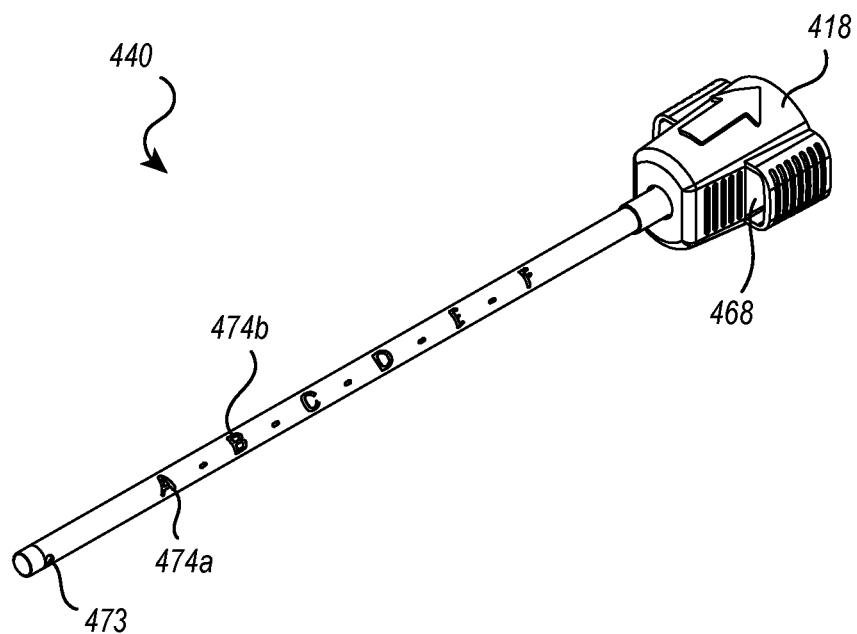
FIGS. 18A and 18B illustrate a delivery sheath of a delivery system.
Figure 18B:
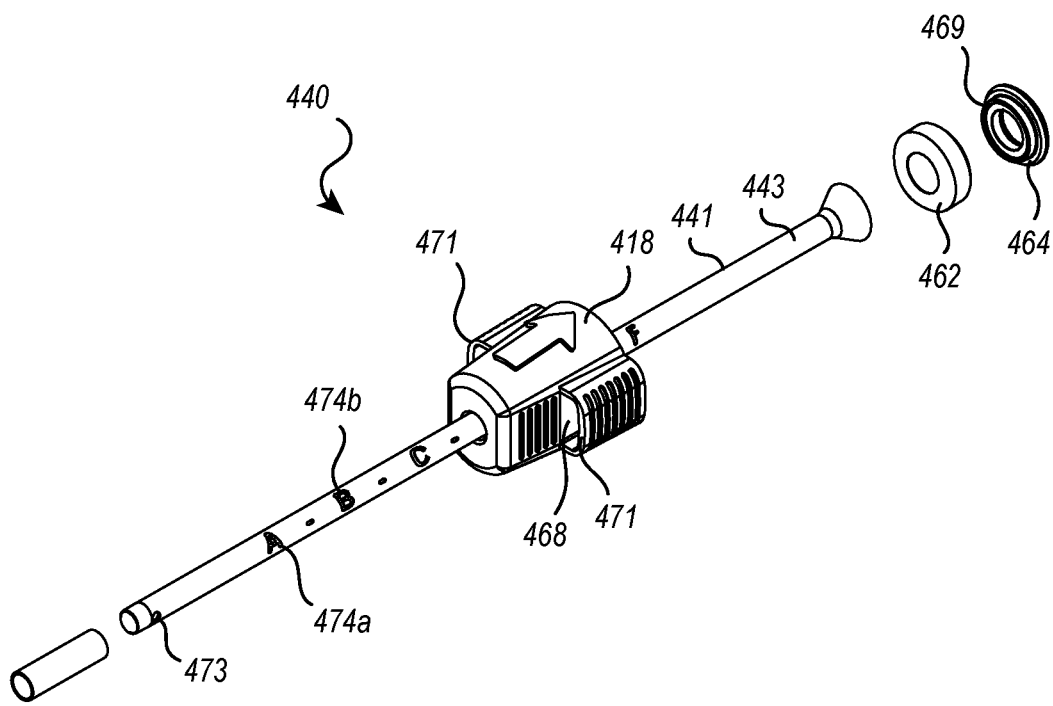

The delivery sheath 440 shown in FIGS. 18A and 18B comprises a sheath 441 for delivering the dilator tube 456 and the implant assembly 426 through the access tract 22. A sheath hub 418 can be assembled on the sheath 441 in order to allow for the selective attachment of other surgical instruments to the delivery sheath 440 such as dilator tube 456. The sheath hub 418 can include receiving members 468 configured to receive surgical instruments and selectively retain the surgical instruments on the delivery sheath 440, such as but not limited to the locking member 420 and the locking arms 459 of the dilator hub 458. The receiving member 468 can be channels or passages formed by a wall 471. The proximal end 443 of the sheath 441 can cooperate with a valve 462 to prevent the backflow of fluid into a surgical instrument attached to the delivery sheath 440. The valve 462 is retained within the sheath hub 418 by a valve cap 464, with a strain relief member 469 extending distally from the sheath hub 418. One or more of the sheath hub 418, the sheath 441, the valve 462, the valve cap 464, the strain relief member 469 can be bonded together through an overmold bond technique or otherwise mounted together using a combination of friction or interference fit and adhesives, thermal, chemical, or other bonding techniques.

When the dilator assembly 470 is mounted to the delivery sheath 440, the mounting member 463 passes through the valve cap 464 and the valve 462. With one or more ports 473 aligned with the distal openings 455 a fluid pathway is formed to allow for depth determination and location of the delivery sheath 440. Additionally, indicia 474 are provided on the sheath 441 to provide a depth indication for the delivery sheath 440. For instance, letters, numbers, or other symbols can be used to identify insertion depth. In one configuration, first indica 474a, can be separated by about 1 cm, with a second indica 474b being about 0.5 cm from the adjacent first indicia 474a. It will be understood that one or more second indica 474b can be disposed between adjacent first indica 474a, thereby changing the depth granularity. Additionally, the separation of the first indica 474a can range from about 0.1 cm to about 5 cm, from about 0.25 cm to about 2.5 cm, about 0.5 cm to about 1 cm, less than about 5 cm, less than about 4 cm, less than about 3 cm, less than about 2 cm, less than about 1 cm, less than about 0.5 cm.

Figure 19A:
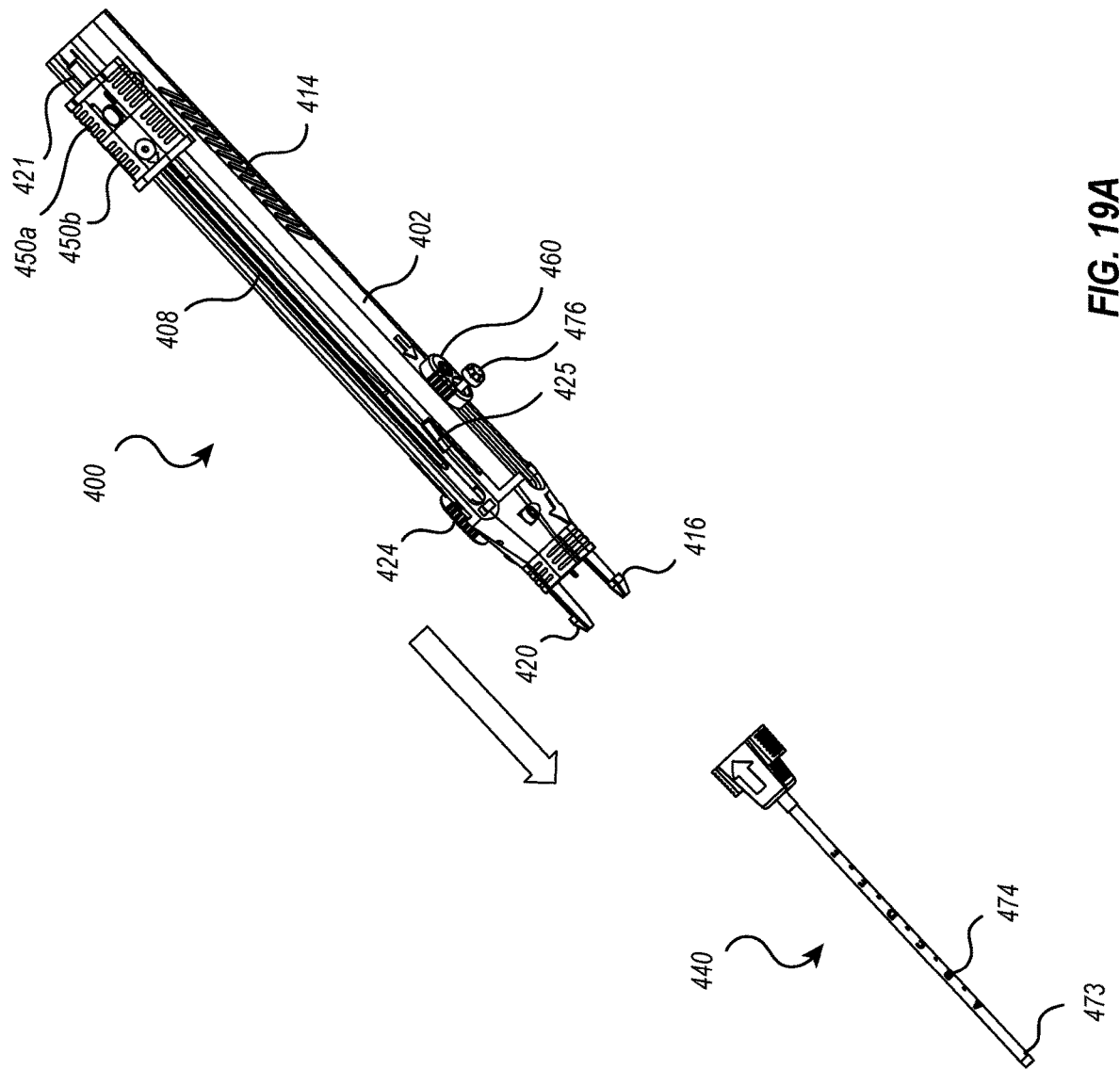
FIGS. 19A and 19B illustrate the insertion and attachment of a handle assembly to a delivery sheath.
Figure 19B:
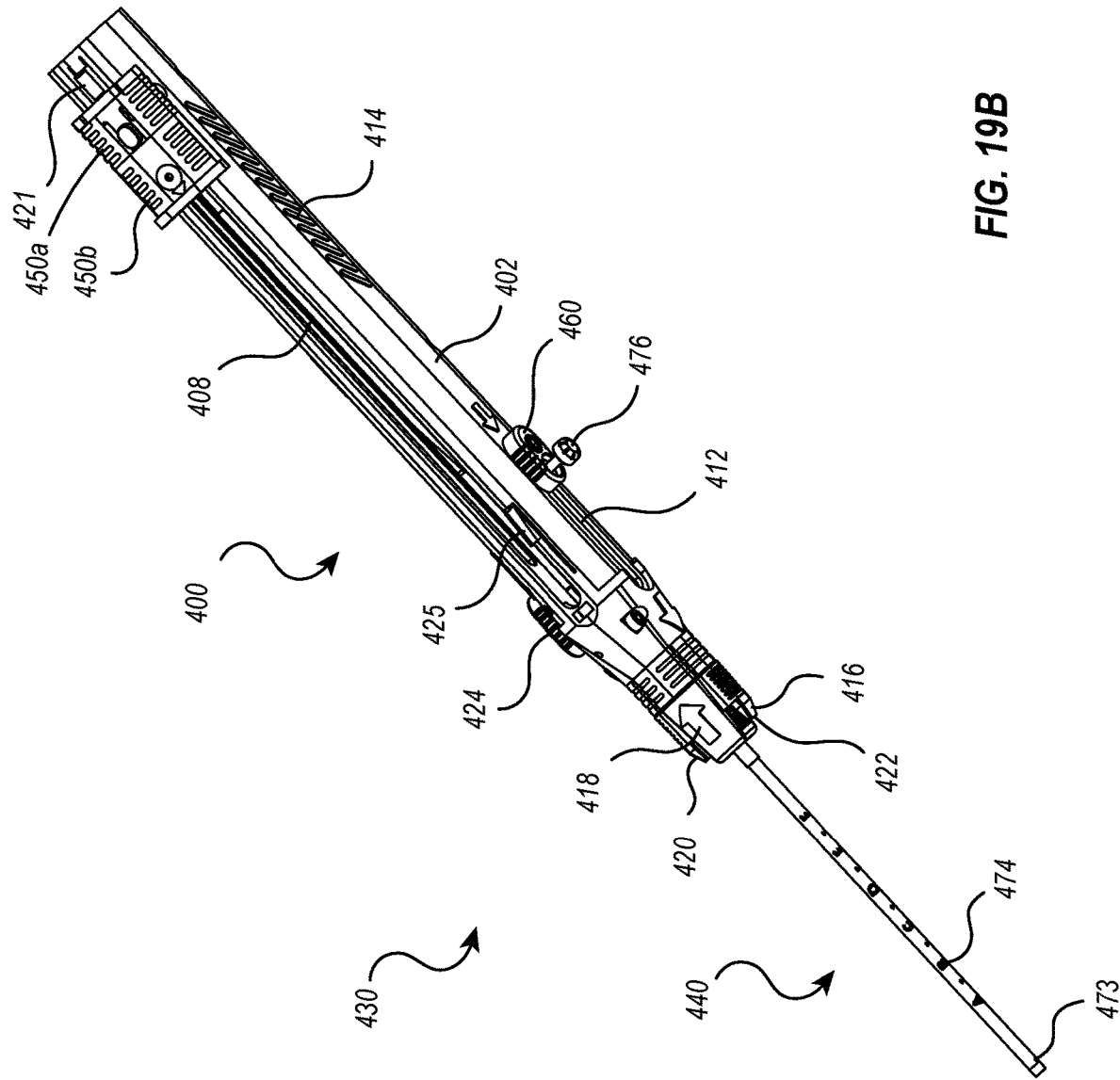

As shown in FIGS. 19A and 19B, the handle assembly 400 can be selectively attached to the delivery sheath 440 by inserting locking members 420 of the handle assembly 400 into the receiving members 418 of the delivery sheath to form the delivery system 430. The locking members 420 can be made of a resilient material, such as flexible plastic, to allow the locking members 420 to flex when inserted into the receiving member 418. The locking members 420 can be flexed to disengage the hooked ends 422 to decouple the handle assembly 400 from the delivery sheath 440. As the locking members 420 cooperate with the receiving members 468, the chamber nozzle 429 penetrates the valve 462 to provide access to the sheath 441 for delivery and deployment of the closure device 100. When the delivery system 430 is engaged to deploy the closure device 100, as in FIG. 19C, the slider 450 can be moved in a distal direction towards the delivery sheath 440, which can cause the anchor 108 of the closure device 100 to be deployed.

Figure 19C:
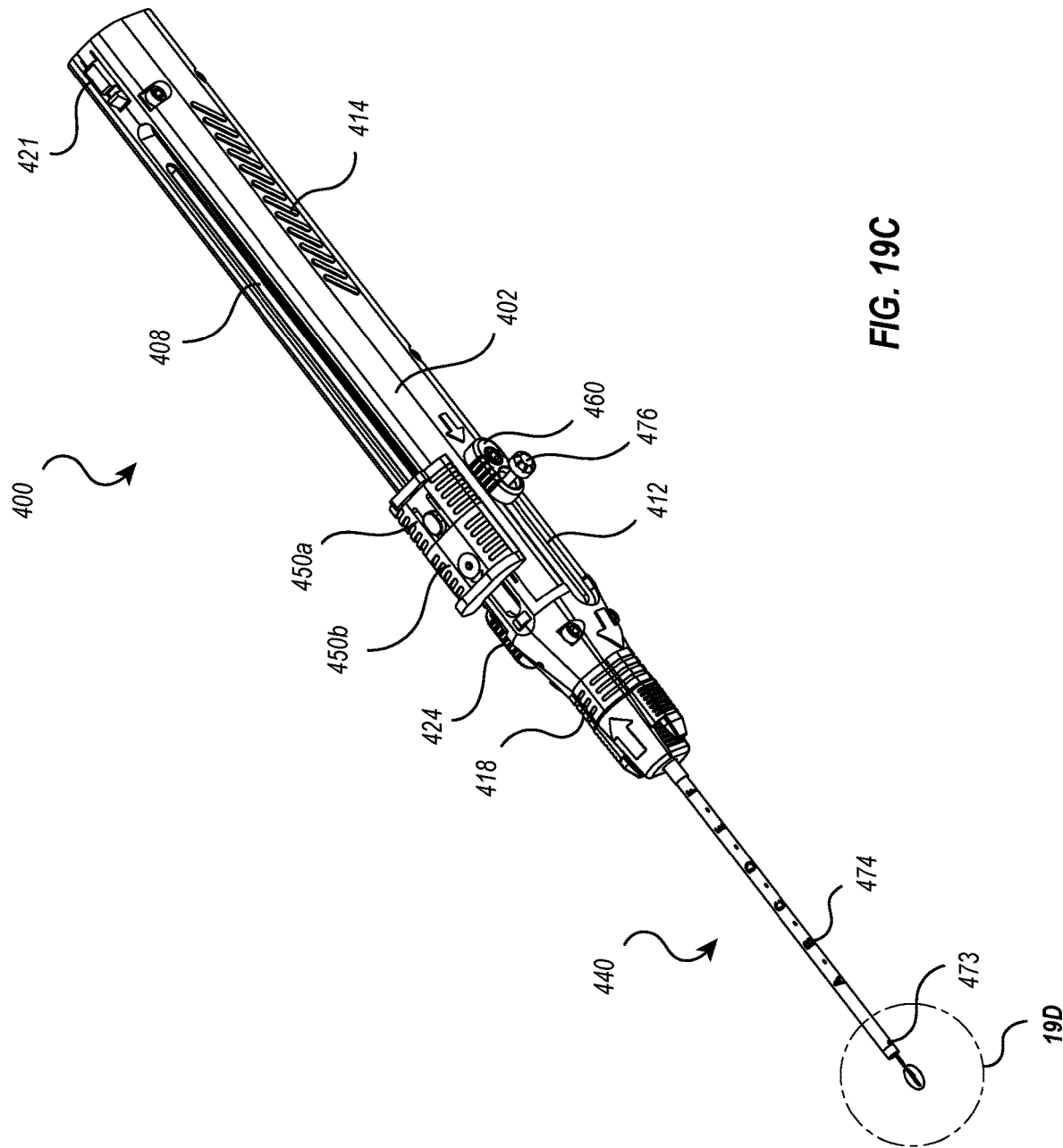
FIG. 19C illustrates the delivery system of FIG. 19A in a partially-deployed state.
Figure 19D:
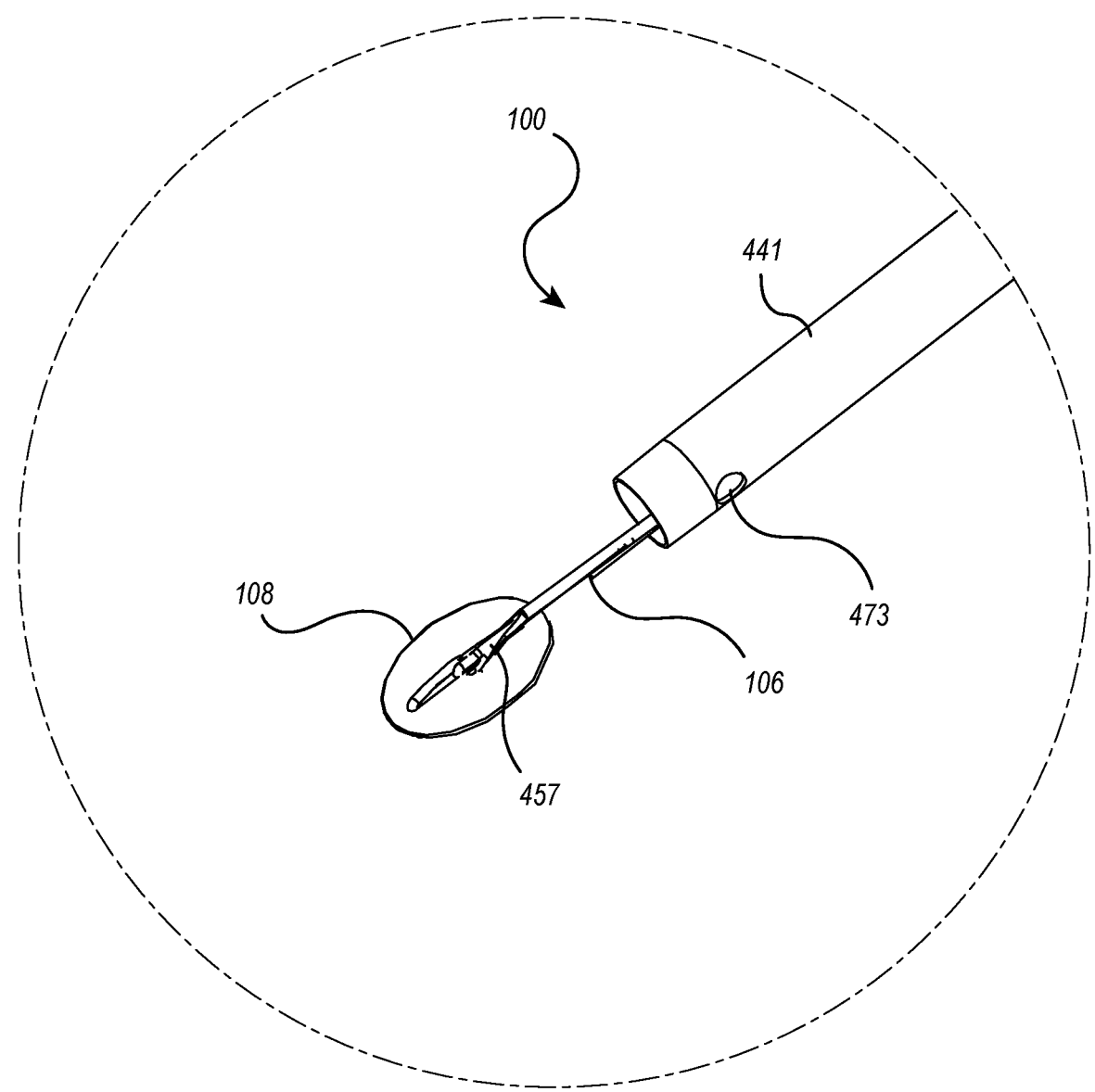
FIG. 19D illustrates a close up view of the implant assembly partially deployed from the delivery sheath as shown in FIG. 19B.

FIG. 19D illustrates a close-up view of the partially-deployed closure device of FIG. 19C. The forked end 457 of the push wire 454 deploys the anchor 108 of the closure device 100 out from the delivery sheath 441.

Method of Closure Device Insertion with Handle Assembly

Figure 20A:
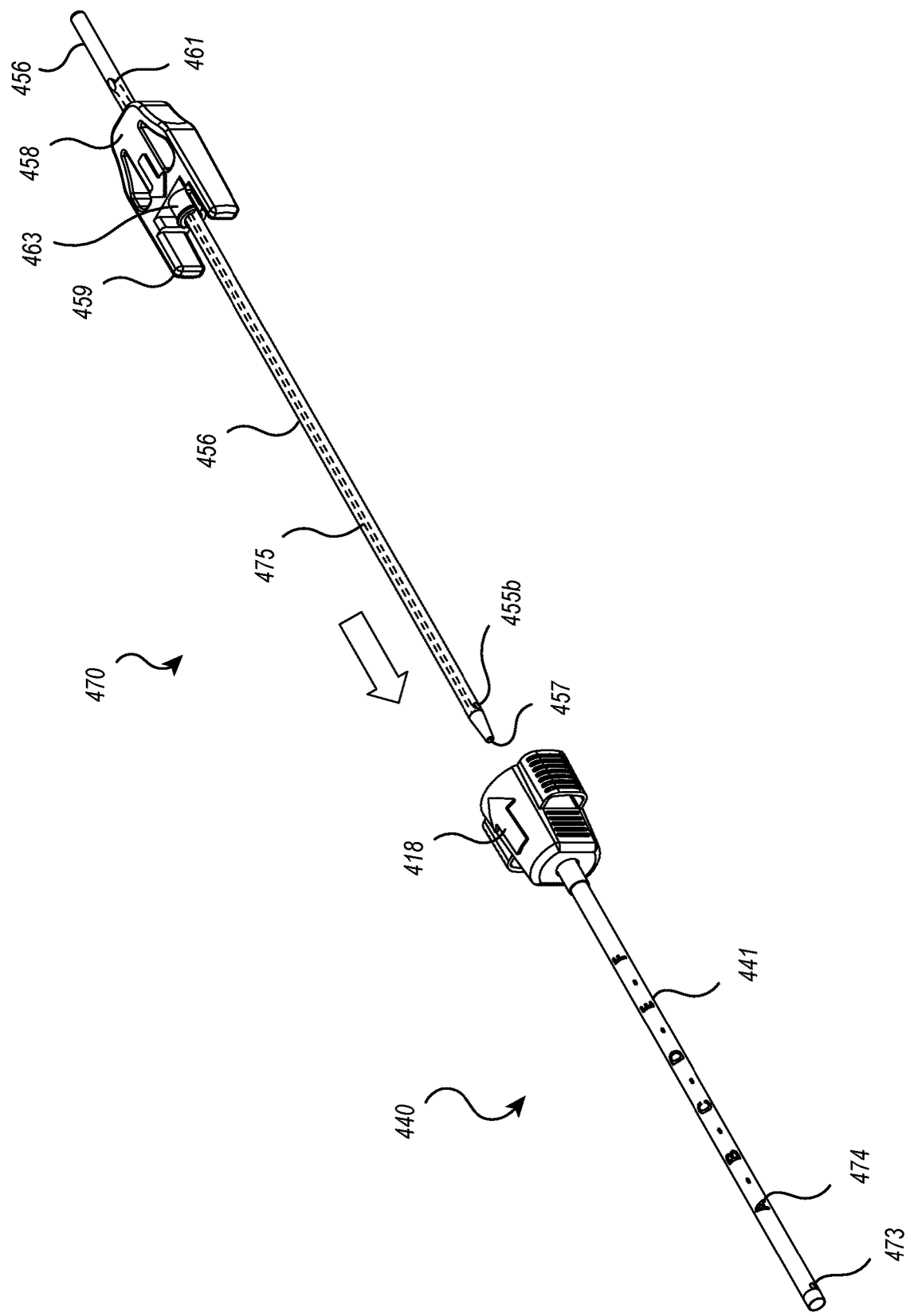
FIGS. 20A-20B illustrate a dilator tube being inserted into a deliver sheath according to a method of delivering a closure device to an access site on a vessel.
Figure 20B:
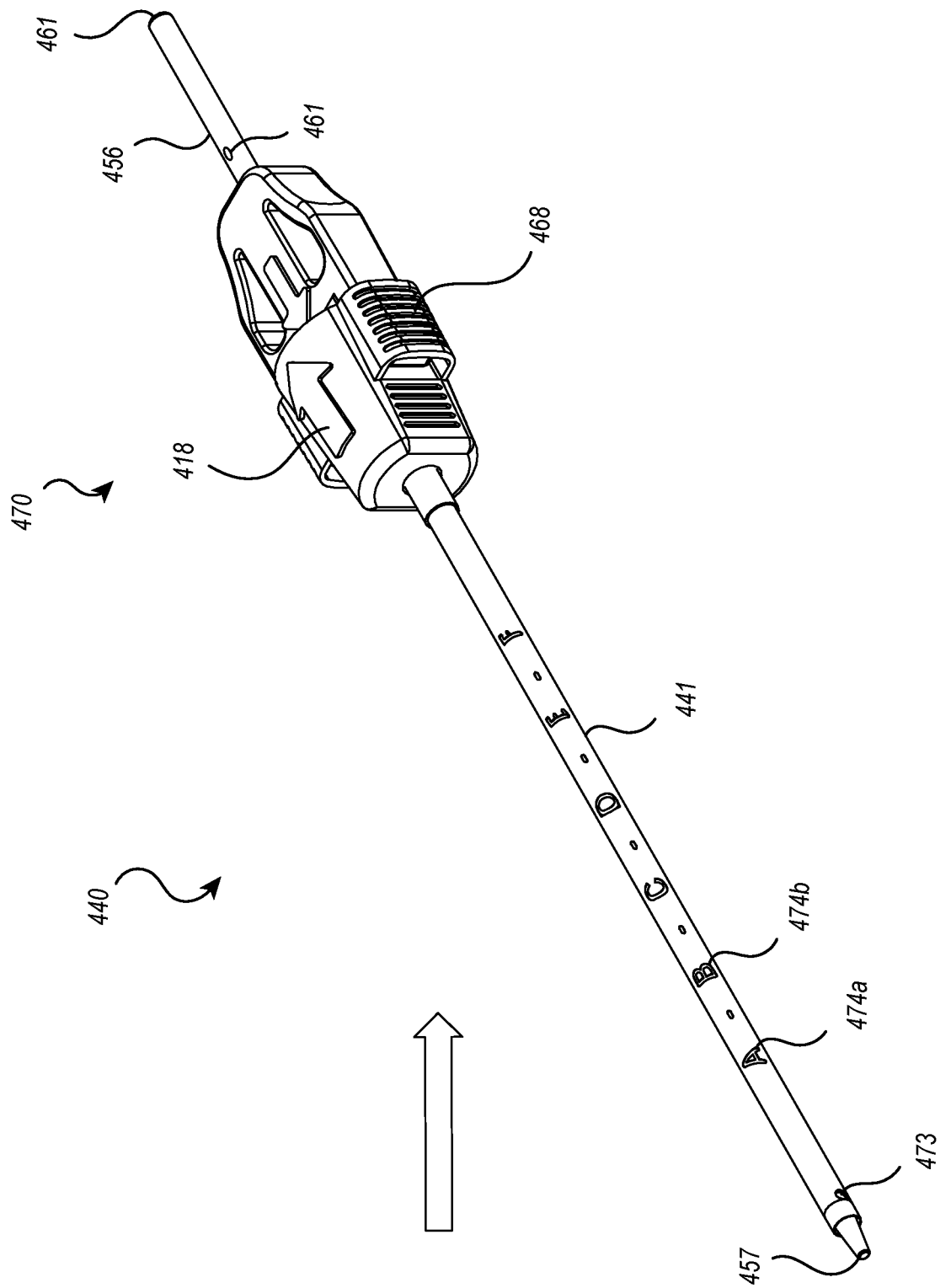

FIGS. 20A through 23C illustrate an example of a method of inserting a closure device using deployment system 430. First the dilator tube 456 can be inserted into the delivery sheath 440. The dilator tube 456 can be selectively attached to the sheath 441 by connecting the dilator hub 458 to the sheath hub 418 in order to maintain the position of the dilator tube 456 in the delivery sheath 440 (FIGS. 20A-20B). The dilator tube 456 can be used to stretch the opening of the skin 16 and access tract 22 to allow for placement of a closure device 100.

Figure 21A:
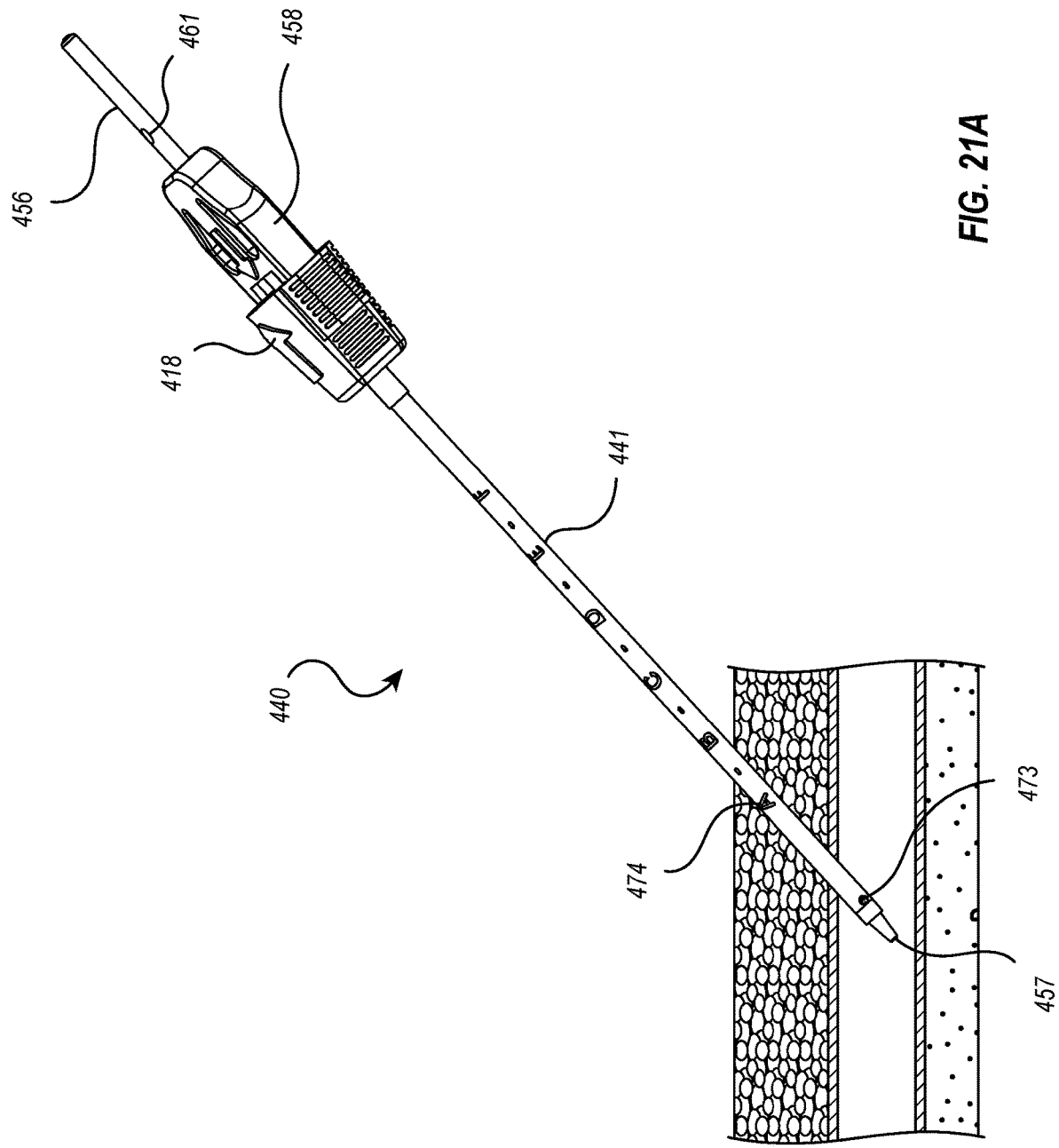
FIG. 21A illustrates the combination dilator tube and delivery sheath being inserted through a tissue tract according to according to a method of delivering a closure device to an access site on a vessel.
Figure 21B:
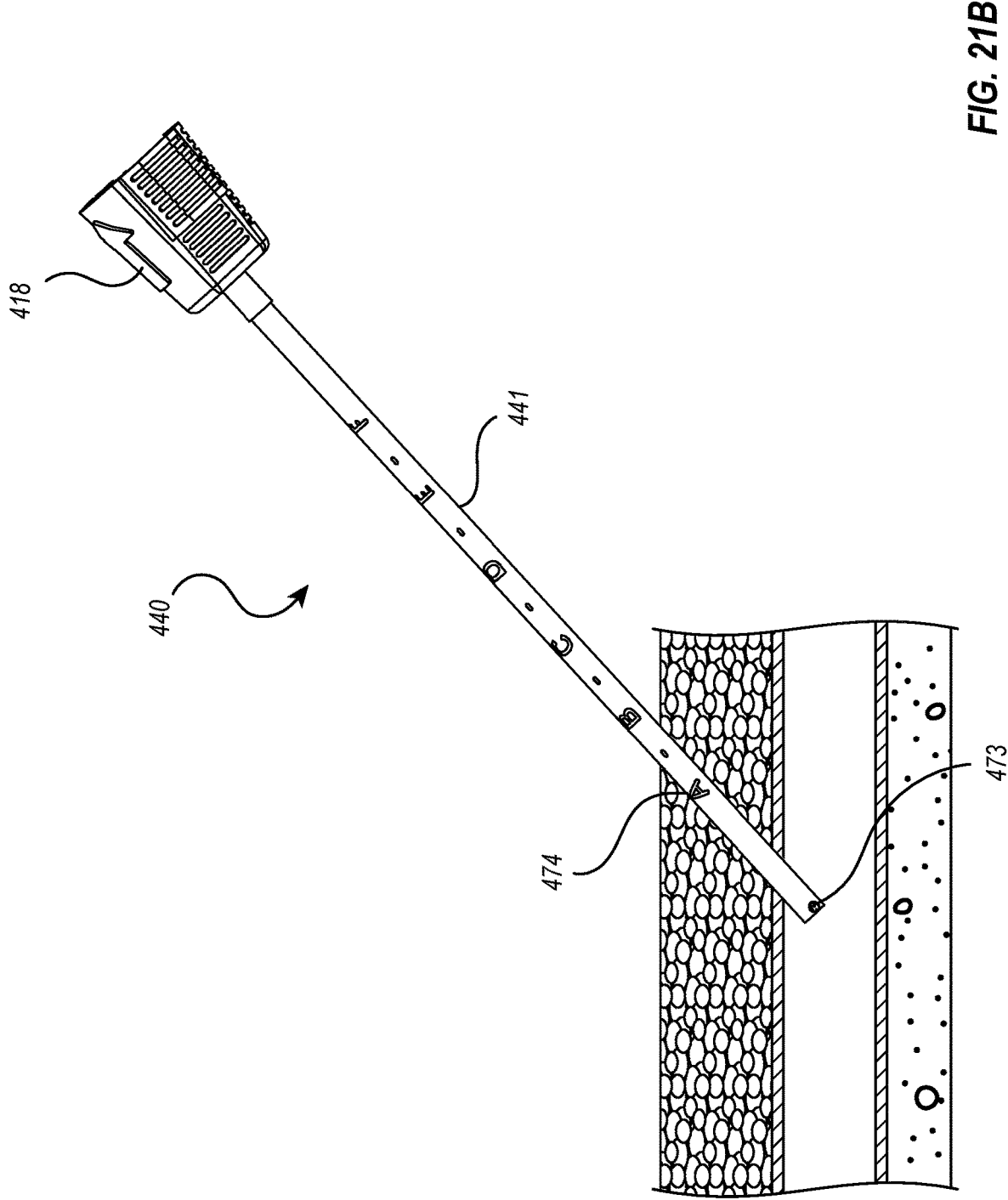
FIG. 21B illustrates the delivery sheath in the tissue tract according to a method of delivering a closure device to an access site on a vessel.
Figure 21C:
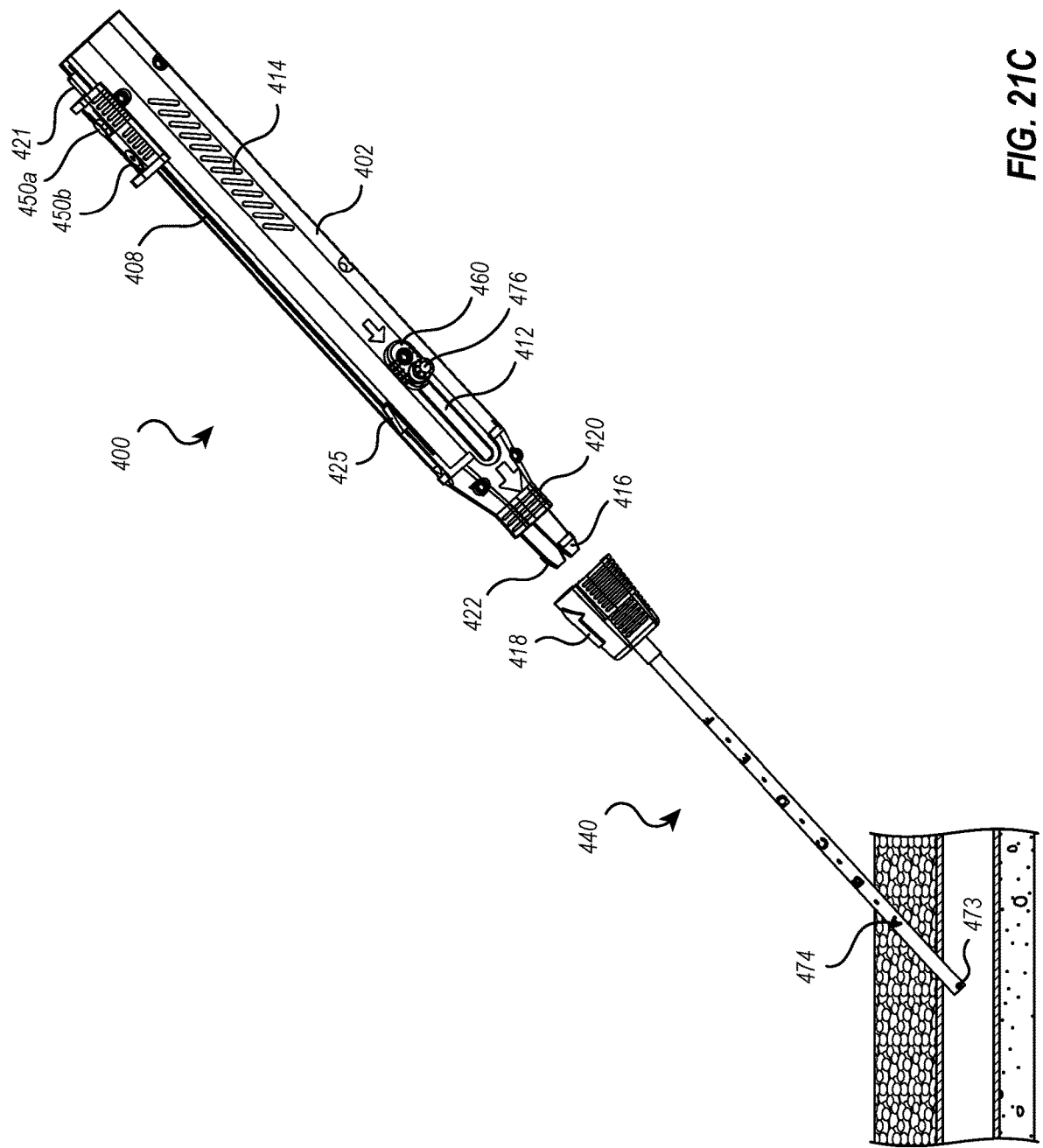
FIGS. 21C-21D illustrates the handle assembly being connected to the delivery sheath according to a method of delivering a closure device to an access site on a vessel.
Figure 21D:
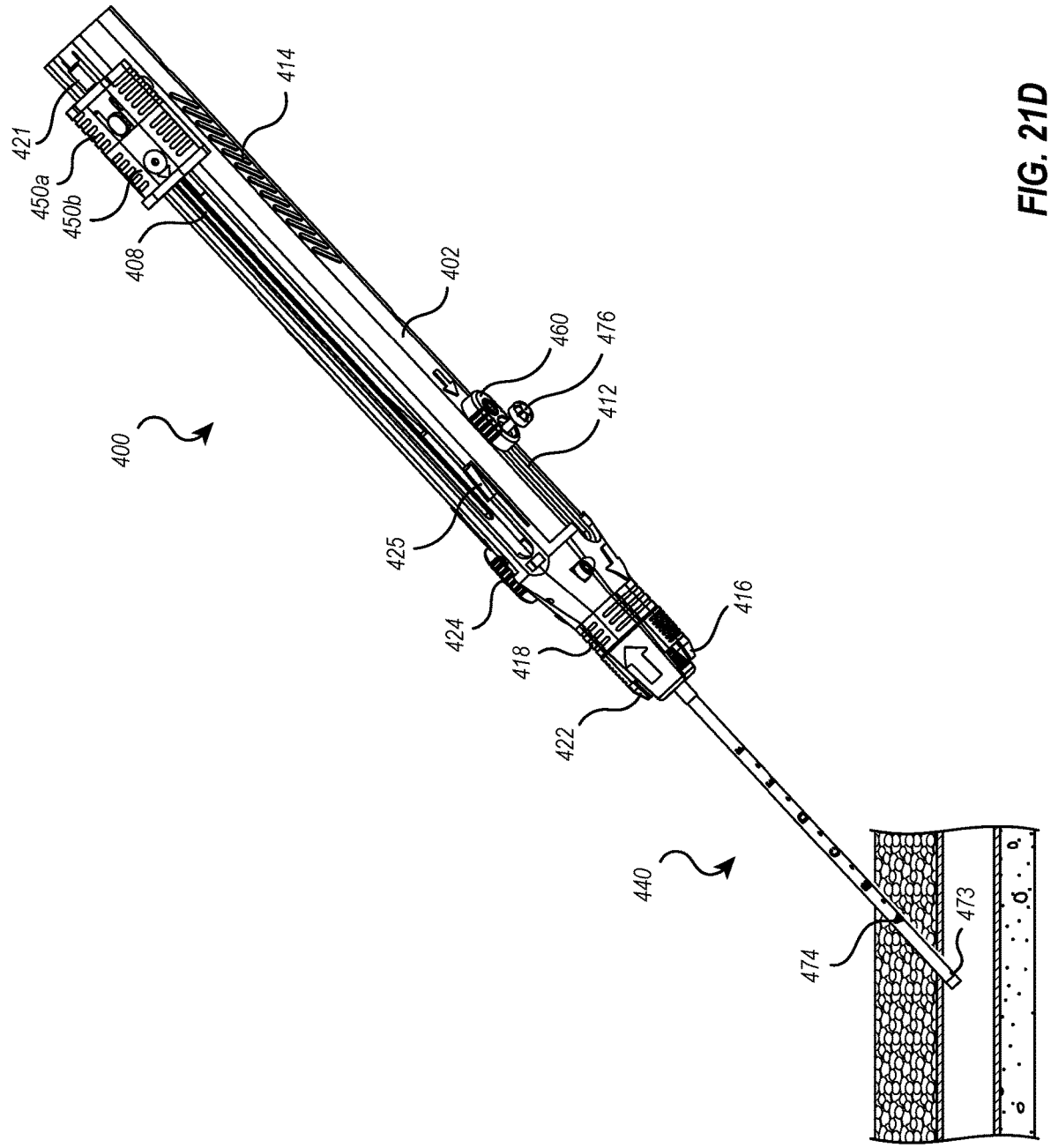

Next, the dilator hub 458 can be disengaged from the sheath hub 418 and the dilator tube 456 can be removed, as shown in FIG. 21B. The delivery sheath 440 can remain in the access tract 22. FIGS. 21C and 21D illustrate a method of connecting the handle assembly 400 to the delivery sheath 440. The handle assembly 400 can be selectively connected to the delivery sheath 440 by engaging the connecting members of the handle assembly 400 with the receiving member or sheath hub 418 of the delivery sheath 440.

Figure 22:
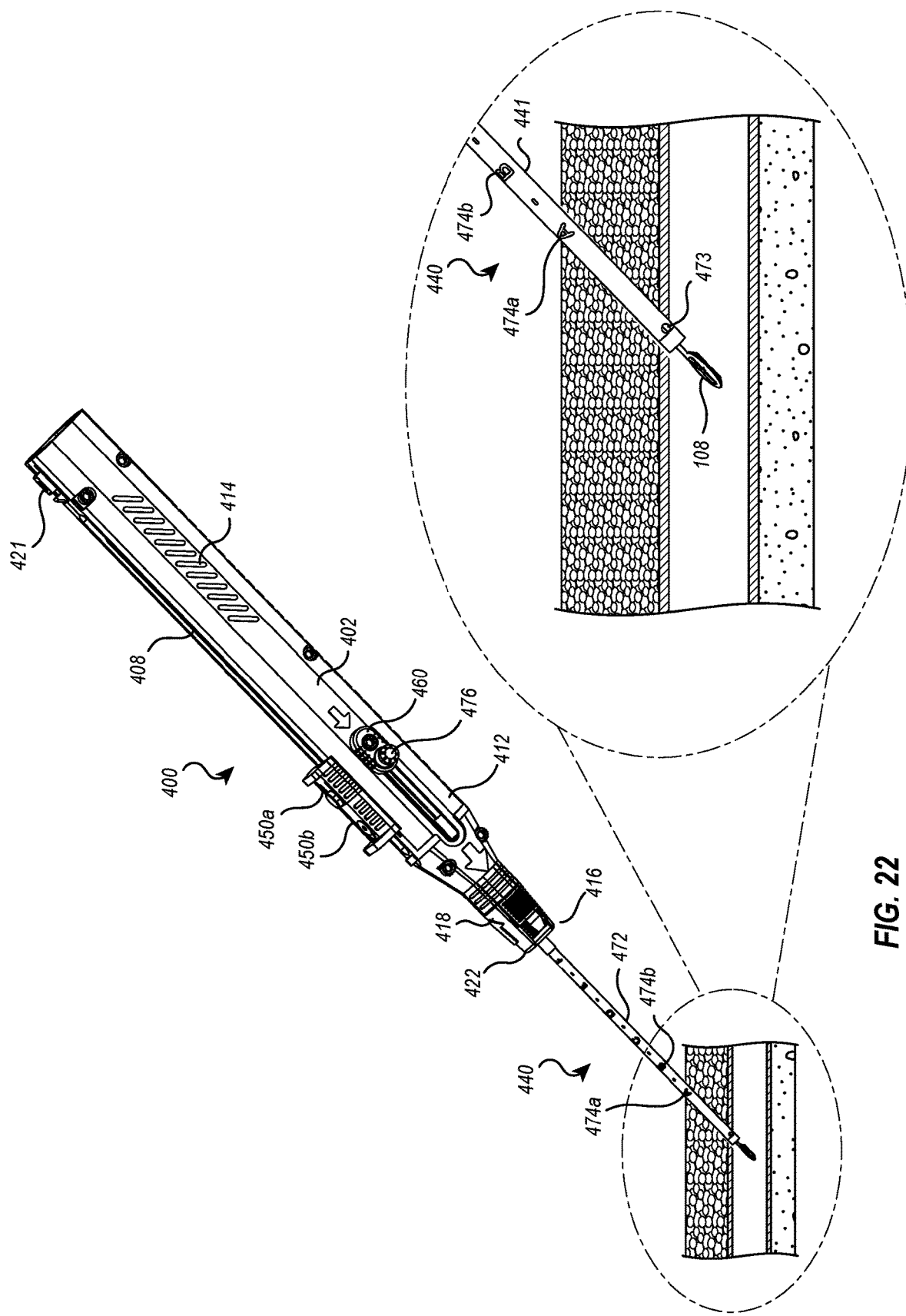
FIG. 22 illustrates partial deployment of the closure device according to a method of delivering a closure device to an access site on a vessel.

Once the handle assembly 400 is connected to the delivery sheath 440, the user can depress the proximal locking assembly 421 to unlock the slider 450 and push the slider in a distal direction towards the distal end 406 of the handle body 400, as illustrated in FIG. 22. This causes the delivery system 430 to eject the anchor 108 into the blood vessel lumen 12 so that the anchor 108 can contact the lumen wall 14 and be positioned on the puncture or access site 18. Once the slider 450 reaches the distal end 406, the anchor 108 should be ejected from the delivery system 430, with the cap 102 and fluid-blocking component 104 remaining in the support tube 442 of the implant assembly 426 within the delivery sheath 440.

Figure 23A:
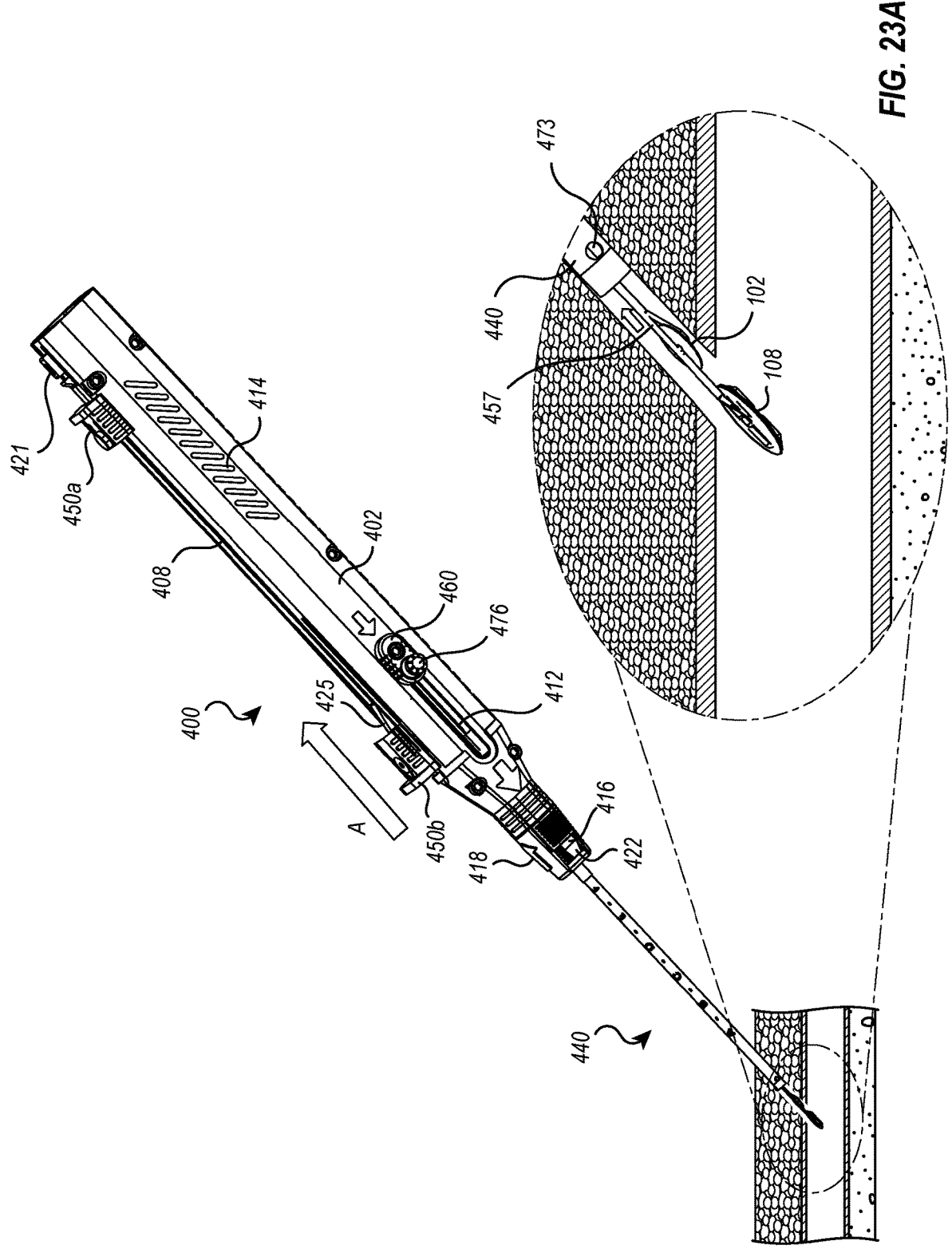
FIGS. 23A-23C illustrate deployment of the closure device and removal of the handle assembly and delivery sheath according to a method of delivering a closure device to an access site on a vessel.

Turning to FIG. 23A, the slider 450 can be configured to slide along the elongate opening 408 until slider portion 450b slides past locking assembly 425, at which point locking assembly 425 can lock slider portion 450b at the distal end of elongate opening 408 (the locking assembly 425 can be formed with the handle body 402, such as having a living hinge connection with the handle body 402 or can be a separated mechanism connected or mounted to the handle body 402). Once slider portion 450b is locked by the locking assembly 425, the user can depress slider portion 450a to release interlocking end 466a from interlocking end 466b, effectively releasing slider portion 450a from slider portion 450b. Slider portion 450a, to which the push wire bend 477 of the push wire 452 is mounted, can be moved proximally to retract the push wire 452 in a proximal direction from the tissue and into the handle assembly 400.

Figure 23B:
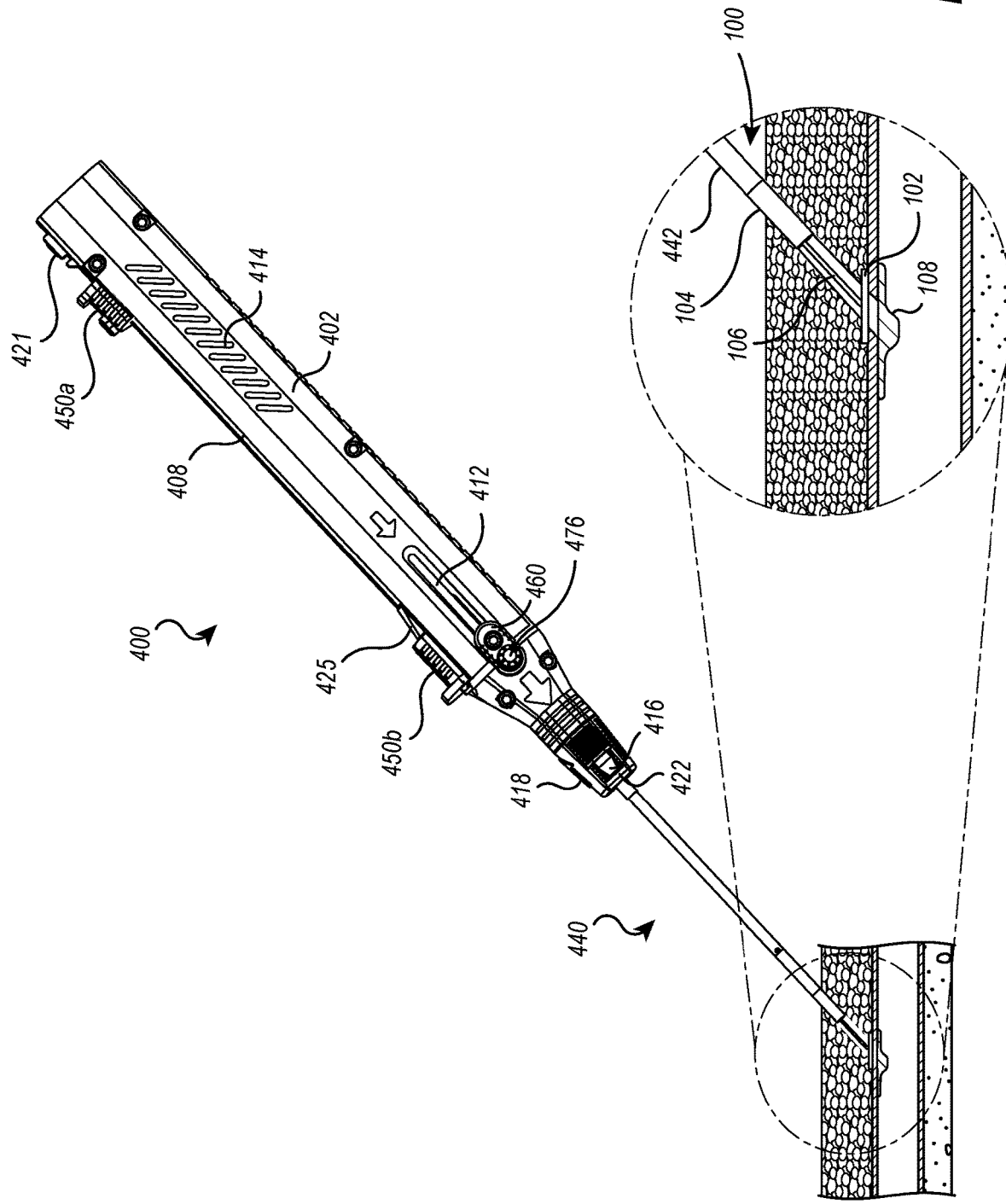
Figure 23C:
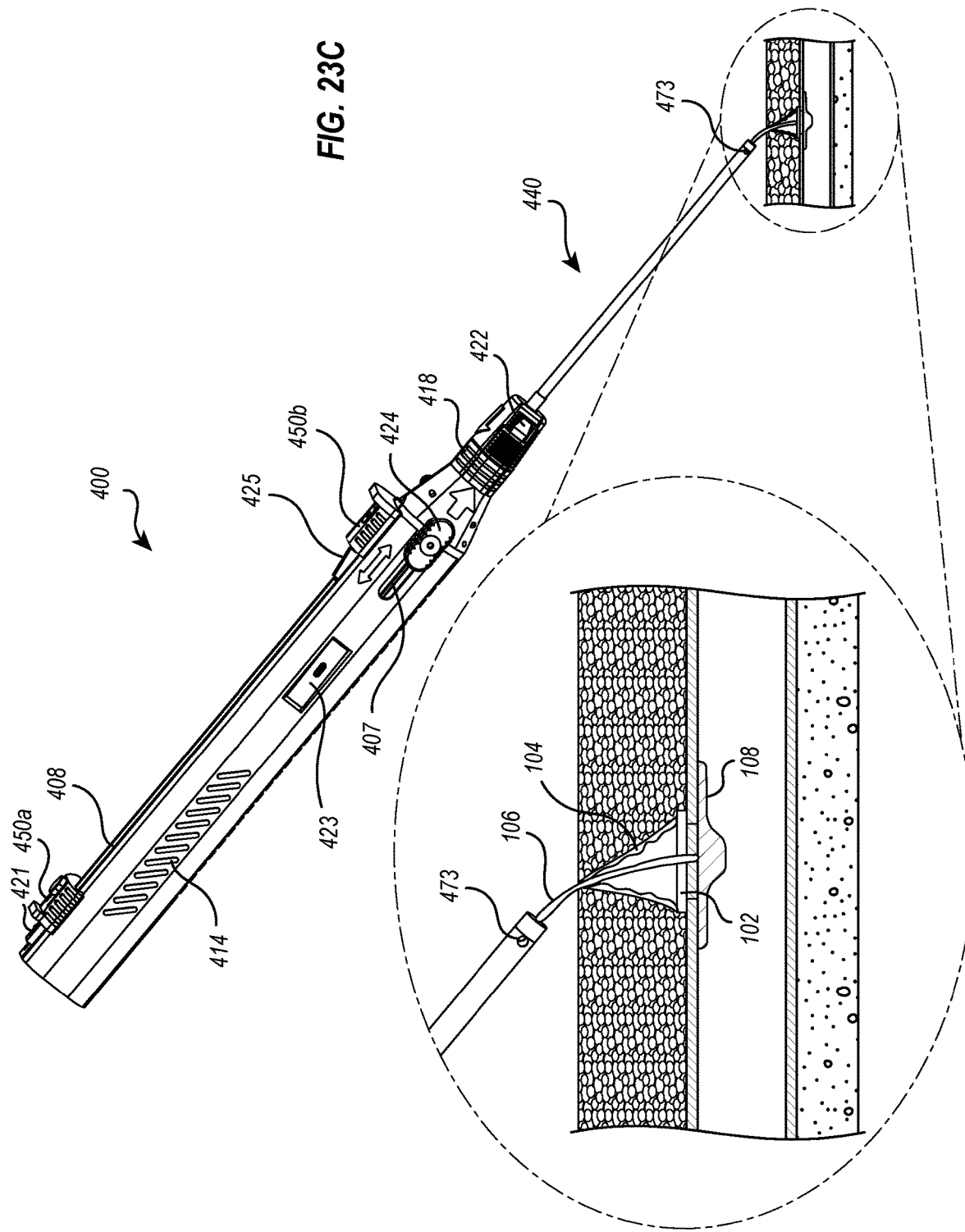

After the anchor 108 is deployed, a user can engage the secondary slider 460 by depressing plunger 476 and pushing the slider 460 in a distal direction toward the distal end 406 of the handle assembly 400. FIG. 23B illustrates the secondary slider 460 engaging the tamper tube 454 (or a portion of the slider 438) and tamping the cap 102 to eject the cap 102 from the delivery system 430. The delivery system 430 can then be pulled in a proximal direction to tension the suture 106 and secure the position of the anchor 108 and cap 102. After the anchor 108 and cap 102 are placed, the release button 424 can be engaged to release the suture 106 and closure device 100 from the delivery system 430 with the fluid-blocking component 104 remaining in the access tract 22, as illustrated in FIG. 23C. Thereafter the suture can be trimmed at or below the level of the skin or tissue.

The articles "a," "an," and "the" are intended to mean that there are one or more of the elements in the preceding descriptions. The terms "comprising," "including," and "having" are intended to be inclusive and mean that there may be additional elements other than the listed elements. Additionally, it should be understood that references to "one embodiment" or "an embodiment" of the present disclosure are not intended to be interpreted as excluding the existence of additional embodiments that also incorporate the recited features. Numbers, percentages, ratios, or other values stated herein are intended to include that value, and also other values that are "about" or "approximately" the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable manufacturing or production process, and may include values that are within 5%, within 1%, within 0.1%, or within 0.01% of a stated value.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

The terms "approximately," "about," and "substantially" as used herein represent an amount close to the stated amount that still performs a desired function or achieves a desired result. For example, the terms "approximately," "about," and "substantially" may refer to an amount that is within less than 5% of, within less than 1% of, within less than 0.1% of, and within less than 0.01% of a stated amount. Further, it should be understood that any directions or reference frames in the preceding description are merely relative directions or movements. For example, any references to "up" and "down" or "above" or "below" are merely descriptive of the relative position or movement of the related elements.

Following are some further example embodiments of the invention. These are presented only by way of example and are not intended to limit the scope of the invention in any way. Further, any example embodiment can be combined with one or more of the example embodiments.

Embodiment 1. A vessel closure device including a bio-absorbable vessel closure device for delivering immediate hemostasis at a puncture site in a wall of a blood vessel, the closure device including an intravascular anchor comprising one or more suture attachment points, an extravascular cap comprising a lumen, a sealant, and a suture connected to at least one of the one or more suture attachment points of the intravascular anchor and threaded through the lumen of the extravascular cap and through the sealant to connect the intravascular anchor to the extravascular cap and to the sealant, wherein each of the intravascular anchor, extravascular cap, sealant, and suture are formed of bioabsorbable materials.

Embodiment 2. The vessel closure device of embodiment 1, wherein the intravascular anchor includes an elongate body comprising a flexible member and a keel.

Embodiment 3. The vessel closure device of any of embodiment 1-2, wherein the extravascular cap is formed of a flexible material.

Embodiment 4. The vessel closure device of any of embodiment 1-3, wherein the sealant comprises polyethylene glycol (PEG).

Embodiment 5. The vessel closure device of any of embodiment 1-4, wherein the suture comprises a distal suture portion and a proximal suture portion.

Embodiment 6. The vessel closure device of any of embodiment 1-5, wherein the diameter of the lumen of the extravascular cap is smaller than the diameter of the distal suture portion.

Embodiment 7. The vessel closure device of any of embodiment 1-6, wherein the intravascular anchor comprises a material selected from Polyglycolic acid (PGA), Poly-L-Latic acid (PLLA), Polycaprolactone (PCL), Poly-DL-lactic acid (PDLLA), Poly trimethylene carbonate (PTMC), and Poly para-dioxanone (PPDO).

Embodiment 8. The vessel closure device of any of embodiment 1-7, wherein the intervascular anchor comprises a plurality of ribs radiating from the keel to a raised edge of the elongate body.

Embodiment 9. The vessel closure device of any of embodiment 1-8, wherein the sealant can expand up to 4 times its original size when introduced to fluids.

Embodiment 10. A vessel closure device for delivering immediate hemostasis at a puncture site in a wall of a blood vessel, the closure device including an intravascular anchor comprising one or more suture attachment points, an extravascular cap comprising a lumen, a sealant comprising a lumen, and a suture connected to at least one of the one or more suture attachment points of the intravascular anchor and threaded through the lumen of the extravascular cap and through the lumen of the sealant to connect the intravascular anchor to the extravascular cap and to the sealant, wherein the suture comprises a proximal suture portion and a distal suture portion, wherein the distal suture portion has a diameter greater than a diameter of the lumen of the extravascular cap, wherein the distal suture portion creates an interference fit to lock the extravascular cap over the puncture site, wherein each of the intravascular anchor, extravascular cap, sealant, and suture are formed of bioabsorbable materials.

Embodiment 11. The vessel closure device of any of embodiment 10, wherein the extravascular cap is formed of a flexible material.

Embodiment 12. The vessel closure device of any of embodiment 10-11, wherein the suture is a braided suture.

Embodiment 13. The vessel closure device of any of embodiment 10-12, wherein the sealant is threaded onto the suture at a location proximal to the extravascular cap.

Embodiment 14. The vessel closure device of any of embodiment 10-13, wherein the sealant when activated locks the extravascular cap in place and coagulates an access tract of the puncture site providing immediate hemostasis.

Embodiment 15. The vessel closure device of any of embodiment 10-14, wherein the intravascular anchor comprises an elongate body comprising a flexible member.

Embodiment 16. The vessel closure device of any of embodiment 10-15, wherein the intravascular anchor comprises a raised keel located on a central axis of the elongate body and spanning the length of the elongate body.

Embodiment 17. The vessel closure device of any of embodiment 10-16, wherein the raised keel comprises one or more suture attachment points.

Embodiment 18. The vessel closure device of any of embodiment 10-17, wherein the sealant comprises polyethylene glycol (PEG).

Embodiment 19. An intravascular anchor for a vessel closure device for delivering immediate hemostasis at a puncture site in a wall of a blood vessel, the intravascular anchor includes an elongate body including a flexible member for conforming to the wall of the blood vessel, a keel having one or more suture attachment points, wherein the keel is an elongate member centrally located along a central axis of the elongate body, wherein the intravascular anchor comprises a bioabsorbable material selected from Polyglycolic acid (PGA), Poly-L-Latic acid (PLLA), Polycaprolactone (PCL), Poly-DL-lactic acid (PDLLA), Poly trimethylene carbonate (PTMC), and Poly para-dioxanone (PPDO).

Embodiment 20. The intravascular anchor of claim 19, wherein the elongate body includes a plurality of ribs radiating from the keel to a raised edge forming the perimeter of the elongate body.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope. It shall be further understood that although the present invention has been described in relation to vessel closure, it is contemplated that the closure component of the present invention may be utilized to close other openings in the body such as PFO openings, or openings formed in organs such as the stomach for certain surgical procedures.

What is claimed is:

1. A vessel closure device for delivering hemostasis at a puncture site in a wall of a blood vessel, the vessel closure device is configured to be disposed within a handle that is configured to attach to a delivery sheath before delivery of the vessel closure device to the wall of the blood vessel through the delivery sheath, the vessel closure device comprising:
   an intravascular anchor comprising one or more suture attachment points;
   an extravascular cap comprising a lumen;
   a sealant comprising polyethylene glycol (PEG), the sealant being configured to expand from about 2 times to about 4 times its original size when introduced to fluids, the sealant being configured to lock the extravascular cap in a spaced relationship with the intravascular anchor when the sealant is disposed on the extravascular cap; and
   a suture connected to at least one of the one or more suture attachment points of the intravascular anchor and threaded through the lumen of the extravascular cap and through the sealant to connect the intravascular anchor to the extravascular cap and to the sealant, a first portion of the suture configured to extend between the intravascular anchor and the extravascular cap and a second portion of the suture configured to extend between the intravascular anchor and the extravascular cap, the first portion of the suture and the second portion of the suture being braided together to form an engagement portion configured to extend between the intravascular anchor and the extravascular cap and having a diameter greater than a remainder of the suture, the engagement portion being configured to cooperate with the extravascular cap,
   wherein each of the intravascular anchor, extravascular cap, sealant, and suture are formed of bioabsorbable materials.

2. The vessel closure device of claim 1, wherein the intravascular anchor comprises an elongate body comprising a flexible member and a keel.

3. The vessel closure device of claim 1, wherein the extravascular cap is formed of an elastomeric material.

4. The vessel closure device of claim 1, wherein the suture comprises a distal suture portion and a proximal suture portion.

5. The vessel closure device of claim 4, wherein the diameter of the lumen of the extravascular cap is smaller than the diameter of the distal suture portion.

6. A vessel closure device for delivering hemostasis at a puncture site in a wall of a blood vessel, the vessel closure device is configured to be disposed within a handle that is configured to attach to a delivery sheath before delivery of the vessel closure device to the wall of the blood vessel through the delivery sheath, the closure device comprising:
   an intravascular anchor comprising one or more suture attachment points;
   an extravascular cap comprising a lumen;
   a sealant comprising a preformed lumen comprising polyethylene glycol (PEG), the sealant being configured to expand about 2 times to about 4 times its original size, including expanding longitudinally, when introduced to fluids to provide secondary sealing of the puncture site and stop oozing of a tissue tract extending to the puncture site; and
   a suture connected to at least one of the one or more suture attachment points of the intravascular anchor and threaded through the lumen of the extravascular cap and through the lumen of the sealant to connect the intravascular anchor to the extravascular cap and to the sealant,
   wherein the suture comprises a proximal suture portion and a distal suture portion, wherein the distal suture portion has a diameter greater than a diameter of the lumen of the extravascular cap, the distal suture portion being formed of a first portion of the suture configured to extend between the intravascular anchor and the extravascular cap and a second portion of the suture configured to extend between the intravascular anchor and the extravascular cap, the first portion of the suture and the second portion of the suture being braided together to form an engagement portion configured to extend between the intravascular anchor and the extravascular cap and having a diameter greater than a remainder of the suture, the engagement portion having the diameter greater than the diameter of the lumen of the extravascular cap and being configured to cooperate with the extravascular cap;
   wherein the distal suture portion creates an interference fit to lock the extravascular cap over the puncture site;
   wherein each of the intravascular anchor, extravascular cap, sealant, and suture are formed of bioabsorbable materials.

7. The vessel closure device of claim 6, wherein the extravascular cap is formed of flexible material.

8. The vessel closure device of claim 7, wherein the sealant when activated locks the extravascular cap in place and coagulates an access tract of the puncture site providing hemostasis.

9. The vessel closure device of claim 6, wherein the suture is a braided suture.

10. The vessel closure device of claim 6, wherein the sealant is threaded onto the suture at a location proximal to the extravascular cap.

11. The vessel closure device of claim 6, wherein the intravascular anchor comprises an elongate body comprising a flexible member.

12. The vessel closure device of claim 11, wherein the intravascular anchor comprises a raised keel located on a central axis of the elongate body and spanning a length of the elongate body.

13. The vessel closure device of claim 12, wherein the raised keel comprises one or more suture attachment points.

* * * * *